US008214228B2

(12) United States Patent
Butler et al.

(10) Patent No.: US 8,214,228 B2
(45) Date of Patent: Jul. 3, 2012

(54) NATIONAL ADDICTIONS VIGILANCE, INTERVENTION AND PREVENTION PROGRAM

(75) Inventors: Stephen F. Butler, Amherst, NH (US); Simon H. Budman, Newton, MA (US); Nathaniel Paul Katz, Newton, MA (US); Albert J. Villapiano, Newton, MA (US)

(73) Assignee: Inflexxion, Inc., Newton, MA (US)

(*) Notice: Subject to any disclaimer, the term of this patent is extended or adjusted under 35 U.S.C. 154(b) by 1106 days.

(21) Appl. No.: 11/647,532

(22) Filed: Dec. 27, 2006

(65) Prior Publication Data
US 2007/0213998 A1    Sep. 13, 2007

Related U.S. Application Data

(60) Provisional application No. 60/755,489, filed on Dec. 29, 2005.

(51) Int. Cl.
*G06Q 10/00* (2012.01)
(52) U.S. Cl. .......................................... 705/2; 705/7.11
(58) Field of Classification Search ............... 705/2, 7.11
See application file for complete search history.

(56) References Cited

U.S. PATENT DOCUMENTS

| | | | |
|---|---|---|---|
| 6,186,145 B1* | 2/2001 | Brown | 128/897 |
| 6,802,810 B2* | 10/2004 | Ciarniello et al. | 600/300 |
| 7,217,134 B2* | 5/2007 | Hansen et al. | 434/322 |
| 7,522,060 B1* | 4/2009 | Tumperi et al. | 340/573.4 |
| 7,761,568 B1* | 7/2010 | Levi et al. | 709/225 |
| 2004/0260155 A1* | 12/2004 | Ciarniello et al. | 600/300 |
| 2006/0064037 A1* | 3/2006 | Shalon et al. | 600/586 |
| 2006/0074719 A1* | 4/2006 | Horner | 705/3 |
| 2006/0229914 A1* | 10/2006 | Armstrong | 705/2 |
| 2007/0033072 A1* | 2/2007 | Bildirici | 705/3 |
| 2007/0118378 A1* | 5/2007 | Skuratovsky | 704/260 |

OTHER PUBLICATIONS

Vista Mental Health Addiction Severity Index Multimedia Version (ASI-MV) Installation and User Guide downloaded from http://www4.va.gov/vdl/documents/Clinical/Mental_Health/ys_asimv_igum.pdf on Sep. 21, 2010.*
Austensen, B., "Louisiana TANF / Substance Abuse Interagency Collaboration Meeting: Lessons form North Carolina," *Welfare Peer Technical Assistance Network*, AFYA, Inc., Takoma Park, MD, 18 (2002).
Budman, Simon H., "Behavioral Health Care Dot-Com and Beyond: Computer-Medicated Communications in Mental Health and Substance Abuse Treatment," *American Psychologist*, pp. 1290-1300 (2000).
Budman, S.H., "Computer-Mediated Addiction Services: Tomorrow Won't Look Like Today," *Behavioral Healthcare Tomorrow*, 14-21 (2002).
Budman, S.H. and Villiapiano, A.J., "Getting Technology Into Substance Abuse Treatment: Change at Many Levels," *The Addictions Newsletter*, American Psychological Association, Division 50, Washington, D.C. 4-8 (2003).

(Continued)

*Primary Examiner* — Mark Fleischer
(74) *Attorney, Agent, or Firm* — Hamilton, Brook, Smith & Reynolds, P.C.

(57) ABSTRACT

A substance abuse surveillance system comprising a source of respondent responses to a self-administered virtual interview and a data collector coupled to receive from the source multiple respondent responses and analyzing the same in near real-time to form current substance abuse data, the data collector allowing access to the current substance abuse data by third parties. The data collector is coupled to the source in a manner enabling delay-free, continuous feed of the respondent responses.

52 Claims, 203 Drawing Sheets

OTHER PUBLICATIONS

Budman, S.H., et al., "How to Get Technological Innovation Used in Behavioral Health Care: Build it and They Still Might not Come," *Psychotherapy: Theory/Research/Practice/Training*, 40(1/2):45-54 (2003).

Butler, S.F., et al., "Initial Validation of a Computer-Assisted Addiction Severity Index: The ASI-MV," *Psychology of Addictive Behaviors*, 15(1):4-12 (2001).

Butler, S.F., et al., "Predicting Addiction Severity Index (ASI) Interviewer Severity Ratings for a Computer-Administered ASI," *Psychological Assessment*, 10(4):399-407 (1998).

Butler, S.F., "The Bath Water or the Baby?," *Addiction* 99(4):413-414 (2004).

Cacciola, J.S., et al., "A Comparison of Self-Administered ASI with the Standard ASI Interview," In L.S. Harris (Ed.), *Problems of Drug Dependence*, 1997: Proceedings of the 59th Annual Scientific Meeting, The College on Problems of Drug Dependence, Inc. (NIH Publications No. 98-4305, p. 245). Rockville, MD: National Institutes of Health (1998).

Driscoll, M., et al., "The Computerized, Multimedia Addiction Severity Index," *San Francisco Practice Improvement Collaborative Newsletter* (www.dph.sf.ca.us/php/pic). 5:14-16 (2004).

Hendricks, V.M., et al., "The Addiction Severity Index: Reliability and Validity in a Dutch Addict Population," *Journal of Substance Abuse Treatment*, 6:133-141 (1989).

Hodgins, D. C. and El-Guebaly, N., "More Data on the Addiction Severity Index: Reliability and Validity with the Mentally Ill Substance Abuser," *Journal of Nervous and Mental Disease*, 180:197-201 (1992).

Langerbucher, J. and Merrill, J., "The Validity of Self-Reported Cost Events by Substance Abusers: Limits, Liabilities, and Future Directions," *Evaluation Review*, 25:2, 184-210 (2001).

McLellan A.T., et al., "An Improved Diagnostic Evaluation Instrument for Substance Abuse Patients, The Addiction Severity Index," *The Journal of Nervous and Mental Disease*, 168(1):26-33 (1980).

McLellan, et al., "Guide to the Addiction Severity Index: Background Administration and Field TestingResults," *U.S. Department of Health and Human Services*, Rockville, MD (1985).

McLellan, A.T., et al., "New Data from the Addiction Severity Index: Reliability and Validity in Three Centers," *Journal of Nervous and Mental Disease*, 173:412-423 (1985).

McLellan, A.T., et al., "Similarity of Outcome Predictors Across Opiate, Cocaine, and Alcohol Treatments: Role of Treatment Services," *Journal of Consulting and Clinical Psychology*, 62:1141-1158 (1994).

McLellan, A. T., et al., "The Fifth Addition of the Addiction Severity Index," *Journal of Substance Abuse Treatment*, 9:199-213 (1992).

Rosen, C. S., et al., "Consistency of Self-Administered and Interview-Based Addiction Severity Index Composite Scores," *Addiction*, 95:419-425 (2000).

\* cited by examiner

| Question ID | Onscreen Text | Actor | Audio Recordings | ASI-MV Codes | Skip Logic | Consistency | Extreme Values |
|---|---|---|---|---|---|---|---|
| | Click Screen to Start | | None | | | | |
| | | | Please remember, when you are finished with your selection click enter to continue to the next screen. | | | | |
| | Repeat Question | | None | | | | |
| | Back | | None | | | | |
| | Next | | None | | | | |
| Facility | Facility | | None | (string variable) | Required | | |
| Facity | City | | None | (string variable) | Required | | |
| Facstate | State | | None | (string variable) | Required | | |
| G1 | Client # | | None | (string variable) | | | |
| G5 | TestDate | | None | (Date Variable from system) | | | |
| AdmDate | Admission Date | | None | (string variable) | | | |
| ProgNum | Program # | | None | (string variable) | | | |
| InterCode | Interview Code | | None | (string variable) | | | |
| FNAME | Client's First Name | | None | (string variable) | | | |
| LNAME | Client's Last Name | | None | (string variable) | Required | | |
| NameBirth | Client's Last Name at birth Click here if same | | None | (string variable) | Required | | |
| CityBirth | City where client was born | | None | (string variable) | Required | | |
| ADD1 | Client's address | | None | (string variable) | | | |
| CITY | City | | None | (string variable) | | | |
| STATE | State | | None | (drop down selection) | Required | | |
| ZIP | Zip Code | | None | 5 digits | Required | | |

FIG. 6A

| Question ID | Onscreen Text | Actor | Audio Recordings | ASI-MV Codes | Skip Logic | Consistency | Extreme Values |
|---|---|---|---|---|---|---|---|
| (ASIG014Y) (ASIG014M) | How long have you been living at your present address? Years Months [enter digits] | | None | ASIG014Y=2digit code ASIG014M=2digit code (up to 11) | | | |
| (ASIG015) | Is this address owned by you or your family? Yes No | | None | 1 = Yes (owned) 0 = No (not owned) | | | |
| MINUTES | | | | Total minutes to completion of ASI-MV | | | |
| G50 | Service Anticipated: [drop-down menu] - Residential/ Inpatient - Outpatient/non- Methadone - Methadone/ LAAM - Drug Court - Probation/Parole - DUI/DWI - Other Corrections - TANF (Welfare) - Other | | None | 1 = Residential/ Inpatient 2 = Outpatient/non-Methadone 3 = Methadone/ LAAM 4 = Drug Court 5 = Probation/Parole 6 = DUI/DWI 7 = Other Corrections 8 = TANF (Welfare) 9 = Other | Required [Staff selects expected treatment modality most appropriate for client] | | |

FIG. 6B

| Question ID | Onscreen Text | Actor | Audio Recordings | ASI-MV Codes | Skip Logic | Consistency | Extreme Values |
|---|---|---|---|---|---|---|---|
| Insurer | The Client's primary Payer/Insurance: [drop-down menu] - Medicaid/Medicare - Medicare (ONLY) - Self-Pay - Uninsured/Exhausted Benefits - Commercial Payer - Other | | None | 1 =Medicare/ Medicaid<br>2 = Medicare only<br>3 = Self-pay<br>4 = Uninsured/ Exhausted<br>:<br>:<br>: | If=5 go to Commercial<br><br>If=6 go to Other | | |
| commercial | Commercial Insurer | | None | (string variable) ... | | | |
| Other | Other | | None | (string variable) ... | | | |
| Version (NOTE... | List Versions of ASI-MV | | None | ASI-MV English =1<br>ASI-MV Spanish=2<br>:<br>:<br>: | | | |
| | Start ASI-MV | | None | | Go to version selected above | | |
| | Opening Scene 1 | George | Hi, and welcome to the Addiction Severity Index or ASI. My name is George. | | | | |
| | Scene 1 | Angela | ...and I'm Angela! | | | | |
| | Scene 1 | George | ...and we're here to help you get to the interviews that make up the ASI. | | | | |
| | Scene 1 (end of Scene 1) | Angela | Angela: That's right! And as Helpers, it's our job to guide you along the way. | | | | |
| Enter Prompt | none | Angela | Remember, when you finish selecting your answer, click on the NEXT button to go to the next question. | none | | | |

FIG. 6C

| Question ID | Onscreen Text | Actor | Audio Recordings | ASI-MV Codes | Skip Logic | Consistency | Extreme Values |
|---|---|---|---|---|---|---|---|
| Skip Alert Dialogue box | Are you sure you want to move on without answering this question? Yes No | Angela | Are you sure you want to move on without answering this question? Yes, or No | If Yes, record -2 for skipped question | If Yes, go to next question. If No, return to question. ALL ASI-MV QUESTIONS GET THIS | | |
| (ASIG016) | Please enter your Date of Birth Year Month Day [date counters] | Angela | Using the up and down arrows please enter the month, day and year of your birth. Clicking and holding down the arrows will speed the counter up and down. | Date variable | | | |
| Age | Is [CALCULATED VALUE] your correct age? Yes, this is my correct age. No, this is NOT my correct age. | George | Is this your correct Age? Click Yes or No | CALCULATE USING DATE ASIG016 AND TODAY'S DATE. Up to 3 digits 1 = Yes 0 = No If click Yes (=1), store value as Age variable. | If click No (=0), RE-PRESENT ASIG016 | | |

FIG. 6D

| Question ID | Onscreen Text | Actor | Audio Recordings | ASI-MV Codes | Skip Logic | Consistency | Extreme Values |
|---|---|---|---|---|---|---|---|
| (ASIG017) | What race do you consider yourself?<br><br>White (not Hispanic)<br>African American (Black, not Hispanic)<br>American Indian<br>Alaskan Native<br>Asian Indian<br>Chinese<br>Filipino<br>Japanese<br>Korean<br>Vietnamese<br>Other Asian<br>Mexican (Mexican American, Chicano)<br>Puerto Rican<br>Cuban<br>Other Spanish (Hispanic or Latino(a))<br>Native Hawaiian<br>Guamanian<br>Samoan<br>Other Pacific Islander<br>Other Race | Angela (alternate with George for racial selections) | From the list provided, please click on the race that most closely represents your race.<br><br>• White<br>• Black or African American<br>• American Indian<br>• Alaskan Native<br>• Asian Indian<br>• Chinese<br>• Filipino<br>• Japanese<br>• Korean<br>• Vietnamese<br>• Other Asian<br>• Mexican, Mexican American, Chicano<br>• Puerto Rican<br>• Cuban<br>• Other Spanish, Hispanic or Latino<br>• Native Hawaiian<br>• Guamanian<br>• Samoan<br>• Other Pacific Islander<br>• Other Race | 1=White<br>2=African American<br>3=American Indian<br>4=Alaskan Native<br>5=Asian Indian<br>10=Chinese<br>11=Filipino<br>12=Japanese<br>13=Korean<br>14=Vietnamese<br>15=Other Asian<br>6=Mexican (Mexican American, Chicano)<br>7=Puerto Rican<br>8=Cuban<br>16=Other Spanish (Hispanic or Latino(a))<br>17=Native Hawaiian<br>18=Guamanian<br>19=Samoan<br>20=Other Pacific Islander<br>9=Other Race<br>research database recodes occur here or at another point?<br>NOTE: | | | |

FIG. 6E

| Question ID | Onscreen Text | Actor | Audio Recordings | ASI-MV Codes | Skip Logic | Consistency | Extreme Values |
|---|---|---|---|---|---|---|---|
| (ASIG018) | What is your religious preference?<br>Protestant<br>(Some examples of this would include Baptist, Methodist, Episcopalian, Evangelical, or any non-Catholic Christian.)<br>Catholic<br>Jewish<br>Islamic<br>Buddhist<br>Other<br>None | George | What is your religious preference?<br>•Protestant. Some examples of this would include Baptist, Methodist, Episcopalian, Evangelical, or any non-Catholic Christian.)<br>•Catholic<br>•Jewish<br>•Islamic<br>•Buddhist<br>•Other<br>•None | 1 = Protestant<br>2 = Catholic<br>3 = Jewish<br>4 = Islamic<br>5 = Other<br>6 = None | | | |
| (ASIG010) | Are you male or female?<br>Male blinks when said above<br>Female blinks when said above | George | Are you male or female? | 1 = Male<br>2 = Female | | | |
| (ASIG019) | In the last 30 days, have you been in a place where drugs and alcohol were not readily available, such as:<br>- Jail/Prison<br>- Inpatient Alcohol or Drug Treatment<br>- Inpatient Medical Treatment<br>- Inpatient Psychiatric Treatment<br>- Other<br>- None | George | In the last 30 days, have you been in a place where drugs and alcohol were not readily available, such as:<br>• Jail/Prison<br>• Inpatient Alcohol or Drug Treatment<br>• Inpatient Medical Treatment<br>• Inpatient Psychiatric Treatment<br>• Other<br>• None | 1 = None<br>2 = Jail/prison<br>3 = Inpatient alc/drug tx<br>4 = Inpatient medical<br>5 = Inpatient Psych.<br>6 = Other | If G19 = 1, skip G20 and go to General Transition Scene 2<br>If G19 > 1, go to G20 | If ASIG019 = 2 & ASIL021 = 0, Consistency Alert<br>or<br>If ASIG019 = 4 & ASIM001 = 0,<br>. . . | |

FIG. 6F

| Question ID | Onscreen Text | Actor | Audio Recordings | ASI-MV Codes | Skip Logic | Consistency | Extreme Values |
|---|---|---|---|---|---|---|---|
| (ASiG020) | How many days out of the last 30 have you been in this setting?<br><br>Days | George | How many days out of the last 30 have you been in this setting? Remember, clicking and holding the down the arrows will speed the counter up and down. | Counter 2-digit (MAX = 30) | | | |
| General Transition Scene 2 | None<br>[video & audio] | Angela | Great! Let's get started with the ASI. This interview will take about 60 minutes to complete. | | | | |
| Medical Transition Scene 3 | None<br>[video & audio] | George | The first interview you have is with Dr. Simmons. She's going to ask you a few questions about your general health. That's her door straight ahead. Just click on it to get started. | | | | |
| Medical Section | | | | | | | |
| Medical Introduction Scene 4 | None<br>[video & audio] | Dr. Simmons | Hello, I'm Dr. Simmons. I have a few questions I want to ask you about your general and physical health. | | | | |
| Skip Alert Dialogue box | Are you sure you want to move on without answering this question?<br>Yes<br>No | Dr. Simmons | Are you sure you want to move on without answering this question?<br>Yes, or<br>No | If Yes, record -2 for skipped question | If Yes, go to next question.<br>If No, return to question.<br>ALL ASI-MV QUESTIONS GET THIS<br>.<br>.<br>. | | |

FIG. 6G

| Question ID | Onscreen Text | Actor | Audio Recordings | ASI-MV Codes | Skip Logic | Consistency | Extreme Values |
|---|---|---|---|---|---|---|---|
| No-Skip Alert Dialogue box | This question is important, so please try to answer.<br>Yes<br>No | Dr. Simmons | This question is important, so would you please try to choose an answer?<br>Yes<br>No | If No, record -2 for skipped question | If No, go to next question.<br>If Yes, * * * | | |
| Extreme Alert Dialogue box | Is this the answer you want to give ___?<br>Yes<br>No | Dr. Simmons | Is this the answer you want to give? <br>Yes<br>No | If Yes, record answer to question | If No, return to question | | If Yes, add * * * |
| Enter Prompt | none | Dr. Simmons | Remember, when you finish selecting your answer, click on the NEXT button to go to the next question. | None | | | |
| (ASIM001) | Estimate how many different times in your life have you been hospitalized overnight for physical or medical problems. [Side Bar] Physical or medical problems include:<br>-operations<br>-accidents<br>-illnesses<br>-DTs or overdoses<br>Do not include:<br>-detox hospital stays<br>-psychiatric problems<br>-normal childbirth visits<br>-emergency room visits<br>Never | Dr. Simmons | Estimate how many different times in your life have you been hospitalized overnight for physical or medical problems.<br><br>Physical or medical problems include: operations, accidents, illnesses, DTs or overdoses.<br><br>Do not include detox hospital stays, normal psychiatric problems, normal childbirth visits or emergency room visits.<br><br>Use the up and down arrows to enter the number of hospitalizations.<br><br>If Never, click this button. | Coded as a 2 digit variable<br><br>0 = Never | If ASIM001 = 0, go to ASIM003<br><br>If ASIM001 > 0 go to ASIM002 | If ASIG019 = 4 & ASIM001 = 0, Consistency Alert<br><br>If no: FLAG (if they don't change it, accept answer and add both questions and answers to Consistency Report and * * * | If ASIM001 > 12, Extreme Alert and if not changed, add question and answer to the Extreme Values Report |

FIG. 6H

| Question ID | Onscreen Text | Actor | Audio Recordings | ASI-MV Codes | Skip Logic | Consistency | Extreme Values |
|---|---|---|---|---|---|---|---|
| (ASIM002Y) (ASIM002M) | About how long ago was your last overnight hospitalization for a physical or medical problem. [Side Bar] Physical or medical problems include: -operations -accidents -illnesses -DTs and overdoses Do not include: -detox hospital stays -psychiatric problems -normal childbirth visits -emergency room visits Years Months Less than a month ago | Dr. Simmons | About how long ago was your last overnight hospitalization for a physical or medical problem. Remember, do not include detox hospital stays, psychiatric problems, normal childbirth visits, or emergency room visits. Use the up and down arrows to enter the number of years and/or months. If it was less than a month ago, click this button. | Year and Month counters ASIM002Y =year counter ASIM002M=month counter (up to 11) (MAX value = AGE) -1 = Less than a month ago If skipped because ASIM001 = 0, code ASIM002Y & ASIM002M as -1 | | | |
| | In the last 30 days, about how many days did you visit a hospital emergency room? Day counter None | Dr. Simmons | In the last 30 days, about how many days did you visit a hospital emergency room? If none, click here. | Coded as a 2 digit variable (MAX = 30) 0 = None | | | |
| | Are you currently pregnant? Yes No Not Sure | Dr. Simmons | Are you currently pregnant? Yes No If Not Sure, click here. | 1 = Yes 0 = No -9 = Not Sure | Skip if ASIG010 = 1 (male) | | |

FIG. 61

| Question ID | Onscreen Text | Actor | Audio Recordings | ASI-MV Codes | Skip Logic | Consistency | Extreme Values |
|---|---|---|---|---|---|---|---|
| (ASIM003) | Do you have an ongoing or longstanding physical or medical problem that limits or interferes with your daily activities? [Side Bar] An ongoing or long standing medical problem is one that requires continuous or regular care by you or your doctor. Examples include High Blood Pressure,...Asthma. Yes No | Dr. Simmons | Do you have an ongoing or longstanding physical or medical problem that limits or interferes with your daily activities? An ongoing or longstanding medical problem is one that requires continuous or regular care by you or your doctor. Examples include High Blood Pressure, Diabetes, Ulcers, Pancreatitis, Hepatitis,...Asthma. Click Yes or No. | 1 = Yes 0 = No | | | |
| M3CZ1 = headaches /migraines M3CZ 2 = Epilepsy/seizures M3CZ 3 = Asthma M3CZ 4 = Emphysema or COPD M3CZ 5 =Tuberculosis or TB M3CZ 6 = heart disease | Are you having problems with any of the following. Please select all that apply. - Frequent headaches or migraines - Epilepsy or seizure disorder -Asthma or other breathing problems -Emphysema or COPD -Tuberculosis or TB -Cardiovascular or heart disease -High blood pressure | | Are you having problems with any of the following. Please select all that apply. - Frequent headaches or migraines - Epilepsy or seizure disorder -Asthma or other breathing problems -Emphysema or COPD -Tuberculosis or TB -Cardiovascular or heart disease -High blood pressure | Each variable will be given a separate value 1 = Yes [Selected] 0 = No [Not selected] M3CZ1 = headaches /migraines M3CZ 2 = Epilepsy/seizures M3CZ 3 = Asthma M3CZ 4 = Emphysema or COPD M3CZ 5 =Tuberculosis or TB M3CZ 6 = heart disease | | | |

FIG. 6J

| Question ID | Onscreen Text | Actor | Audio Recordings | ASI-MV Codes | Skip Logic | Consistency | Extreme Values |
|---|---|---|---|---|---|---|---|
| M3CZ 7 = High blood pressure<br>M3CZ 8 = HIV or AIDS<br>M3CZ 9 = Diabetes<br>M3CZ 10 = Liver disease like Cirrhosis or Hepatitis A, B, or C<br>M3CZ 11 = Bleeding when you throw up or go to the bathroom<br>M3CZ 12 = Pancreatitis<br>M3CZ 13 = Ulcers, Gastritis or other stomach problems<br>M3CZ 14 = Arthritis or joint pain<br>M3CZ 15 = Neuropathy<br>M3CZ 16 = Cancer<br>M3CZ 17 = Chronic pain<br>M3CZ 18 = Others, not listed<br>M3CZ 19 = None | -HIV or AIDS<br>-Diabetes<br>-Liver disease(Cirrhosis or Hepatitis -A, B, or C)<br>-Bleeding when you throw up or go to the bathroom<br>-Pancreatitis<br>-Ulcers, Gastritis or other stomach problems<br>-Arthritis or joint pain<br>-Neuropathy or weakness, numbness, and/or pain in hands and feet<br>-Cancer<br>-Chronic or Persistent pain<br>-Others, not listed<br>-None | | -HIV or AIDS<br>-Diabetes<br>-Liver disease like Cirrhosis or Hepatitis -A, B, or C<br>-Bleeding when you throw up or go to the bathroom<br>-Pancreatitis<br>-Ulcers, Gastritis or other stomach problems<br>-Arthritis or joint pain<br>-Neuropathy or weakness, numbness, and/or pain in hands and feet<br>-Cancer<br>-Chronic or Persistent pain<br>-Others, not listed<br>-None | M3CZ 7 = High blood pressure<br>M3CZ 8 = HIV or AIDS<br>M3CZ 9 = Diabetes<br>M3CZ 10 = Liver disease like Cirrhosis or Hepatitis A, B, or C<br>M3CZ 11 = Bleeding when you throw up or go to the bathroom<br>M3CZ 12 = Pancreatitis<br>M3CZ 13 = Ulcers, Gastritis or other joint pain<br>M3CZ 15 = Neuropathy<br>M3CZ 16 = Cancer<br>M3CZ 17 = Chronic pain<br>M3CZ 18 = Others, not listed<br>M3CZ 19 = None | | | |

FIG. 6K

| Question ID | Onscreen Text | Actor | Audio Recordings | ASI-MV Codes | Skip Logic | Consistency | Extreme Values |
|---|---|---|---|---|---|---|---|
| (ASIM004) | Do you take (or should you be taking) any medication for a long-standing, ongoing physical problem?<br><br>[Side Bar]<br>Do not include medicine taken for a cold or minor infection or medicine for emotional or psychological problems such as depression or anxiety.<br><br>Yes<br>No | Dr. Simmons | Do you take, or should you be taking, any medication for a long-standing, ongoing physical problem?<br><br>Do not include medicine taken for a cold or minor infection or medicine for emotional or psychological problems such as depression or anxiety.<br><br>Click Yes or No. | 1 = Yes<br>0 = No | | | |
| M4Apain | Do you have a pain problem? That is physical pain that is more than the usual aches and pains?<br><br>Yes<br>No | Dr. Simmons | Do you have a pain problem? That is physical pain that is more than the usual aches and pains?<br><br>Click Yes or No. | 1 = Yes<br>0 = No | If M4APAIN = 1, go to M4B<br><br>If M4APAIN = 0, go to ASIM005 | | |
| M4Bpain | For how long have you had a pain problem?<br><br>Years<br>Months<br>Less than a month ago | Dr. Simmons | For how long have you had a pain problem?<br><br>Use the up and down arrows to enter the number of years and months.<br><br>If it was less than a month ago, click this button. | Year/Month counter, variable coded in months<br><br>.1 = Less than a month ago<br><br>(MAX value = AGE) | Go to M4Cpain variables | | |

FIG. 6L

| Question ID | Onscreen Text | Actor | Audio Recordings | ASI-MV Codes | Skip Logic | Consistency | Extreme Values |
|---|---|---|---|---|---|---|---|
| M4C pain variables<br><br>M4Cpain1<br>M4Cpain2<br>M4Cpain3<br>M4Cpain4<br>M4Cpain5<br>M4Cpain6<br>M4Cpain7 | Please click on all the places where you have pain:<br><br>- Head<br>- Face, ears, mouth or jaw<br>- Shoulders or arms<br>- Hips, knees or legs<br>- Back or neck<br>- Stomach, abdomen, or pelvis<br>- Other | Dr. Simmons | Please click on all the places where you have pain:<br><br>- Head<br>- Face, ears, mouth or jaw<br>- Shoulders or arms<br>- Hips, knees or legs<br>- Back or neck<br>- Stomach, abdomen, or pelvis<br>- Other | Each variable will be given a separate value<br>1 = Yes [Selected]<br>0 = No [Not selected] | | | |
| M4Dpain | How many days in the past 30 days have you had pain?<br><br>Days [counter]<br>None | Dr. Simmons | How many days in the past 30 days have you had pain?<br>Please click on the up or down arrow on this counter to show the number of days - or if None, click here. | Coded as a 2 digit variable (MAX = 30)<br>0 = None | Go to M4Epain | | |
| M4Epain | In the past 30 days, have you taken any prescribed opiate medicine for your pain?<br>[Side Bar]<br>Examples of opiate medications are Morphine, Vicodin, Codeine and Oxycontin.<br><br>Do not include non-opiate pain medication such as Celebrex, Motrin, Tylenol or Aleve.<br><br>Yes<br>No | Dr. Simmons | In the past 30 days, have you taken any prescribed opiate medicine for your pain?<br><br>Examples of opiate medications are Morphine, Vicodin, Codeine and Oxycontin.<br><br>Do not include non-opiate pain medication such as Celebrex, Motrin, Tylenol or Aleve.<br><br>Click Yes or No. | 1 = Yes<br>0 = No | If M4Epain = 1, enable OP questions<br><br>If M4Epain = 1 OR 0, go to ASIM005 | | |

FIG. 6M

| Question ID | Onscreen Text | Actor | Audio Recordings | ASI-MV Codes | Skip Logic | Consistency | Extreme Values |
|---|---|---|---|---|---|---|---|
| (ASIM005) | Do you receive any money from the government, an insurance company or a former employer for a physical disability? [Side Bar] Answer No if you receive a pension for emotional or psychiatric problems. Yes No | Dr. Simmons | Do you receive any money from the government, an insurance company or a former employer for a physical disability? Answer No if you receive a pension for emotional or psychiatric problems. Click Yes or No. | 1 = Yes<br>0 = No | | If ASIM005 = 1 & ASIE015 = 0, Consistency Alert<br><br>If no: FLAG (if they don't) · · · | |
| (ASIM006) (Composite question) | In the past 30 days, about how many days have you had physical or medical problems. [Side Bar] Include illness, pains, discomfort, disability, or a severe cold or flu. Do not include alcohol or drug symptoms or withdrawal. Days [counter] None | Dr. Simmons | In the past 30 days, about how many days have you had physical or medical problems.<br><br>Include illness, pains, discomfort, disability, or a severe cold or flu.<br><br>Do not include alcohol or drug symptoms or withdrawal.<br><br>If None, click this button. | Coded as a 2 digit variable (MAX 30)<br><br>0 = None | If -2 (refused), show No-Skip Alert | | |
| (ASIM007) (Composite question) | In the past 30 days, how troubled or bothered have you been by physical or medical problems? Not at all · · · | Dr. Simmons | In the past 30 days, how troubled or bothered have you been by physical or medical problems?<br>• Not at all<br>• Slightly<br>• Moderately<br>• Considerably<br>• Extremely | 0 = Not at all<br>1 = Slightly<br>2 = Moderately<br>3 = Considerably<br>4 = Extremely | If -2 (refused), show No-Skip Alert | | |

FIG. 6N

| Question ID | Onscreen Text | Actor | Audio Recordings | ASI-MV Codes | Skip Logic | Consistency | Extreme Values |
|---|---|---|---|---|---|---|---|
| (ASIM008) (Composite question) | How important to you now is additional treatment for these medical problems? [Side Bar] Additional treatment means more treatment than you are currently receiving for your medical problems. Not at all Slightly Moderately Considerably Extremely | Dr. Simmons | How important to you now is additional treatment for these medical problems? Additional treatment means more treatment than you are currently receiving for your medical problems. • Not at all • Slightly • Moderately • Considerably • Extremely | 0 = Not at all 1 = Slightly 2 = Moderately 3 = Considerably 4 = Extremely | If -2 (refused), show No-Skip Alert | | |
| (ASIM009) | None | | None | (calculated variable 1-9) Medical Severity Rating | COMPUTE medsev = ASIM003 + ASIM006. | | * |
| COMPMED | None | | None | Medical Composite Score (.000-1.000) | VARIABLES IN THE DATABASE ASIM006 Physical or medical problems past | | * * |
| Medical End Scene 5 | [video and audio] | Dr. Simmons | That's all the questions I have for you. Thanks for your time! | | | | |
| Employment Transition Scene 6 | [video and audio] | Angela | That went well. Your next interview is right across the street. Mr. Rivera wants to ask you a few questions about your employment situation. Click on the door and go right in! | | | | |
| Employment Section | | | | | | | |

FIG. 6O

| Question ID | Onscreen Text | Actor | Audio Recordings | ASI-MV Codes | Skip Logic | Consistency | Extreme Values |
|---|---|---|---|---|---|---|---|
| Employment Intro Scene 7 | [video and audio] | Mr. Rivera | Good to see you. Let's get started. | | | | |
| Skip Alert Dialogue box | Are you sure you want to move on without answering this question?<br>Yes<br>No | Mr. Rivera | Are you sure you want to move on without answering this question?<br>Yes, or<br>No | If Yes, record -2 for skipped question | If Yes, go to next question.<br>If No, return to question.<br>ALL ASI-MV QUESTIONS GET THIS<br>.<br>.<br>. | | |
| No-Skip Alert Dialogue box | This question is important; so please try to answer.<br>Yes<br>No | Mr. Rivera | This question is important, so would you please try to choose an answer?<br>Yes<br>No | If No, record -2 for skipped question | If No, go to next question.<br>If Yes, return to question.<br>Add all -2 questions to Skipped<br>.<br>.<br>. | | |
| Extreme Alert Dialogue box | Is this the answer you want to give ___?<br>Yes<br>No | Mr. Rivera | Is this the answer you want to give?<br>Yes<br>No | If Yes, record answer to question | If No, return to question | | If Yes, add<br>.<br>.<br>. |
| Enter Prompt | none | Mr. Rivera | Remember, when you finish selecting your answer, click on the NEXT button to go to the next question. | None | | | |

FIG. 6P

| Question ID | Onscreen Text | Actor | Audio Recordings | ASI-MV Codes | Skip Logic | Consistency | Extreme Values |
|---|---|---|---|---|---|---|---|
| (ASIE001Y) (ASIE001M) | What is the highest level of education you have completed?<br><br>- 6th grade or less<br>- 7th grade<br>- 8th grade<br>- 9th grade<br>- 10th grade<br>- 11th grade<br>- Graduated high school or received a G.E.D.<br>- 1 year of college<br>- 2 years of college or an associate's degree<br>- 3 years of college<br>- 4 years of college or a bachelor's degree<br>- 1 year of graduate education<br>- 2 years of graduate education or a master's advanced degree<br>- 3 years of graduate education<br>- 4 years of graduate education or a Ph.D., M.D., or J.D | Mr. Rivera | What is the highest level of education you have completed?<br><br>• 6th grade or less<br>• 7th grade<br>• 8th grade<br>• 9th grade<br>• 10th grade<br>• 11th grade<br>• Graduated high school or received a G.E.D.<br>• 1 year of college<br>• 2 years of college or an associate's degree<br>• 3 years of college<br>• 4 years of college or a bachelor's degree<br>• 1 year of graduate education<br>• 2 years of graduate education or a master's advanced degree<br>• 3 years of graduate education<br>• 4 years of graduate education or a Ph.D., M.D. or J.D | ASIE001Y = coded as:<br>6 = 6th grade or less<br>7 = 7th<br>8 = 8th<br>9 = 9th<br>10 = 10th<br>11 = 11th<br>12 = 12th graduated HS or GED<br>13 = 1 year college<br>14 = 2 years college<br>15 = 3 years college<br>16 = 4 years college or BA/BS<br>17 = 1 year grad school<br>18 = 2 years grad school or Master's, advanced degree<br>19 = 3 years grad school<br>20 = 4 years grad school or PhD/MD/JD<br>ASIE001M always = 0 unless refused to answer (-2) | | | |

FIG. 6Q

| Question ID | Onscreen Text | Actor | Audio Recordings | ASI-MV Codes | Skip Logic | Consistency | Extreme Values |
|---|---|---|---|---|---|---|---|
| | Since the last time you took this ASI interview, what is the highest level of education you have completed?<br><br>- 6th grade or less<br>- 7th grade<br>- 8th grade<br>- 9th grade<br>- 10th grade<br>- 11th grade<br>- Graduated high school or received a G.E.D.<br>- 1 year of college<br>- 2 years of college or an associate's degree<br>- 3 years of college<br>- 4 years of college or a bachelor's degree<br>- 1 year of graduate education<br>- 2 years of graduate education or a master's advanced degree<br>- 3 years of graduate education<br>- 4 years of graduate education or a Ph.D., M.D., or J.D | | Since the last time you took this ASI interview, what is the highest level of education you have completed?<br><br>- 6th grade or less<br>- 7th grade<br>- 8th grade<br>- 9th grade<br>- 10th grade<br>- 11th grade<br>- Graduated high school or received a G.E.D.<br>- 1 year of college<br>- 2 years of college or an associate's degree<br>- 3 years of college<br>- 4 years of college or a bachelor's degree<br>- 1 year of graduate education<br>- 2 years of graduate education or a master's advanced degree<br>- 3 years of graduate education<br>- 4 years of graduate education or a Ph.D., M.D., or J.D | E1MOC = coded as:<br><br>6 = 6th grade or less<br>7 = 7th<br>8 = 8th<br>9 = 9th<br>10 = 10th<br>11 = 11th<br>12 = 12th graduated HS or GED<br>13 = 1 year college<br>14 = 2 years college<br>15 = 3 years college<br>16 = 4 years college or BA/BS<br>17 = 1 year grad school<br>18 = 2 years grad school or Master's, advanced degree<br>19 = 3 years grad school<br>20 = 4 years grad school or PhD/MD/JD | | | |
| (ASIE001Y)<br>(ASIE001M) | | Mr. Rivera | | | | | |
| F/up | | | | | | | |

FIG. 6R

| Question ID | Onscreen Text | Actor | Audio Recordings | ASI-MV Codes | Skip Logic | Consistency | Extreme Values |
|---|---|---|---|---|---|---|---|
| (ASIE002) | In your lifetime, about how much formal training or technical education have you completed that was not part of your regular education. For example, training in a trade or skill.<br><br>Year<br>Month<br>Less than a month<br>None | Mr. Rivera | In your lifetime, about how much formal training or technical education have you completed that was not part of your regular education.<br><br>For example, training in a trade or skill.<br><br>If less than a month, click this button.<br><br>If None, click this button. | Year/month counter<br>So (year x12) + months = total months<br>-Coded as 3 digit (MAX value = AGE)<br>Less than 1 month = 1<br>0 = None | | | |
| (ASIE002) F/up | Since the last time you took this ASI interview, about how much formal training or technical education have you completed in your life that was not part of your regular education. For example, training in a trade or skill.<br><br>Year<br>Month<br>Less than a month<br>None | Mr. Rivera | Since the last time you took this ASI interview, about how much formal training or technical education have you completed in your life that was not part of your regular education. For example, training in a trade or skill.<br><br>If less than a month, click this button.<br><br>If None, click this button. | Year/month counter<br>So (year x12) + months = total months<br>-Coded as 3 digit (MAX value = AGE)<br>Less than 1 month = 1<br>0 = None | | | |

FIG. 6S

| Question ID | Onscreen Text | Actor | Audio Recordings | ASI-MV Codes | Skip Logic | Consistency | Extreme Values |
|---|---|---|---|---|---|---|---|
| (ASIE003) | Do you have a profession, trade or skill? [Side Bar] This means having special skills that you got through job training, an apprenticeship or internship, or classes and has nothing to do with whether or not you currently have a job. Yes No | Mr. Rivera | Do you have a profession, trade or skill? This means having special skills that you got through job training, an apprenticeship or internship, or classes and has nothing to do with whether or not you currently have a job. Click Yes or No. | 1 = Yes 0 = No | | | |
| (ASIE004) (Composite question) | Do you have a valid driver's license? Enter No if your license is expired or has been suspended or revoked. Yes No | Mr. Rivera | Do you have a valid driver's license? Enter No if your license is expired or has been suspended or revoked. Click Yes or No. | 1 = Yes 0 = No | If -2 (refused), show No-Skip Alert If no, skip to E5AZ | | |
| (ASIE005) (Composite question) | Do you own a car or have one that you can use when you like? Yes No | Mr. Rivera | Do you own a car or have one that you can use when you like? Click Yes or No. | 1 = Yes 0 = No -1 if skipped, recode -1 = 0 | If -2 (refused), show No-Skip Alert | | |
| E5AZ | Are other forms of transportation available to you? For example the bus, subway, or rides from family or friends. Yes No | Mr. Rivera | Are other forms of transportation available to you? For example the bus, subway, or rides from family or friends. Click Yes or No. | 1 = Yes 0 = No | | | |

FIG. 6T

| Question ID | Onscreen Text | Actor | Audio Recordings | ASI-MV Codes | Skip Logic | Consistency | Extreme Values |
|---|---|---|---|---|---|---|---|
| (ASIE006Y) (ASIE006M) | About how long was your longest full-time job? Full-time is over 35 hours per week. Year Month Never Worked Full-Time | Mr. Rivera | About how long was your longest full-time job? Full-time is over 35 hours per week. If you have Never worked full-time, click this button. | -Year/Month counter 0 = Never worked full time (MAX value = AGE) | | | |

FIG. 6U

| Question ID | Onscreen Text | Actor | Audio Recordings | ASI-MV Codes | Skip Logic | Consistency | Extreme Values |
|---|---|---|---|---|---|---|---|
| (ASIE007) | Which one best describes your occupation or job during the past 3 years?<br><br>Executive or Professional (doctor, lawyer, owner of a large business, higher executive)<br>Other Professional/Management (nurse, teacher, social worker, pharmacist)<br>Administrative/Technical (computer programmer, administrative personnel, manager, owner of a small business)<br>Clerical/Sales (bank teller, bookkeeper, secretary, clerk, computer operator)<br>Skilled Manual (plumber, electrician, barber, chef, machinist, mechanic, police officer, painter)<br>Semi-Manual (bartender, bus driver, hospital aide, waiter, machine operator)<br>●<br>●<br>● | Mr. Rivera | Which one best describes your occupation or job during the past 3 years?<br>- Executive or Professional like a doctor, lawyer, owner of a large business, or higher executive<br>- Other Professional or Management like a nurse, teacher, social worker, or pharmacist<br>- Administrative or Technical like a computer programmer, administrative personnel, manager, or owner of a small business<br>- Clerical or Sales like a bank teller, bookkeeper, secretary, clerk, or computer operator<br>- Skilled Manual like a plumber, electrician, barber, chef, machinist, mechanic, police officer, or painter<br>- Semi-Manual like a bartender, bus driver, hospital aide, waiter, or machine operator<br>- Other Manual like a janitor or construction helper<br>- Homemaker<br>- Student<br>- Disabled<br>- No Occupation<br>- Did not work for pay at all in the past 3 years | 1 = Executive<br>2 = Other Professional<br>3 = Administrative<br>4 = Clerical/Sales<br>5 = Skilled Manual<br>6 = Semi Skilled<br>7 = Unskilled<br>8 = Homemaker<br>9 = Student<br>10=Disabled<br>11 = No occupation<br>12 = Didn't work for pay in the past 3 years<br><br>NOTE: for research database??<br>0 = Disabled recoded as 0<br><br>11=no occupation recoded as 9<br><br>12=Didn't work for pay in last 3 years recoded as 7 | | | |

FIG. 6V

| Question ID | Onscreen Text | Actor | Audio Recordings | ASI-MV Codes | Skip Logic | Consistency | Extreme Values |
|---|---|---|---|---|---|---|---|
| (ASIE007) F/up | Which one best describes your occupation or job since the last time you took this ASI interview? Executive or Professional (doctor, lawyer, owner of a large business, higher executive) Other Professional/Management (nurse, teacher, social worker, pharmacist) Administrative/Technical (computer programmer, administrative personnel, manager, owner of a small business) Clerical/Sales (bank teller, bookkeeper, secretary, clerk, computer operator) Skilled Manual (plumber, electrician, barber, chef, machinist, mechanic, police officer, painter) Semi-Manual (bartender, bus driver, hospital aide, waiter, ... | Mr. Rivera | Which one best describes your occupation or job since the last time you took this ASI interview? - Executive or Professional like a doctor, lawyer, owner of a large business, or higher executive - Other Professional or Management like a nurse, teacher, social worker, or pharmacist - Administrative or Technical like a computer programmer, administrative personnel, manager, or owner of a small business - Clerical or Sales like a bank teller, bookkeeper, secretary, clerk, or computer operator - Skilled Manual like a plumber, electrician, barber, chef, machinist, mechanic, police officer, or painter - Semi-Manual like a bartender, bus driver, hospital aide, waiter, or machine operator - Other Manual like a janitor or construction helper - Homemaker - Student - Disabled - No Occupation - Did not work for pay at all in the past 3 years | 1 = Executive 2 = Other Professional 3 = Administrative 4 = Clerical/Sales 5 = Skilled Manual 6 = Semi Skilled 7 = Unskilled 8 = Homemaker 9 = Student 10=Disabled 11 = No occupation 12 = Didn't work for pay in the past 3 years NOTE: for research database?? 0 = Disabled recoded as 0 11=no occupation recoded as 9 12=Didn't work for pay in last 3 years recoded as 7 | | | |
| ASI-MV5 MainScript NAVIPPRO | | | | | | | |

FIG. 6W

| Question ID | Onscreen Text | Actor | Audio Recordings | ASI-MV Codes | Skip Logic | Consistency | Extreme Values |
|---|---|---|---|---|---|---|---|
| (ASIE008) | Do you regularly receive financial support from family, friends, or other people? Financial support could include money, housing or food, alimony and child support. Yes No | Mr. Rivera | Do you regularly receive financial support from family, friends, or other people? Financial support could include money, housing or food, alimony and child support. Click Yes or No. | 1 = Yes 0 = No | If ASIE008 = 0, go to ASOE010 If ASIE008=1, go to ASIE009 | | |
| (ASIE009) | Does the financial support or money you receive from friends, family or other people make up most of your support? Yes No | Mr. Rivera | Does the financial support or money you receive from friends, family or other people make up most of your support? Click Yes or No. | 1 = Yes 0 = No | If skipped (b/c E08 = 0), code as (-1) | | |
| (ASIE010) | Which one best describes your employment situation for most of the past 3 years? Full-Time (35+ hours per week) Part-Time (regular hours) Part-Time (irregular hours) Student Homemaker Military Service Retired Disabled Unemployed In a prison or a hospital | Mr. Rivera | Which one best describes your employment situation for most of the past 3 years? • Full-Time (35+ hours per week) • Part-Time (regular hours) • Part-Time (irregular hours) • Student • Homemaker • Military Service • Retired • Disabled • Unemployed • In a prison or a hospital | 1 = Full time 2 = Part time 3 = Part time (irregular hours) 4 = Student 9 = homemaker 5 = Military Service 6 = Retired 10 = Disabled 7 = Unemployed 8 = In prison or hospital | | If ASIE006 = 0 and ASIE010 = 1, Consistency Alert If no: FLAG (if they don't change it, accept answer and add both questions and . . . | |

FIG. 6X

| Question ID | Onscreen Text | Actor | Audio Recordings | ASI-MV Codes | Skip Logic | Consistency | Extreme Values |
|---|---|---|---|---|---|---|---|
| (ASiE011) (Composite question) | In the past 30 days, about how many days did you receive Public Assistance, Welfare or food stamps? [Side bar] Include under the table work, paid sick days, and vacation days. Days None | Mr. Rivera | In the past 30 days, about how many days did you work for pay? Include under the table work, paid sick days, and vacation days. If None, click this button. | Answer coded as 2 digit variable (30 days) (MAX 30) 0 = None | if E11 = 0, go to E13 if E11>0, go to E12 If -2 (refused), show No-Skip Alert | | |
| (ASiE012) (Composite question) | In the past 30 days, about how much money did you receive in take home pay? Include money received under the table. Days None | Mr. Rivera | In the past 30 days, about how much money did you receive in take home pay? Include money received under the table. If None, click this button. | Answer coded as 5 digit variable 0 = None | -if skipped (b/c) E11 = 0, this question should be coded as 0 If -2 (refused), show No-Skip Alert | | |
| (ASiE013) | In the past 30 days, about how much money did you receive from unemployment compensation? Days None | Mr. Rivera | In the past 30 days, about how much money did you receive from unemployment compensation? If None, click this button. | Answer coded as 5 digit variable 0 = None | | | if ASIE013 >1000, Extreme . . . |
| (ASiE014) | In the past 30 days, about how much money did you receive Public Assistance, Welfare or food stamps? | Mr. Rivera | In the past 30 days, about how much money did you receive Public Assistance, Welfare or food stamps? Do not include money from Social | Answer coded as 5 digit variable 0 = None | | | if ASIE014 >1000, Extreme Alert and if . . . |

FIG. 6Y

| Question ID | Onscreen Text | Actor | Audio Recordings | ASI-MV Codes | Skip Logic | Consistency | Extreme Values |
|---|---|---|---|---|---|---|---|
| (ASIE015) | In the past 30 days, how much money did you receive from any Pension, Disability, Worker's Compensation, Social Security or Veteran's Benefit?<br><br>None | Mr. Rivera | In the past 30 days, how much money did you receive from any Pension, Disability, Worker's Compensation, Social Security or Veteran's Benefit?<br><br>If None, click this button. | Answer coded as 5 digit variable<br><br>0 = None | | If ASIM005 = 1 & ASIE015 = 0, Consistency Alert<br>or<br>if ASIP003 = 1 & ASIE015 = 0, Consistency Alert | If ASIE015 > 2000, Extreme Alert and if not changed, add question and answer to the Extreme Values Report |
| (ASIE016) | In the past 30 days, how much money did you borrow or receive from a significant other, family or friends? Include cash received from loans or child support or alimony. Do not include housing and food provided.<br><br>None | Mr. Rivera | In the past 30 days, how much money did you borrow or receive from a significant other, family or friends? Include cash received from loans or child support or alimony. Do not include housing and food provided.<br><br>If None, click this button. | Answer coded as 5 digit variable<br><br>0 = None<br>Research database: This should be added to ASIE016 to yield answer to ASIE016 | | | |
| (ASIE017)<br>(Composite question:<br>LEGAL) | In the past 30 days, how much money did you borrow or receive from illegal sources such as drug sales, stealing, fencing, gambling, prostitution, etc.?<br>None | Mr. Rivera | In the past 30 days, how much money did you borrow or receive from illegal sources such as drug sales, stealing, fencing, gambling, prostitution, etc.?<br><br>If None, click this button. | Answer coded as 5 digit variable<br><br>0 = None | If -2 (refused), show No-Skip Alert | | |

FIG. 6Z

| Question ID | Onscreen Text | Actor | Audio Recordings | ASI-MV Codes | Skip Logic | Consistency | Extreme Values |
|---|---|---|---|---|---|---|---|
| (ASIE016B) | In the past 30 days, how much money did you receive from other sources?<br>[Side Bar]<br>For example, investment income, lottery, tax refunds, or inheritance.<br>None | Mr. Rivera | In the past 30 days, how much money did you receive from other sources?<br>For example, investment income, lottery, tax refunds, or inheritance.<br>If None, click this button. | Answer coded as 5 digit variable<br>0 = None<br>Research database. This should be added to ASIE016 to yield answer to ASIE016 | | | |
| (ASIE018) | How many people depend on you for the majority of their food, shelter, or financial support?<br>[Side Bar]<br>Please include support given to a non-working spouse or significant other, ex-spouse, children, or parents. Do not include yourself.<br>2 digit counter up to 20<br>None | Mr. Rivera | How many people depend on you for the majority of their food, shelter, or financial support?<br>Please include support given to a non-working spouse or significant other, ex-spouse, children, or parents.<br>Do not include yourself.<br>If None, click this button. | Answer coded as 2 digit variable<br>0 = None | | | If ASIE018 > 10, Extreme Alert and if not changed, add question and answer to the Extreme Values Report |
| (ASIE019B) | In the past 30 days, about how many days did you seriously look for work?<br>Days<br>None | Mr. Rivera | In the past 30 days, about how many days did you seriously look for work?<br>If None, click this button. | Answer coded as 2 digit variable (MAX 30)<br>0 = None | MAKE SURE TO ADD ASIE019 AND ASIE019B | | |

FIG. 6AA

| Question ID | Onscreen Text | Actor | Audio Recordings | ASI-MV Codes | Skip Logic | Consistency | Extreme Values |
|---|---|---|---|---|---|---|---|
| (ASiE019) | In the past 30 days, about how many days have you had problems that affected your work? [Side bar] For example, missing days, not completing tasks, difficulties with co-workers, really disliking your job, or fear of possible lay off. Days None | Mr. Rivera | In the past 30 days, about how many days have you had problems that affected your work? For example, missing days, not completing tasks, difficulties with co-workers, really disliking your job, or fear of possible lay off. If None, click this button. | Answer coded as 2 digit variable (MAX = 30) 0 = None | (MAKE SURE TO ADD ASIE019 AND ASIE019B TO MAKE ASIE019 BEFORE USING IN CALCULATION) (MAX 30 AFTER ADDITION) | | |
| (ASiE020) | In the past 30 days, how troubled or bothered have you been by difficulties in looking for work or by problems at work? Not at all Slightly Moderately Considerably Extremely | Mr. Rivera | In the past 30 days, how troubled or bothered have you been by difficulties in looking for work or by problems at work? • Not at all • Slightly • Moderately • Considerably • Extremely | 0 = Not at all 1 = Slightly 2 = Moderately 3 = Considerably 4 = Extremely | | | |
| (ASiE021) | How important is it to you now that you receive help or counseling for employment problems, such as literacy or reading programs, job training or job readiness training? • • | Mr. Rivera | How important is it to you now that you receive help or counseling for employment problems, such as literacy or reading programs, job training or job readiness training? • Not at all • • | 0 = Not at all 1 = Slightly 2 = Moderately 3 = Considerably 4 = Extremely | | | |

FIG. 6BB

| Question ID | Onscreen Text | Actor | Audio Recordings | ASI-MV Codes | Skip Logic | Consistency | Extreme Values |
|---|---|---|---|---|---|---|---|
| (ASIE022) | | | | (Calculated Variable) Employment Severity Rating | (MAKE SURE TO ADD ASIE019 + ASIE019B = ASIE019 [MAX = 30] BEFORE CALCULATING) COMPUTE empsev = ASIE019 + ASIE011. | | |
| CONPEMP (Calculated Variable) | | | | Employment Composite Score (.000-1.000) | VARIABLES IN THE DATABASE asie012 : How much money did you make in the past 30 days asie004 : Do you have a valid drivers license asie005 : Do you have a car you can use asie011 : How many days did you work for pay | | |
| | | Mr. Rivera | That does it for me! Have a nice day. | | | | |
| | | George | This is probably easier than you thought! Your next interview is right over there. Mr. Fielder needs to ask you a few questions about your alcohol and drug use. Click on his door to get started. | | | | |
| Drug and Alcohol Section | | | | | | | |
| | | Mr. Fielder | Hello. I need to ask you some questions about your use of drugs and alcohol. Let's begin. | | | | |

FIG. 6CC

| Question ID | Onscreen Text | Actor | Audio Recordings | ASI-MV Codes | Skip Logic | Consistency | Extreme Values |
|---|---|---|---|---|---|---|---|
| Skip Alert Dialogue box | Are you sure you want to move on without answering this question? Yes No | Mr. Fielder | Are you sure you want to move on without answering this question? Yes, or No | If Yes, record -2 for skipped question | If Yes, go to next question. If No, return to question. ALL ASI-MV QUESTIONS GET THIS • • • | | |
| No-Skip Alert Dialogue box | This question is important, so please try to answer. Yes No | Mr. Fielder | This question is important, so would you please try to choose an answer? Yes No | If No, record -2 for skipped question | If No, go to next question. If Yes, return to question. Add all -2 questions to Skipped • • • | | |
| Extreme Alert Dialogue box | Is this the answer you want to give _____? Yes No | Mr. Fielder | Is this the answer you want to give? Yes No | If Yes, record answer to question | If No, return to question | | If Yes, add • • • |
| Enter Prompt | none | Mr. Fielder | Remember, when you finish selecting your answer, click on the NEXT button to go to the next question. | none | | | |

FIG. 6DD

| Question ID | Onscreen Text | Actor | Audio Recordings | ASI-MV Codes | Skip Logic | Consistency | Extreme Values |
|---|---|---|---|---|---|---|---|
| (ASID001D) | In the past 30 days, about how many days did you drink any alcohol?<br><br>[2 digit counter]<br>Days<br>None | Mr. Fielder | In the past 30 days, about how many days did you drink any alcohol?<br><br>Remember, clicking and holding down the arrows will speed the counter up and down.<br><br>If None, click the button. | Coded as 2 digit variable<br><br>(MAX = 30)<br><br>0 = None | If ASID001D=0, go to ASID001Y, If ASID001D >0, go to ASID002D<br><br>If -2 (refused), show No-Skip Alert | If ASID001D > 0 and ASID015B = 0 or 2 Consistency Alert. If no: FLAG (if they don't change it. . . . | |
| (ASID002D)<br>(Composite question) | On how many of these days did you drink at least 5 drinks?<br><br>[2 digit counter]<br>Days<br>None | Mr. Fielder | On how many of these days did you drink at least 5 drinks?<br><br>If None, click the button. | Coded as 2 digit variable<br><br>0 = None<br><br>(-1 = 0) | - if skipped (b/c ASID001D = 0) codes as 0<br><br>If -2 (refused), show No-Skip Alert | If ASID002D > 0 and ASID015B = 0 or 2 Consistency Alert. If no: FLAG (if they don't change it. . . . | |
| (ASID023)<br>(Composite question) | In the past 30 days, how much money have you spent on alcohol?<br><br>None | Mr. Fielder | In the past 30 days, how much money have you spent on alcohol?<br><br>If None, click the button. | Coded as 5 digit variable<br><br>0 = None<br><br>(-1 = 0) | - if skipped (b/c ASID001D = 0) codes as 0<br><br>If -2 (refused), show No-Skip Alert | | If ASID023 > 700, Extreme Alert and if . . . |

FIG. 6EE

| Question ID | Onscreen Text | Actor | Audio Recordings | ASI-MV Codes | Skip Logic | Consistency | Extreme Values |
|---|---|---|---|---|---|---|---|
| (ASID001Y) | Estimate the total number of years that you drank any alcohol (beer, wine, liquor) on a regular basis, at least 3 days a week.<br><br>Years [2 digit counter]<br><br>If less than 1 year choose one of the following:<br><br>Between 6 months and 1 year<br>Less than 6 months<br>None | Mr. Fielder | Estimate the total number of years that you drank any alcohol (beer, wine, liquor) on a regular basis, at least 3 days a week.<br><br>If less than 1 year choose one of the following:<br><br>• Between 6 months and 1 year<br>• Less than 6 months<br>• None | Coded as 2 digit variable (years)<br><br>.7 = Between 6 mos and 1 year<br>.5 = Less than 6 mos<br>0 = None<br><br>(MAX value = AGE) | | | |
| (ASID002Y) | Estimate the total number of years that you have had at least 5 drinks a day on a regular basis, at least 3 days a week.<br><br>Years [2 digit counter]<br><br>If less than 1 year choose one of the following:<br><br>Between 6 months and 1 year<br>Less than 6 months<br>None | Mr. Fielder | Estimate the total number of years that you have had at least 5 drinks a day on a regular basis, at least 3 days a week.<br><br>If less than 1 year choose one of the following:<br><br>• Between 6 months and 1 year<br>• Less than 6 months<br>• None | Coded as 2 digit variable (years)<br><br>.7 = Between 6 mos and 1 year<br>.5 = Less than 6 mos<br>0 = None<br><br>(MAX value = AGE) | | | |

FIG. 6FF

| Question ID | Onscreen Text | Actor | Audio Recordings | ASI-MV Codes | Skip Logic | Consistency | Extreme Values |
|---|---|---|---|---|---|---|---|
| ASIDALLA ASIDALLB ASIDALLC ASIDALLD ASIDALLE ASIDALLF ASIDALLG ASIDALLH ASIDALLI ASIDALLJ ASIDALLK | Which of the following substances have you used in your lifetime? Please select all that apply.<br>-Heroin (A)<br>-Methadone or LAAM (B)<br>-Other opiates or painkillers like morphine, darvon, percodan, vicodin, talwin, dilaudid, or codeine (C)<br>-Barbiturates like seconal, tuinol, Nembutal, Phenobarbital and fiorinal, (also known as barbs, reds and yellows) (D)<br>-Sedatives, tranquilizers or sleeping pills like valium, Librium, Xanax, Ativan, ambien, serax, and Quaaludes (also known as downers or tranks) (E)<br>-Cocaine or Crack (F)<br>-Amphetamines or uppers like crank, ice, meth, Ritalin, Dexedrine, speed, or other stimulants (G)<br>-Marijuana or hashish (H)<br>. . .<br>. . . | Mr. Fielder | Which of the following substances have you used in your lifetime?<br><br>Please select all that apply.<br><br>• Heroin<br>• Methadone or LAAM<br>• Other opiates or painkillers like morphine, darvon, percodan, vicodin, talwin, dilaudid, or codeine<br>• Barbiturates like seconal, tuinol, Nembutal, Phenobarbital and fiorinal, (also known as barbs, reds and yellows)<br>• Sedatives, tranquilizers or sleeping pills like valium, Librium, Xanax, Ativan, ambien, serax, and Quaaludes (also known as downers or tranks)<br>• Cocaine or Crack<br>• Amphetamines or uppers like crank, ice, meth, Ritalin, Dexedrine, speed, or other stimulants<br>• Marijuana or hashish<br>• Hallucinogens like LSD or acid, PCP or angel dust, mescaline, or mushrooms<br>• Inhalants like glue, gasoline, nitrous oxide, whippets, or poppers<br>• None | Each variable will be given a separate value<br><br>1 = Yes/Selected<br>0 = No/Not selected<br><br>ASIDALLA Heroin<br>ASIDALLB Methadone<br>ASIDALLC Other opiates<br>ASIDALLD Barbiturates<br>ASIDALLE Sedatives<br>ASIDALLF Cocaine<br>ASIDALLG Amphetamines<br>ASIDALLH Marijuana<br>ASIDALLI Hallucinogens<br>ASIDALLJ Inhalants<br>ASIDALLK None | If ASIDALLA = 1, enable ASID003D<br>If ASIDALLB = 1, enable ASID004D<br>If ASIDALLC = 1, enable ASID005D<br>If ASIDALLC = 0, enable OP30<br>If ASIDALLD = 1, enable ASIDO06D<br>If ASIDALLE = 1, enable ASID007D<br>If ASIDALLF = 1, enable ASID008D<br>If ASIDALLG = 1, enable ASID009D<br>If ASIDALLH = 1, enable ASID010D<br>If ASIDALLI = 1,<br>. . .<br>. . . | | |

FIG. 6GG

| Question ID | Onscreen Text | Actor | Audio Recordings | ASI-MV Codes | Skip Logic | Consistency | Extreme Values |
|---|---|---|---|---|---|---|---|
| (ASID003D) (Composite question) | In the past 30 days, estimate how many days you used heroin.<br><br>Days<br>None | Mr. Fielder | In the past 30 days, estimate how many days you used heroin.<br><br>If None, click this button. | Coded as 2 digit variable<br>(MAX = 30)<br><br>0 = None<br><br>(-1 = 0) | - if skipped (b/c ASIDALLA = 0) codes as 0<br><br>If -2 (refused), show No-Skip Alert | If ASID003D > 0 and ASID015B = 0 or 2 . . . | |
| (ASID005Y) | Estimate the total number of years that you used heroin at least 3 days a week.<br><br>Years [2 digit counter]<br>If less than 1 year choose one of the following:<br>Between 6 months and 1 year<br>Less than 6 months<br>Tried it a few times | Mr. Fielder | Estimate the total number of years that you used heroin at least 3 days a week.<br><br>If less than 1 year choose one of the following:<br><br>• Between 6 months and 1 year<br>• Less than 6 months<br>• Tried it a few times | Coded as 2 digit variable<br>.7 = 6 mos -1 year<br>.5 = Less than 6 mos<br>0 = Tried it a few times<br><br>(-1 = 0)<br><br>(MAX value = AGE) | - if skipped (b/c ASIDALLA = 0) codes as 0 | | |
| D3c<br><br>D3R1<br>D3R2<br>D3R3<br>D3R4<br>D3R5 | How have you usually used heroin?<br>Please select all that apply.<br><br>Swallowed<br>Snorted/Sniffed<br>Smoked<br>Injected in skin or muscle<br>Injected in vein | Mr. Fielder | How have you usually used heroin?<br>Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br>D3R1 = Swallowed<br>. . . | - If skipped (b/c prev questions are 0 ) code as -1 | | |

FIG. 6HH

| Question ID | Actor | Onscreen Text | Audio Recordings | ASI-MV Codes | Skip Logic | Consistency | Extreme Values |
|---|---|---|---|---|---|---|---|
| (ASID004D)<br><br>(Composite question) | Mr. Fielder | In the past 30 days, estimate how many days you used methadone or LAAM. Include days you received methadone or LAAM at a treatment program.<br><br>Days [2 digit counter]<br>None | In the past 30 days, estimate how many days you used methadone or LAAM.<br><br>Include days you received methadone or LAAM at a treatment program.<br><br>If None, click this button. | Coded as 2 digit variable<br>(MAX = 30)<br><br>0 = None<br><br>(-1 = 0) | - if skipped (b/c ASIDALLB = 0) codes as 0<br><br>if -2 (refused), show No-Skip Alert | If ASID004D > 0 and ASID015B = 0 or 2<br>Consistency Alert<br><br>If no: FLAG (if they don't change it, accept answer | |
| (ASID004Y) | Mr. Fielder | Estimate the total number of years that you used methadone or LAAM at least 3 days a week. Include all use, whether you received it as part of a treatment program or not.<br><br>Years [2 digit counter]<br><br>If less than 1 year choose one of the following:<br>Between 6 months and 1 year<br>Less than 6 months<br>Tried it a few times | Estimate the total number of years that you used methadone or LAAM at least 3 days a week. Include all use, whether you received it as part of a treatment program or not.<br><br>If less than 1 year choose one of the following:<br>• Between 6 months and 1 year<br>• Less than 6 months<br>• Tried it a few times | Coded as 2 digit variable<br><br>.7 = 6 mos -1 year<br>.5 = Less than 6 mos<br>0 = Tried it a few times<br><br>(-1 = 0)<br><br>(MAX value = AGE) | - if skipped (b/c ASIDALLB = 0) codes as 0 | | |

FIG. 6II

| Question ID | Onscreen Text | Actor | Audio Recordings | ASI-MV Codes | Skip Logic | Consistency | Extreme Values |
|---|---|---|---|---|---|---|---|
| D4c | How have you usually used methadone or LAAM? | Mr. Fielder | How have you usually used methadone or LAAM? | 1 = Each variable will be given a separate value | - If skipped (b/c prev questions are 0 ) code as -1 | | |
| D4R1<br>D4R2<br>D4R3<br>D4R4<br>D4R5 | Please select all that apply.<br><br>Swallowed<br>Snorted/Sniffed<br>Smoked<br>Injected in skin or muscle<br>Injected in vein | | Please select all that apply.<br><br>• Swallowed<br>• Snorted/Sniffed<br>• Smoked<br>• Injected in the skin or in the muscle<br>• Injected into a vein | 1 = Yes/Selected<br>0 = No/Not selected<br><br>D4R1 = Swallowed<br>•<br>•<br>• | After ASID004R is answered, go to screen OP4 (do all OP4 questions—OP 4A & OP4B + •<br>•<br>• | | |
| OP30 | Have you used any prescription opiate pain medication in the past 30 days, for any reason?<br><br>(This includes medications like Oxycontin, Morphine, Vicodin, Codeine, Percocet, Tylox, Percodan, Lorcet, Lortab, and Norco. Do not include non-opiate pain medication such as Celebrex, Motrin, Tylenol and Aleve)<br><br>- Yes<br>- No | Mr. Fielder | Have you used any prescription opiate pain medication in the past 30 days, for any reason?<br><br>(This includes medications like Oxycontin, Morphine, Vicodin, Codeine, Percocet, Tylox, Percodan, Lorcet, Lortab, and Norco. Do not include non-opiate pain medication such as Celebrex, Motrin, Tylenol and Aleve)<br><br>- Yes<br>- No | 1 = Yes<br>0 = No | if OP30=1, go to OPintro<br>if OP30=0, go back to next chosen drug from ASID003-ASID012 | | |

FIG. 6JJ

| Question ID | Onscreen Text | Actor | Audio Recordings | ASI-MV Codes | Skip Logic | Consistency | Extreme Values |
|---|---|---|---|---|---|---|---|
| (ASID005D) | In the past 30 days, estimate how many days you used opiates or painkillers (other than heroin or methadone/LAAM).<br>Please include prescribed and non-prescribed use.<br>Examples of opiates or painkillers include: morphine, darvon, darvocet, talwin, dilaudid, or codeine.<br>Days<br>None | Mr. Fielder | In the past 30 days, estimate how many days you used opiates or painkillers (other than heroin or methadone/LAAM).<br>Please include prescribed and non-prescribed use.<br>Examples of opiates or painkillers include: morphine, darvon, darvocet, talwin, dilaudid, or codeine.<br>If None, click this button. | Coded as 2 digit variable<br>(MAX = 30)<br>0 = None<br>(-1 = 0) | If ASID005D = 0, enable OP30<br>- if skipped (b/c ASIDALLC = 0) codes as 0 | If ASID005D > 0 and ASID015B = 0 or 2 Consistency Alert<br>If no: FLAG (if they don't change it, accept answer . . . | |
| (ASID005Y) | Estimate the total number of years that you used opiates or painkillers (other than heroin or methadone/LAAM) at least 3 days a week.<br>Please include prescribed and non-prescribed use.<br>Years [2 digit counter]<br>If less than 1 year choose one of the following:<br>Between 6 months and 1 year<br>Less than 6 months<br>Tried it a few times | Mr. Fielder | Estimate the total number of years that you used opiates or painkillers (other than heroin or methadone/LAAM) at least 3 days a week.<br>Please include prescribed and non-prescribed use.<br>If less than 1 year choose one of the following:<br>• Between 6 months and 1 year<br>• Less than 6 months<br>• Tried it a few times | Coded as 2 digit variable<br>.7 = 6 mos -1 year<br>.5 = Less than 6 mos<br>0 = Tried it a few times<br>(-1 = 0)<br>(MAX value = AGE) | - if skipped (b/c ASIDALLC = 0) codes as 0 | | |

FIG. 6KK

| Question ID | Onscreen Text | Actor | Audio Recordings | ASI-MV Codes | Skip Logic | Consistency | Extreme Values |
|---|---|---|---|---|---|---|---|
| D5c | How have you usually used opiates or painkillers (other than heroin or methedone/LAAM)? | Mr. Fielder | How have you usually used opiates or painkillers (other than heroin or methedone/LAAM)? | Each variable will be given a separate value | | | |
| D5R1 D5R2 D5R3 D5R4 D5R5 | Please include prescribed and non-prescribed use. Please select all that apply. Swallowed Snorted/Sniffed Smoked Injected in skin or muscle Injected in vein | | Please include prescribed and non-prescribed use. Please select all that apply. • Swallowed • Snorted/Sniffed • Smoked • Injected in the skin or in the muscle • Injected into a vein | 1 = Yes/Selected 0 = No/Not selected D5R1 = Swallowed D5R2 = Snorted/Sniffed D5R3 = Smoked D5R4 = non-IV injection D5R5 = IV injection | - if skipped (b/c prev questions are 0 ) code as -1 | | |
| OPintro | The next several screens show you pictures of different prescription opiate or pain medications. Please look at these screens and click on any of the medications you have taken in the past 30 days. | Mr. Fielder | The next several screens show you pictures of different prescription opiate or pain medications. Please look at these screens and click on any of the medications you have taken in the past 30 days. | | Enabled if: M4E = 1 OR ASID005D > 0 OR OP30=1 | | |

FIG. 6LL

| Question ID | Onscreen Text | Actor | Audio Recordings | ASI-MV Codes | Skip Logic | Consistency | Extreme Values |
|---|---|---|---|---|---|---|---|
| OP1 (no screen =1)<br><br>OP1A = Oxycontin<br>OP1B = Oxycodone ER<br>OP1C = Oxycodone ER<br>OP1D = none | If you have taken Oxycontin or Oxycodone ER in the past 30 days please select the appropriat e boxes below.<br><br>Remember to only select the boxes if you recognize the picture of the medications you used. These medications are also called OC, Ox, Oxy, Oxy IR, Blue, Kicker, Oxycotton, 40's (40mg tablet), 80's (80 mg tablet).<br><br>[IMAGE BOXES]<br>Oxycontin<br>Oxycodone ER<br>Oxycodone ER<br>none | Mr. Fielder | If you have taken Oxycontin or Oxycodone ER in the past 30 days please select the appropriate boxes below.<br><br>If none, click here.<br><br>Remember to only select the boxes if you recognize the picture of the medication you used. These medications are also called OC, Ox, Oxy, Oxy IR, Blue, Hillbilly heroin, Kicker, Oxycotton, 40's (40mg tablet), 80's (80 mg tablet).<br><br>Oxycontin<br>Oxycodone ER<br>Oxycodone ER<br>none | Each variable will be given a separate value<br><br>1 = Yes/Selected<br>0 = No/Not selected<br><br>OP1A = Oxycontin<br>OP1B = Oxycodone ER (Endo)<br>OP1C = Oxycodone ER (Teva)<br>OP1D = none | If OP1A = 1, enable OPRATE and go to OP1A30<br>If OP1B = 1, enable OPRATE and go to OP1B30<br>If OP1C = 1, enable OPRATE and go to OP1C30<br>Id OP1D = . | | |
| OP1A30 | How many days in the past 30 days did you useOxycontin in a way not prescribed by your doctor?<br><br>That is using it for how it made you feel and not to help with pain.<br><br>Days [2 digit counter]<br>None | | How many days in the past 30 days did you use Oxycontin in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | If skipped (b/c OP1A = 0) codes as 0 | | |

FIG. 6MM

| Question ID | Onscreen Text | Actor | Audio Recordings | ASI-MV Codes | Skip Logic | Consistency | Extreme Values |
|---|---|---|---|---|---|---|---|
| OP1AR1<br>OP1AR2<br>OP1AR3<br>OP1AR4<br>OP1AR5 | How have you usually used Oxycontin? Please click on all that apply.<br><br>Swallowed<br>Snorted/Sniffed<br>Smoked<br>Injected in skin or muscle<br>Injected in vein | | How have you usually used Oxycontin? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP1AR1 = Swallowed<br>•<br>•<br>• | | | |
| OP1AW1<br>OP1AW2<br>OP1AW3<br>OP1AW4<br>OP1AW5<br>OP1AW6<br>OP1AW7<br>OP1AW8 | Where did you get the Oxycontin? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Oxycontin? Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP1AW1 = Own prescriptions<br>OP1AW2 = More than one Doctor<br>OP1AW3 = Internet shopping<br>OP1AW4 = Family<br>OP1A5 = A dealer<br>OP1AW6 = Forgery<br>OP1AW7 = Stealing<br>OP1AW8 = Other | | | |

FIG. 6NN

| Question ID | Onscreen Text | Actor | Audio Recordings | ASI-MV Codes | Skip Logic | Consistency | Extreme Values |
|---|---|---|---|---|---|---|---|
| OP1B30 | How many days in the past 30 days did you use Oxycodone ER in a way not prescribed by your doctor?<br><br>That is using it for how it made you feel and not to help with pain.<br><br>Days [2 digit counter]<br>None<br><br>[NOTE: INCLUDE IMAGE OF OXYCODONE ER (ENDO)] | | How many days in the past 30 days did you use Oxycodone ER in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP1B = 0) codes as 0 | | |
| OP1BR1<br>OP1BR2<br>OP1BR3<br>OP1BR4<br>OP1BR5 | How have you usually used Oxycodone ER? Please select all that apply.<br><br>Swallowed<br>Snorted/Sniffed<br>Smoked<br>Injected in skin or muscle<br>Injected in vein<br><br>[NOTE: INCLUDE IMAGE OF OXYCODONE ER (ENDO)] | | How have you usually used Oxycodone ER? Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP1BR1 = Swallowed<br>OP1BR2 = Snorted/Sniffed<br>OP1BR3 = Smoked<br>OP1BR4 = non-IV Injection<br>OP1BR5 = IV injection | | | |

FIG. 6OO

| Question ID | Onscreen Text | Actor | Audio Recordings | ASI-MV Codes | Skip Logic | Consistency | Extreme Values |
|---|---|---|---|---|---|---|---|
| <br>OP1BW1<br>OP1BW2<br>OP1BW3<br>OP1BW4<br>OP1BW5<br>OP1BW6<br>OP1BW7<br>OP1BW8 | Where did you get the Oxycodone ER ?<br>Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other<br>[NOTE: INCLUDE IMAGE OF OXYCODONE ER (ENDO)] | | Where did you get the Oxycodone ER? Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP1BW1 = Own prescriptions<br>OP1BW2 = More than one Doctor<br>OP1BW3 = Internet shopping<br>OP1BW4 = Family<br>OP1BW5 = A dealer<br>OP1BW6 = Forgery<br>OP1BW7 = Stealing<br>OP1BW8 = Other | | | |

FIG. 6PP

| Question ID | Onscreen Text | Actor | Audio Recordings | ASI-MV Codes | Skip Logic | Consistency | Extreme Values |
|---|---|---|---|---|---|---|---|
| OP1C30 | How many days in the past 30 days did you use Oxycodone ER in a way not prescribed by your doctor?<br><br>That is using it for how it made you feel and not to help with pain.<br><br>Days [2 digit counter]<br>None<br>[NOTE: INCLUDE IMAGE OF OXYCODONE ER (TEVA)] | | How many days in the past 30 days did you use Oxycodone ER in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP1C = 0) codes as 0 | | |
| OP1CR1<br>OP1CR2<br>OP1CR3<br>OP1CR4<br>OP1CR5 | How have you usually used Oxycodone ER?<br>Please select all that apply.<br><br>Swallowed<br>Snorted/Sniffed<br>Smoked<br>injected in skin or muscle<br>injected in vein<br><br>[NOTE: INCLUDE IMAGE OF OXYCODONE ER (TEVA)] | | How have you usually used Oxycodone ER?<br>Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP1CR1 = Swallowed<br>OP1CR2 = Snorted/Sniffed<br>OP1CR3 = Smoked<br>OP1CR4 = non-IV Injection<br>OP1CR5 = IV injection | | | |

FIG. 6QQ

| Question ID | Onscreen Text | Actor | Audio Recordings | ASI-MV Codes | Skip Logic | Consistency | Extreme Values |
|---|---|---|---|---|---|---|---|
| OP1CW1<br>OP1CW2<br>OP1CW3<br>OP1CW4<br>OP1CW5<br>OP1CW6<br>OP1CW7<br>OP1CW8 | Where did you get the Oxycodone ER ? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other<br>[NOTE: INCLUDE IMAGE OF OXYCODONE ER (TEVA)] | | Where did you get the OxycodoneER? Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP1CW1 = Own prescriptions<br>OP1CW2 = More than one Doctor<br>OP1CW3 = Internet shopping<br>OP1CW4 = Family<br>OP1CW5 = A dealer<br>OP1CW6 = Forgery<br>OP1CW7 = Stealing<br>OP1CW8 = Other | | | |

FIG. 6RR

| Question ID | Onscreen Text | Actor | Audio Recordings | ASI-MV Codes | Skip Logic | Consistency | Extreme Values |
|---|---|---|---|---|---|---|---|
| OP2 (no screen =2) OP2A = Percocet OP2B = Tylox OP2C = Percodan OP2D = Combunox OP2E = Oxycodone IR OP2F = other oxycodone OP2G = none | If you have taken Percocet, Tylox, Percodan, Combunox, Oxycodone IR or other oxycodone in the past 30 days please select the appropriate boxes below. Remember to only select the boxes if you recognize the picture of the medications you used. These medications are also called Percs & Perkies. [IMAGE BOXES] Percocet ... ... | | If you have taken Percocet, Tylox, Percodan, Combunox, Oxycodone IR or other oxycodone in the past 30 days please select the appropriate boxes below. If none, click here. Remember to only select the boxes if you recognize the picture of the medications you used. These medications are also called Percs & Perkies. | Each variable will be given a separate value 1 = Yes/Selected 0 = No/Not selected OP2A = Percocet OP2B = Tylox OP2C = Percodan OP2D = Combunox OP2E = Oxycodone IR OP2F = other oxycodone OP2G = none | If OP2A = 1, enable OPRATE and go to OP2A30 If OP2B = 1, enable OPRATE and go to OP2B30 If OP2C = 1, enable OPRATE and go to ... ... | | |
| OP2A30 | How many days in the past 30 days did you usePercocet in a way not prescribed by your doctor? That is using it for how it made you feel and not to help with pain. Days [2 digit counter] None | | How many days in the past 30 days did you use Percocet in a way not prescribed by your doctor? That is using it for how it made you feel and not to help with pain. Please click on the up or down arrow on the counter to show the number of days - or if None, click here. | Coded as 2 digit variable (MAX = 30) 0 = None (-1 = 0) | if skipped (b/c OP2A = 0) codes as 0 | | |

FIG. 6SS

| Question ID | Onscreen Text | Actor | Audio Recordings | ASI-MV Codes | Skip Logic | Consistency | Extreme Values |
|---|---|---|---|---|---|---|---|
| OP2AR1<br>OP2AR2<br>OP2AR3<br>OP2AR4<br>OP2AR5 | How have you usually used Percocet? Please select all that apply.<br><br>- Swallowed<br>- Snorted/Sniffed<br>- Smoked<br>- Injected in skin or muscle<br>- Injected in vein | | How have you usually used Percocet? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP2AR1 = Swallowed<br>•<br>•<br>• | | | |
| OP2AW1<br>OP2AW2<br>OP2AW3<br>OP2AW4<br>OP2AW5<br>OP2AW6<br>OP2AW7<br>OP2AW8 | Where did you get the Percocet? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Percocet? Please click on all that apply:<br><br>- Your own prescriptions (from one Dr.)<br>- Multiple Doctors (from several Drs or emergency services)<br>- internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP2AW1 = Own prescriptions<br>OP2AW2 = More than one Doctor<br>OP2AW3 = internet shopping<br>OP2AW4 = Family<br>OP2AW5 = A dealer<br>OP2AW6 = Forgery<br>OP2AW7 = Stealing<br>OP2AW8 = Other | | | |

FIG. 6TT

| Question ID | Onscreen Text | Actor | Audio Recordings | ASI-MV Codes | Skip Logic | Consistency | Extreme Values |
|---|---|---|---|---|---|---|---|
| OP2B30 | How many days in the past 30 days did you use Tylox in a way not prescribed by your doctor? That is using it for how it made you feel and not to help with pain. Days [2 digit counter] None | | How many days in the past 30 days did you use Tylox in a way not prescribed by your doctor? That is using it for how it made you feel and not to help with pain. Please click on the up or down arrow on the counter to show the number of days - or if None, click here. | Coded as 2 digit variable (MAX = 30) 0 = None (-1 = 0) | If skipped (b/c OP2B = 0) codes as 0 | | |
| OP2BR1 OP2BR2 OP2BR3 OP2BR4 OP2BR5 | How have you usually used Tylox? Please select all that apply. Swallowed Snorted/Sniffed Smoked Injected in skin or muscle Injected in vein | | How have you usually used Tylox? Please select all that apply. • Swallowed • Snorted/Sniffed • Smoked • Injected in the skin or in the muscle • Injected into a vein | Each variable will be given a separate value 1 = Yes/Selected 0 = No/Not selected OP2BR1 = Swallowed OP2BR2 = Snorted/Sniffed OP2BR3 = Smoked OP2BR4 = non-IV Injection OP2BR5 = IV injection | | | |

FIG. 6UU

Tylox

| Question ID | Onscreen Text | Actor | Audio Recordings | ASI-MV Codes | Skip Logic | Consistency | Extreme Values |
|---|---|---|---|---|---|---|---|
| <br><br><br>OP2BW1<br>OP2BW2<br>OP2BW3<br>OP2BW4<br>OP2BW5<br>OP2BW6<br>OP2BW7<br>OP2BW8 | Where did you get the Tylox? Please click on all that apply.<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Tylox? Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP2BW1 = Own prescriptions<br>OP2BW2 = More than one Doctor<br>OP2BW3 = Internet shopping<br>OP2BW4 = Family<br>OP2BW5 = A dealer<br>OP2BW6 = Forgery<br>OP2BW7 = Stealing<br>OP2BW8 = Other | | | |
| OP2C30 | How many days in the past 30 days did you use Percodan in a way not prescribed by your doctor? That is using it for how it made you feel and not to help with pain.<br><br>Days [2 digit counter]<br>None | | How many days in the past 30 days did you use Percodan in a way not prescribed by your doctor? That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP2C = 0) codes as 0 | | |

FIG. 6VV

| Question ID | Onscreen Text | Actor | Audio Recordings | ASI-MV Codes | Skip Logic | Consistency | Extreme Values |
|---|---|---|---|---|---|---|---|
| OP2CR1<br>OP2CR2<br>OP2CR3<br>OP2CR4<br>OP2CR5 | How have you usually used Percodan? Please select all that apply.<br><br>Swallowed<br>Snorted/Sniffed<br>Smoked<br>Injected in skin or muscle<br>Injected in vein | | How have you usually used Percodan?<br>Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP2CR1 = Swallowed<br>•<br>• | | | |
| OP2CW1<br>OP2CW2<br>OP2CW3<br>OP2CW4<br>OP2CW5<br>OP2CW6<br>OP2CW7<br>OP2CW8 | Where did you get the Percodan? Please click on all that apply.<br><br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Percodan? Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP2CW1 = Own prescriptions<br>OP2CW2 = More than one Doctor<br>OP2CW3 = Internet shopping<br>OP2CW4 = Family<br>OP2CW5 = A dealer<br>OP2CW6 = Forgery<br>OP2CW7 = Stealing<br>OP2CW8 = Other | | | |

FIG. 6WW

| Question ID | Onscreen Text | Actor | Audio Recordings | ASI-MV Codes | Skip Logic | Consistency | Extreme Values |
|---|---|---|---|---|---|---|---|
| OP2D30 | How many days in the past 30 days did you use Combunox in a way not prescribed by your doctor? That is using it for how it made you feel and not to help with pain. Days [2 digit counter] None | | How many days in the past 30 days did you use Combunox in a way not prescribed by your doctor? That is using it for how it made you feel and not to help with pain. Please click on the up or down arrow on the counter to show the number of days - or if None, click here. | Coded as 2 digit variable (MAX = 30) 0 = None (-1 = 0) | If skipped (b/c OP2D = 0) codes as 0 | | |
| OP2DR1 OP2DR2 OP2DR3 OP2DR4 OP2DR5 | How have you usually used Combunox? Please select all that apply. Swallowed Snorted/Sniffed Smoked Injected in skin or muscle Injected in vein | | How have you usually used Combunox? Please select all that apply. • Swallowed • Snorted/Sniffed • Smoked • Injected in the skin or in the muscle • Injected into a vein | Each variable will be given a separate value 1 = Yes/Selected 0 = No/Not selected OP2DR1 = Swallowed OP2DR2 = Snorted/Sniffed OP2DR3 = Smoked OP2DR4 = non-IV Injection OP2DR5 = IV injection | | | |

FIG. 6XX

| Question ID | Onscreen Text | Actor | Audio Recordings | ASI-MV Codes | Skip Logic | Consistency | Extreme Values |
|---|---|---|---|---|---|---|---|
| OP2DW1<br>OP2DW2<br>OP2DW3<br>OP2DW4<br>OP2DW5<br>OP2DW6<br>OP2DW7<br>OP2DW8 | Where did you get the Combunox? Please click on all that apply.<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Combunox? Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP2DW1 = Own prescriptions<br>OP2DW2 = More than one Doctor<br>OP3DW3 = Internet shopping<br>OP2DW4 = Family<br>OP2DW5 = A dealer<br>OP2DW6 = Forgery<br>OP2DW7 = Stealing<br>OP2DW8 = Other | | | |
| OP2E30 | How many days in the past 30 days did you use Oxycodone iR in a way not prescribed by your doctor? That is using it for how it made you feel and not to help with pain.<br><br>Days [2 digit counter]<br>None | | How many days in the past 30 days did you use Oxycodone iR in a way not prescribed by your doctor? That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | If skipped (b/c OP2E = 0) codes as 0 | | |

FIG. 6YY

| Question ID | Onscreen Text | Actor | Audio Recordings | ASI-MV Codes | Skip Logic | Consistency | Extreme Values |
|---|---|---|---|---|---|---|---|
| OP2ER1<br>OP2ER2<br>OP2ER3<br>OP2ER4<br>OP2ER5 | How have you usually used Oxycodone IR? Please select all that apply.<br><br>Swallowed<br>Snorted/Sniffed<br>Smoked<br>Injected in skin or muscle<br>Injected in vein | | How have you usually used Oxycodone IR? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP2ER1 = Swallowed<br>•<br>•<br>• | | | |
| OP2EW1<br>OP2EW2<br>OP2EW3<br>OP2EW4<br>OP2EW5<br>OP2EW6<br>OP2EW7<br>OP2EW8 | Where did you get the Oxycodone IR? Please click on all that apply.<br><br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Oxycodone IR? Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP2EW1 = Own prescriptions<br>OP2EW2 = More than one Doctor<br>OP2EW3 = Internet shopping<br>OP2EW4 = Family<br>OP2EW5 = A dealer<br>OP2EW6 = Forgery<br>OP2EW7 = Stealing<br>OP2EW8 = Other | | | |

FIG. 6ZZ

| Question ID | Onscreen Text | Actor | Audio Recordings | ASI-MV Codes | Skip Logic | Consistency | Extreme Values |
|---|---|---|---|---|---|---|---|
| OP2F30 | How many days in the past 30 days did you use Other oxycodone in a way not prescribed by your doctor? That is using it for how it made you feel and not to help with pain. Days [2 digit counter] None | | How many days in the past 30 days did you use Other oxycodone in a way not prescribed by your doctor? That is using it for how it made you feel and not to help with pain. Please click on the up or down arrow on the counter to show the number of days - or if None, click here. | Coded as 2 digit variable (MAX = 30) 0 = None (-1 = 0) | If skipped (b/c OP2F = 0) codes as 0 | | |
| OP2FR1 OP2FR2 OP2FR3 OP2FR4 OP2FR5 | How have you usually used Other oxycodone? Please select all that apply. Swallowed Snorted/Sniffed Smoked Injected in skin or muscle Injected in vein | | How have you usually used Other oxycodone? Please select all that apply. • Swallowed • Snorted/Sniffed • Smoked • Injected in the skin or in the muscle • Injected into a vein | Each variable will be given a separate value 1 = Yes/Selected 0 = No/Not selected OP2FR1 = Swallowed OP2FR2 = Snorted/Sniffed OP2FR3 = Smoked OP2FR4 = non-IV Injection OP2FR5 = IV injection | | | |

FIG. 6AAA

| Question ID | Onscreen Text | Actor | Audio Recordings | AS1-MV Codes | Skip Logic | Consistency | Extreme Values |
|---|---|---|---|---|---|---|---|
| OP2FW1<br>OP2FW2<br>OP2FW3<br>OP2FW4<br>OP2FW5<br>OP2FW6<br>OP2FW7<br>OP2FW8 | Where did you get the Other oxycodone ? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Other oxycodone? Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP2FW1 = Own prescriptions<br>OP2FW2 = More than one Doctor<br>OP2FW3 = Internet shopping<br>OP2FW4 = Family<br>OP2FW5 = A dealer<br>OP2FW6 = Forgery<br>OP2FW7 = Stealing<br>OP2FW8 = Other | | | |

FIG. 6BBB

| Question ID | Onscreen Text | Actor | Audio Recordings | ASI-MV Codes | Skip Logic | Consistency | Extreme Values |
|---|---|---|---|---|---|---|---|
| OP3 (no screen =3)<br><br>OP3A = Lorcet<br>OP3B = Lortab<br>OP3C = Vicodin<br>OP3D = Vicoprofen<br>OP3E = Norco<br>OP3F = other hydrocodone<br>OP3G = none | If you have taken Lorcet, Lortab, Vicodin, Vicoprofen, Norco or other hydrocodone in the past 30 days please select the appropriate boxes below.<br><br>Remember to only select the boxes if you recognize the picture of the medications you used. These medications are also called Watson-387, Vikes & Hydro.<br><br>[IMAGE BOXES]<br>Lorcet<br>...<br>None | | If you have taken Lorcet, Lortab, Vicodin, Vicoprofen, Norco or other hydrocodone in the past 30 days please select the appropriate boxes below.<br><br>If none, click here.<br><br>Remember to only select the boxes if you recognize the picture of the medication you used. These medications are also called Watson-387, Vikes & Hydro. | Each variable will be given a separate value<br><br>1 = Yes/Selected<br>0 = No/Not selected<br><br>OP3A = Lorcet<br>OP3B = Lortab<br>OP3C = Vicodin<br>OP3D = Vicoprofen<br>OP3E = Norco<br>OP3F = other hydrocodone<br>OP3G = none | If OP3A = 1, enable OPRATE and go to OP3A30<br>If OP3B = 1, enable OPRATE and go to OP3B30<br>If OP3C = 1, enable OPRATE and go to<br>... | | |
| OP3A30 | How many days in the past 30 days did you use Lorcet in a way not prescribed by your doctor?<br><br>That is using it for how it made you feel and not to help with pain.<br><br>Days [2 digit counter]<br>None | | How many days in the past 30 days did you use Lorcet in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | If skipped (b/c OP3A = 0) codes as 0 | | |

FIG. 6CCC

| Question ID | Onscreen Text | Actor | Audio Recordings | ASI-MV Codes | Skip Logic | Consistency | Extreme Values |
|---|---|---|---|---|---|---|---|
| OP3AR1<br>OP3AR2<br>OP3AR3<br>OP3AR4<br>OP3AR5 | How have you usually used Lorcet? Please select all that apply.<br><br>Swallowed<br>Snorted/Sniffed<br>Smoked<br>Injected in skin or muscle<br>Injected in vein | | How have you usually used Lorcet? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP3AR1 = Swallowed<br>:<br>: | | | |
| OP3AW1<br>OP3AW2<br>OP3AW3<br>OP3AW4<br>OP3AW5<br>OP3AW6<br>OP3AW7<br>OP3AW8 | Where did you get the Lorcet? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Lorcet? Please click on all that apply:<br><br>- Your own prescriptions (from one Dr.)<br>- Multiple Doctors (from several Drs or emergency services)<br>- internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP3AW1 = Own prescriptions<br>OP3AW2 = More than one Doctor<br>OP3AW3 = internet shopping<br>OP3AW4 = Family<br>OP3AW5 = A dealer<br>OP3AW6 = Forgery<br>OP3AW7 = Stealing<br>OP3AW8 = Other | | | |

FIG. 6DDD

| Question ID | Onscreen Text | Actor | Audio Recordings | ASI-MV Codes | Skip Logic | Consistency | Extreme Values |
|---|---|---|---|---|---|---|---|
| OP3B30 | How many days in the past 30 days did you use Lortab in a way not prescribed by your doctor?<br><br>Days [2 digit counter]<br>None | | How many days in the past 30 days did you use Lortab in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP3B = 0) codes as 0 | | |
| OP3BR1<br>OP3BR2<br>OP3BR3<br>OP3BR4<br>OP3BR5 | How have you usually used Lortab?<br>Please select all that apply.<br>Swallowed<br>Snorted/Sniffed<br>Smoked<br>injected in skin or muscle<br>injected in vein | | How have you usually used Lortab?<br>Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP3BR1 = Swallowed<br>OP3BR2 = Snorted/Sniffed<br>OP3BR3 = Smoked<br>OP3BR4 = non–IV Injection<br>OP3BR5 = IV injection | | | |

FIG. 6EEE

| Question ID | Onscreen Text | Actor | Audio Recordings | ASI-MV Codes | Skip Logic | Consistency | Extreme Values |
|---|---|---|---|---|---|---|---|
| OP3BW1<br>OP3BW2<br>OP3BW3<br>OP3BW4<br>OP3BW5<br>OP3BW6<br>OP3BW7<br>OP3BW8 | Where did you get the Lortab? Please click on all that apply.<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Lortab? Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP3BW1 = Own prescriptions<br>OP3BW2 = More than one Doctor<br>OP3BW3 = Internet shopping<br>OP3BW4 = Family<br>OP3BW5 = A dealer<br>OP3BW6 = Forgery<br>OP3BW7 = Stealing<br>OP3BW8 = Other | | | |
| OP3C30 | How many days in the past 30 days did you use Vicodin in a way not prescribed by your doctor?<br><br>Days [2 digit counter]<br>None | | How many days in the past 30 days did you use Vicodin in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP3C = 0) codes as 0 | | |

FIG. 6FFF

| Question ID | Onscreen Text | Actor | Audio Recordings | ASI-MV Codes | Skip Logic | Consistency | Extreme Values |
|---|---|---|---|---|---|---|---|
| OP3CR1<br>OP3CR2<br>OP3CR3<br>OP3CR4<br>OP3CR5 | How have you usually used Vicodin? Please select all that apply.<br>- Swallowed<br>- Snorted/Sniffed<br>- Smoked<br>- Injected in skin or muscle<br>- Injected in vein | | How have you usually used Vicodin? Please select all that apply.<br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br>OP3CR1 = Swallowed<br>•<br>•<br>• | | | |
| OP3CW1<br>OP3CW2<br>OP3CW3<br>OP3CW4<br>OP3CW5<br>OP3CW6<br>OP3CW7<br>OP3CW8 | Where did you get the Vicodin? Please click on all that apply:<br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Vicodin? Please click on all that apply.<br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br>OP3CW1 = Own prescriptions<br>OP3CW2 = More than one Doctor<br>OP3CW3 = Internet shopping<br>OP3CW4 = Family<br>OP3CW5 = A dealer<br>OP3CW6 = Forgery<br>OP3CW7 = Stealing<br>OP3CW8 = Other | | | |

FIG. 6GGG

| Question ID | Onscreen Text | Actor | Audio Recordings | ASI-MV Codes | Skip Logic | Consistency | Extreme Values |
|---|---|---|---|---|---|---|---|
| OP3D30 | How many days in the past 30 days did you use Vicoprofen in a way not prescribed by your doctor?<br><br>That is using it for how it made you feel and not to help with pain.<br><br>Days [2 digit counter]<br>None | | How many days in the past 30 days did you use Vicoprofen in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP3D = 0) codes as 0 | | |
| OP3DR1<br>OP3DR2<br>OP3DR3<br>OP3DR4<br>OP3DR5 | How have you usually used Vicoprofen?<br>Please select all that apply.<br>Swallowed<br>Snorted/Sniffed<br>Smoked<br>injected in skin or muscle<br>injected in vein | | How have you usually used Vicoprofen?<br>Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP3DR1 = Swallowed<br>OP3DR2 = Snorted/Sniffed<br>OP3DR3 = Smoked<br>OP3DR4 = non-IV Injection<br>OP3DR5 = IV injection | | | |

FIG. 6HHH

| Question ID | Onscreen Text | Actor | Audio Recordings | ASI-MV Codes | Skip Logic | Consistency | Extreme Values |
|---|---|---|---|---|---|---|---|
| OP3DW1<br>OP3DW2<br>OP3DW3<br>OP3DW4<br>OP3DW5<br>OP3DW6<br>OP3DW7<br>OP3DW8 | Where did you get the Vicoprofen? Please click on all that apply.<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Vicoprofen? Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP3DW1 = Own prescriptions<br>OP3DW2 = More than one Doctor<br>OP3DW3 = Internet shopping<br>OP3DW4 = Family<br>OP3DW5 = A dealer<br>OP3DW6 = Forgery<br>OP3DW7 = Stealing<br>OP3DW8 = Other | | | |
| OP3E30 | How many days in the past 30 days did you use Narco in a way not prescribed by your doctor?<br>That is using it for how it made you feel and not to help with pain.<br>Days [2 digit counter]<br>None | | How many days in the past 30 days did you use Narco in a way not prescribed by your doctor?<br>That is using it for how it made you feel and not to help with pain.<br>Please click on the up or down arrow on the counter to show the number of days - or if None, click here. | Coded as 2 digit variable (MAX = 30)<br><br>0 = None<br>(-1 = 0) | if skipped (b/c OP3E = 0) codes as 0 | | |

FIG. 6III

| Question ID | Onscreen Text | Actor | Audio Recordings | ASI-MV Codes | Skip Logic | Consistency | Extreme Values |
|---|---|---|---|---|---|---|---|
| OP3ER1<br>OP3ER2<br>OP3ER3<br>OP3ER4<br>OP3ER5 | How have you usually used Norco? Please select all that apply:<br><br>Swallowed<br>Snorted/Sniffed<br>Smoked<br>Injected in skin or muscle<br>Injected in vein | | How have you usually used Norco? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP3ER1 = Swallowed<br>•<br>•<br>• | | | |
| OP3EW1<br>OP3EW2<br>OP3EW3<br>OP3EW4<br>OP3EW5<br>OP3EW6<br>OP3EW7<br>OP3EW8 | Where did you get the Norco? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Norco? Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP3EW1 = Own prescriptions<br>OP3EW2 = More than one Doctor<br>OP3EW3 = Internet shopping<br>OP3EW4 = Family<br>OP3EW5 = A dealer<br>OP3EW6 = Forgery<br>OP3EW7 = Stealing<br>OP3EW8 = Other | | | |

FIG. 6JJJ

| Question ID | Onscreen Text | Actor | Audio Recordings | ASI-MV Codes | Skip Logic | Consistency | Extreme Values |
|---|---|---|---|---|---|---|---|
| OP3F30 | How many days in the past 30 days did you use Other hydrocodone in a way not prescribed by your doctor? That is using it for how it made you feel and not to help with pain. Days [2 digit counter] None | | How many days in the past 30 days did you use Other hydrocodone in a way not prescribed by your doctor? That is using it for how it made you feel and not to help with pain. Please click on the up or down arrow on the counter to show the number of days - or if None, click here. | Coded as 2 digit variable (MAX = 30) 0 = None (-1 = 0) | if skipped (b/c OP3F = 0) codes as 0 | | |
| OP3FR1 OP3FR2 OP3FR3 OP3FR4 OP3FR5 | How have you usually used Other hydrocodone? Please select all that apply. Swallowed Snorted/Sniffed Smoked Injected in skin or muscle Injected in vein | | How have you usually used Other hydrocodone? Please select all that apply. • Swallowed • Snorted/Sniffed • Smoked • Injected in the skin or in the muscle • Injected into a vein | Each variable will be given a separate value 1 = Yes/Selected 0 = No/Not selected OP3FR1 = Swallowed OP3FR2 = Snorted/Sniffed OP3FR3 = Smoked OP3FR4 = non-IV Injection OP3FR5 = IV injection | | | |

FIG. 6KKK

| Question ID | Onscreen Text | Actor | Audio Recordings | ASI-MV Codes | Skip Logic | Consistency | Extreme Values |
|---|---|---|---|---|---|---|---|
| <br>OP3FW1<br>OP3FW2<br>OP3FW3<br>OP3FW4<br>OP3FW5<br>OP3FW6<br>OP3FW7<br>OP3FW8 | Where did you get the Other hydrocodone? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Other hydrocodone? Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP3FW1 = Own prescriptions<br>OP3FW2 = More than one Doctor<br>OP3FW3 = Internet shopping<br>OP3FW4 = Family<br>OP3FW5 = A dealer<br>OP3FW6 = Forgery<br>OP3FW7 = Stealing<br>OP3FW8 = Other | | | |

FIG. 6LLL.

| Question ID | Onscreen Text | Actor | Audio Recordings | ASI-MV Codes | Skip Logic | Consistency | Extreme Values |
|---|---|---|---|---|---|---|---|
| OP4 (no screen = 4) OP4A = Methadone OP4B = Methadone OP4C = none | If you have taken Methadone (or dolophine) in the past 30 days please select the appropriate boxes below. Remember to only select the boxes if you recognize the picture of the medications you used. These medications are also called Done, Amidone, Chocolate chip cookies (methadone combined with MDMA), Fizzies, Wafer, Dollies, and Frizzies. [IMAGE BOXES] Methadone Methadone none | | If you have taken Methadone (or dolophine) in the past 30 days please select the appropriate boxes below. If none, click here. Remember to only select the boxes if you recognize the picture of the medication you used. These medications are also called Done, Amidone, Chocolate chip cookies (methadone combined with MDMA), Fizzies, Wafer, Dollies, and Frizzies. | Each variable will be given a separate value 1 = Yes/Selected 0 = No/Not selected OP4A = Methadone OP4B = Methadone OP4C = none | If OP4A = 1, enable OPRATE and go to OP4A30 If OP4B = 1, enable OPRATE and go to OP4B30 If OP3C = 1, recode OP4A & OP4B = 0 | | |
| OP4A30 | How many days in the past 30 days did you useMethadone in a way not prescribed by your doctor? That is using it for how it made you feel and not to help with pain. Days None [NOTE: INCLUDE IMAGE OF METHADONE (Roxane)] | | How many days in the past 30 days did you use Methadone in a way not prescribed by your doctor? That is using it for how it made you feel and not to help with pain. Please click on the up or down arrow on the counter to show the number of days - or if None, click here. | Coded as 2 digit variable (MAX = 30) 0 = None (-1 = 0) | if skipped (b/c OP4A = 0) codes as 0 | | |

FIG. 6MMM

| Question ID | Onscreen Text | Actor | Audio Recordings | ASI-MV Codes | Skip Logic | Consistency | Extreme Values |
|---|---|---|---|---|---|---|---|
| OP4AR1<br>OP4AR2<br>OP4AR3<br>OP4AR4<br>OP4AR5 | How have you usually used Methadone? Please select all that apply.<br>Swallowed<br>Snorted/Sniffed<br>Smoked<br>Injected in skin or muscle<br>Injected in vein<br>[NOTE: INCLUDE IMAGE OF METHADONE (Roxane)] | | How have you usually used Methadone? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP4AR1 = Swallowed<br>•<br>• | | | |
| OP4AW1<br>OP4AW2<br>OP4AW3<br>OP4AW4<br>OP4AW5<br>OP4AW6<br>OP4AW7<br>OP4AW8 | Where did you get the Methadone? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake | | Where did you get the Methadone? Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP4AW1 = Own prescriptions<br>OP4AW2 = More than one Doctor<br>OP4AW3 = Internet shopping<br>OP4AW4 = Family<br>OP4AW5 = A dealer<br>OP4AW6 = Forgery<br>OP4AW7 = Stealing<br>OP4AW8 = Other | | | |

FIG. 6NNN

| Question ID | Onscreen Text | Actor | Audio Recordings | ASI-MV Codes | Skip Logic | Consistency | Extreme Values |
|---|---|---|---|---|---|---|---|
| OP4B30 | How many days in the past 30 days did you use Methadone in a way not prescribed by your doctor?<br><br>That is using it for how it made you feel and not to help with pain.<br><br>Days<br>None<br>[NOTE: INCLUDE IMAGE OF METHADONE (Lilly)] | | How many days in the past 30 days did you use Methadone in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | If skipped (b/c OP4B = 0) codes as 0 | | |
| OP4BR1<br>OP4BR2<br>OP4BR3<br>OP4BR4<br>OP4BR5 | How have you usually used Methadone?<br>Please select all that apply.<br><br>Swallowed<br>Snorted/Sniffed<br>Smoked<br>Injected in skin or muscle<br>Injected in vein<br>[NOTE: INCLUDE IMAGE OF METHADONE (Lilly)] | | How have you usually used Methadone?<br>Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP4BR1 = Swallowed<br>OP4BR2 = Snorted/Sniffed<br>OP4BR3 = Smoked<br>OP4BR4 = non-IV Injection<br>OP4BR5 = IV injection | | | |

FIG. 6OOO

| Question ID | Onscreen Text | Actor | Audio Recordings | ASI MV Codes | Skip Logic | Consistency | Extreme Values |
|---|---|---|---|---|---|---|---|
| OP4BW1<br>OP4BW2<br>OP4BW3<br>OP4BW4<br>OP4BW5<br>OP4BW6<br>OP4BW7<br>OP4BW8 | Where did you get the Methadone? Please click on all that apply:<br>- Your own prescriptions (from one Dr.)<br>- Multiple Doctors (from several Drs or emergency services)<br>- Internet shopping (without a doctor's visit)<br>- Family, friend or acquaintance<br>-A dealer(someone known to sell drugs)<br>- Prescription forgery (Writing or buying fake . . . | | Where did you get the Methadone? Please click on all that apply:<br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP4BW1 = Own prescriptions<br>OP4BW2 = More than one Doctor<br>OP4BW3 = Internet shopping<br>OP4BW4 = Family<br>OP4BW5 = A dealer<br>OP4BW6 = Forgery<br>OP4BW7 = Stealing<br>OP4BW8 = Other | | | |
| OP5 (no screen = 5)<br>OP5A = Demerol<br>OP5B = Stadol<br>OP5C = Other meperidine<br>OP5D = none | If you have taken Demerol, Stadol, or other meperidine in the past 30 days please select the appropriate boxes below.<br>Remember to only select the boxes if you recognize the picture of the medication you used. | | If you have taken Demerol, Stadol, or other meperidine in the past 30 days please select the appropriate boxes below.<br>If none, click here.<br>Remember to only select the boxes if you recognize the picture of the medication you used. | Each variable will be given a separate value<br><br>1 = Yes/Selected<br>0 = No/Not selected<br><br>OP5A = Demerol<br>OP5B = Stadol<br>OP5C = Other meperidine<br>OP5D = none | If OP5A = 1, enable OPRATE and go to OP5A30<br>If OP5B = 1, enable OPRATE<br>. . . | | |

FIG. 6PPP

| Question ID | Onscreen Text | Actor | Audio Recordings | ASI-MV Codes | Skip Logic | Consistency | Extreme Values |
|---|---|---|---|---|---|---|---|
| OP5A30 | How many days in the past 30 days did you use Demerol in a way not prescribed by your doctor? That is using it for how it made you feel and not to help with pain. Days None | | How many days in the past 30 days did you use Demerol in a way not prescribed by your doctor? That is using it for how it made you feel and not to help with pain. Please click on the up or down arrow on the counter to show the number of days - or if None, click here. | Coded as 2 digit variable (MAX = 30) 0 = None (-1 = 0) | If skipped (b/c OP5A = 0) codes as 0 | | |
| OP5AR1 OP5AR2 OP5AR3 OP5AR4 OP5AR5 | How have you usually used Demerol? Please select all that apply. Swallowed Snorted/Sniffed Smoked Injected in skin or muscle Injected in vein | | How have you usually used Demerol? Please select all that apply. · Swallowed · Snorted/Sniffed · Smoked · Injected in the skin or in the muscle · Injected into a vein | Each variable will be given a separate value 1 = Yes/Selected 0 = No/Not selected OP5AR1 = Swallowed OP5AR2 = Snorted/Sniffed OP5AR3 = Smoked OP5AR4 = non-IV Injection OP5AR5 = IV injection | | | |

FIG. 6QQQ

| Question ID | Onscreen Text | Actor | Audio Recordings | ASI-MV Codes | Skip Logic | Consistency | Extreme Values |
|---|---|---|---|---|---|---|---|
| OP5AW1<br>OP5AW2<br>OP5AW3<br>OP5AW4<br>OP5AW5<br>OP5AW6<br>OP5AW7<br>OP5AW8 | Where did you get the Demerol?<br>Please click on all that apply.<br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Demerol?<br>Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP5AW1 = Own prescriptions<br>OP5AW2 = More than one Doctor<br>OP5AW3 = Internet shopping<br>OP5AW4 = Family<br>OP5AW5 = A dealer<br>OP5AW6 = Forgery<br>OP5AW7 = Stealing<br>OP5AW8 = Other | | | |
| OP5B30 | How many days in the past 30 days did you use Stadol in a way not prescribed by your doctor?<br>That is using it for how it made you feel and not to help with pain.<br>Days<br>None | | How many days in the past 30 days did you use Stadol in a way not prescribed by your doctor?<br>That is using it for how it made you feel and not to help with pain.<br>Please click on the up or down arrow on the counter to show the number of days - or if None, click here. | Coded as 2 digit variable (MAX = 30)<br>0 = None<br>(-1 = 0) | if skipped (b/c OP5B = 0) codes as 0 | | |

FIG. 6RRR

| Question ID | Onscreen Text | Actor | Audio Recordings | ASI-MV Codes | Skip Logic | Consistency | Extreme Values |
|---|---|---|---|---|---|---|---|
| OP5BR1<br>OP5BR2<br>OP5BR3<br>OP5BR4<br>OP5BR5 | How have you usually used Stadol? Please select all that apply:<br><br>Swallowed<br>Snorted/Sniffed<br>Smoked<br>Injected in skin or muscle<br>Injected in vein | | How have you usually used Stadol? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP5BR1 = Swallowed<br>.<br>.<br>. | | | |
| OP5BW1<br>OP5BW2<br>OP5BW3<br>OP5BW4<br>OP5BW5<br>OP5BW6<br>OP5BW7<br>OP5BW8 | Where did you get the Stadol? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Stadol? Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP5BW1 = Own prescriptions<br>OP5BW2 = More than one Doctor<br>OP5BW3 = Internet shopping<br>OP5BW4 = Family<br>OP5BW5 = A dealer<br>OP5BW6 = Forgery<br>OP5BW7 = Stealing<br>OP5BW8 = Other | | | |

FIG. 6SSS

| Question ID | Onscreen Text | Actor | Audio Recordings | ASI-MV Codes | Skip Logic | Consistency | Extreme Values |
|---|---|---|---|---|---|---|---|
| OP5C30 | How many days in the past 30 days did you use Other meperidine in a way not prescribed by your doctor? That is using it for how it made you feel and not to help with pain. Days None | | How many days in the past 30 days did you use Other meperidine in a way not prescribed by your doctor? That is using it for how it made you feel and not to help with pain. Please click on the up or down arrow on the counter to show the number of days - or if None, click here. | Coded as 2 digit variable (MAX = 30) 0 = None (-1 = 0) | If skipped (b/c OP5C = 0) codes as 0 | | |
| OP5CR1 OP5CR2 OP5CR3 OP5CR4 OP5CR5 | How have you usually used Other meperidine? Please select all that apply. Swallowed Snorted/Sniffed Smoked injected in skin or muscle injected in vein | | How have you usually used Other meperidine? Please select all that apply. - Swallowed - Snorted/Sniffed - Smoked - Injected in the skin or in the muscle - Injected into a vein | Each variable will be given a separate value 1 = Yes/Selected 0 = No/Not selected OP5CR1 = Swallowed OP5CR2 = Snorted/Sniffed OP5CR3 = Smoked OP5CR4 = non-IV Injection OP5CR5 = IV injection | | | |

FIG. 6TTT

| Question ID | Onscreen Text | Actor | Audio Recordings | ASI-MV Codes | Skip Logic | Consistency | Extreme Values |
|---|---|---|---|---|---|---|---|
| OP5CW1<br>OP5CW2<br>OP5CW3<br>OP5CW4<br>OP5CW5<br>OP 5CW6<br>OP5CW7<br>OP5CW8 | Where did you get the Other meperidine? Please click on all that apply.<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Other meperidine? Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP5CW1 = Own prescriptions<br>OP5CW2 = More than one Doctor<br>OP5CW3 = Internet shopping<br>OP5CW4 = Family<br>OP5CW5 = A dealer<br>OP5CW6 = Forgery<br>OP5CW7 = Stealing<br>OP5CW8 = Other | | | |

FIG. 6UUU

| Question ID | Onscreen Text | Actor | Audio Recordings | ASI-MV Codes | Skip Logic | Consistency | Extreme Values |
|---|---|---|---|---|---|---|---|
| OP6 (no screen = 6)<br><br>OP6A = Actiq<br>OP6B = Duragesic<br>OP6C = Fentanyl patch<br>OP6D = none | If you have taken Actiq, Duragesic or Fentanyl patch in the past 30 days please select the appropriate boxes below.<br><br>Remember to only select the boxes if you recognize the picture of the medications you used. These medications are also called D-cets.<br><br>[IMAGE BOXES]<br>Actiq<br>Duragesic<br>Fentanyl patch<br>none | | If you have taken Actiq, Duragesic or Fentanyl patch in the past 30 days please select the appropriate boxes below.<br><br>If none, click here.<br><br>Remember to only select the boxes if you recognize the picture of the medication you used. These medications are also called Perc-a-pops, Pain patch, Morphine patch, Apache, Dance fever, Friend, Goodfellas, Great bear, He-man, Jackpot, King Ivory, Murder 8, Tango & Cash. | Each variable will be given a separate value<br><br>1 = Yes/Selected<br>0 = No/Not selected<br><br>OP6A = Actiq<br>OP6B = Duragesic<br>OP6C = Fentanyl patch<br>OP6D = none | If OP6A = 1, enable OPRATE and go to OP6A30<br>If OP6B = 1, enable OPRATE and go to OP6B30<br>If OP6C = 1, enable OPRATE and go to OP6C30 | | |
| OP6A30 | How many days in the past 30 days did you use Actiq in a way not prescribed by your doctor?<br><br>That is using it for how it made you feel and not to help with pain.<br><br>Days<br>None | | How many days in the past 30 days did you use Actiq in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP6A = 0) codes as 0 | | |

FIG. 6VVV

| Question ID | Onscreen Text | Actor | Audio Recordings | ASI-MV Codes | Skip Logic | Consistency | Extreme Values |
|---|---|---|---|---|---|---|---|
| OP6AR1<br>OP6AR2<br>OP6AR3<br>OP6AR4<br>OP6AR5 | How have you usually used Actiq? Please select all that apply.<br><br>Swallowed<br>Snorted/Sniffed<br>Smoked<br>Injected in skin or muscle<br>Injected in vein | | How have you usually used Actiq? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP6AR1 = Swallowed<br>•<br>•<br>• | | | |
| OP6AW1<br>OP6AW2<br>OP7AW3<br>OP6AW4<br>OP6AW5<br>OP6AW6<br>OP6AW7<br>OP6AW8 | Where did you get the Actiq? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Actiq? Please click on all that apply.<br><br>- Your own prescriptions (from one Dr.)<br>- Multiple Doctors (from several Drs or emergency services)<br>- internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP6AW1 = Own prescriptions<br>OP6AW2 = More than one Doctor<br>OP6AW3 = internet shopping<br>OP6AW4 = Family<br>OP6AW5 = A dealer<br>OP6AW6 = Forgery<br>OP6AW7 = Stealing<br>OP6AW8 = Other | | | |

FIG. 6WWW

| Question ID | Onscreen Text | Actor | Audio Recordings | ASI-MV Codes | Skip Logic | Consistency | Extreme Values |
|---|---|---|---|---|---|---|---|
| OP6B30 | How many days in the past 30 days did you use Duragesic in a way not prescribed by your doctor?<br><br>That is using it for how it made you feel and not to help with pain.<br><br>Days<br>None | | How many days in the past 30 days did you use Duragesic in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP6B = 0) codes as 0 | | |
| OP6BR1<br>OP6BR2<br>OP6BR3<br>OP6BR4<br>OP6BR5 | How have you usually used Duragesic?<br>Please select all that apply.<br><br>Swallowed<br>Snorted/Sniffed<br>Smoked<br>Injected in skin or muscle<br>Injected in vein | | How have you usually used Duragesic?<br>Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP6BR1 = Swallowed<br>OP6BR2 = Snorted/Sniffed<br>OP6BR3 = Smoked<br>OP6BR4 = non-IV Injection<br>OP6BR5 = IV injection | | | |

FIG. 6XXX

| Question ID | Onscreen Text | Actor | Audio Recordings | ASI-MV Codes | Skip Logic | Consistency | Extreme Values |
|---|---|---|---|---|---|---|---|
| | Where did you get the Duragesic? Please click on all that apply: | | Where did you get the Duragesic? Please click on all that apply: | Each variable will be given a separate value | | | |
| OP6BW1<br>OP6BW2<br>OP6BW3<br>OP6BW4<br>OP7BW5<br>OP6BW6<br>OP6BW7<br>OP6BW8 | - Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | - Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | 1 = Yes/Selected<br>0 = No/Not selected<br><br>OP6BW1 = Own prescriptions<br>OP6BW2 = More than one Doctor<br>OP6BW3 = Internet shopping<br>OP6BW4 = Family<br>OP6BW5 = A dealer<br>OP6BW6 = Forgery<br>OP6BW7 = Stealing<br>OP6BW8 = Other | | | |
| OP6C30 | How many days in the past 30 days did you use Fentanyl patch in a way not prescribed by your doctor? That is using it for how it made you feel and not to help with pain.<br><br>Days<br>None | | How many days in the past 30 days did you use Fentanyl patch in a way not prescribed by your doctor? That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | If skipped (b/c OP6C = 0) codes as 0 | | |

FIG. 6YYY

| Question ID | Onscreen Text | Actor | Audio Recordings | ASI-MV Codes | Skip Logic | Consistency | Extreme Values |
|---|---|---|---|---|---|---|---|
| OP6CR1<br>OP6CR2<br>OP6CR3<br>OP6CR4<br>OP6CR5 | How have you usually used Fentanyl patch? Please select all that apply.<br><br>Swallowed<br>Snorted/Sniffed<br>Smoked<br>Injected in skin or muscle<br>Injected in vein | | How have you usually used Fentanyl patch? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP6CR1 = Swallowed<br>⋮ | | | |
| OP6CW1<br>OP6CW2<br>OP6CW3<br>OP6CW4<br>OP6CW5<br>OP6CW6<br>OP6CW7<br>OP6CW8 | Where did you get the Fentanyl patch? Please click on all that apply.<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Fentanyl patch? Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP6CW1 = Own prescriptions<br>OP6CW2 = More than one Doctor<br>OP6CW3 = Internet shopping<br>OP6CW4 = Family<br>OP6CW5 = A dealer<br>OP6CW6 = Forgery<br>OP6CW7 = Stealing<br>OP6CW8 = Other | | | |

FIG. 6ZZZ

| Question ID | Onscreen Text | Actor | Audio Recordings | ASI-MV Codes | Skip Logic | Consistency | Extreme Values |
|---|---|---|---|---|---|---|---|
| OP7 (no screen = 7) OP7A = MS-Contin OP7B = MS-IR OP7C = Kadian OP7D = none | If you have taken Dilaudid, Palladone or Other hydromorphone in the past 30 days please select the appropriate boxes below. Remember to only select the boxes if you recognize the picture of the medication you used. These medications are also called D-cets. [IMAGE BOXES] Dilaudid Palladone Other hydromorphone none | | If you have taken Dilaudid, Palladone or Other hydromorphone in the past 30 days please select the appropriate boxes below. If none, click here. Remember to only select the boxes if you recognize the picture of the medication you used. These medications are also called Dillies, Dust, Juice, Smack, and D. | Each variable will be given a separate value 1 = Yes/Selected 0 = No/Not selected OP7A = Dilaudid OP7B = Palladone OP7C = Other hydromorphone OP7D = none | If OP7A = 1, enable OPRATE and go to OP7A30 If OP7B = 1, enable OPRATE and go to OP7B30 If OP7C = 1, enable OPRATE and go to OP7C30 . . . | | |
| OP7A30 | How many days in the past 30 days did you use Dilaudid in a way not prescribed by your doctor? Days None | | How many days in the past 30 days did you useDilaudid in a way not prescribed by your doctor? That is using it for how it made you feel and not to help with pain. Please click on the up or down arrow on the counter to show the number of days - or if None, click here. | Coded as 2 digit variable (MAX = 30) 0 = None (-1 = 0) | If skipped (b/c OP7A = 0) codes as 0 | | |

FIG. 6AAAA

| Question ID | Onscreen Text | Actor | Audio Recordings | ASI-MV Codes | Skip Logic | Consistency | Extreme Values |
|---|---|---|---|---|---|---|---|
| OP7AR1<br>OP7AR2<br>OP7AR3<br>OP7AR4<br>OP7AR5 | How have you usually used Dilaudid? Please select all that apply.<br><br>Swallowed<br>Snorted/Sniffed<br>Smoked<br>Injected in skin or muscle<br>Injected in vein | | How have you usually used Dilaudid? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP7AR1 = Swallowed<br>.<br>.<br>. | | | |
| OP7AW1<br>OP7AW2<br>OP7AW3<br>OP7AW4<br>OP7AW5<br>OP7AW6<br>OP7AW7<br>OP7AW8 | Where did you get the Dilaudid? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Dilaudid? Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP7AW1 = Own prescriptions<br>OP7AW2 = More than one Doctor<br>OP7AW3 = Internet shopping<br>OP7AW4 = Family<br>OP7AW5 = A dealer<br>OP7AW6 = Forgery<br>OP7AW7 = Stealing<br>OP7AW8 = Other | | | |

FIG. 6BBBB

| Question ID | Onscreen Text | Actor | Audio Recordings | ASI-MV Codes | Skip Logic | Consistency | Extreme Values |
|---|---|---|---|---|---|---|---|
| OP7B30 | How many days in the past 30 days did you use Palladone in a way not prescribed by your doctor?<br><br>That is using it for how it made you feel and not to help with pain.<br><br>Days<br>None | | How many days in the past 30 days did you use Palladone in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP7B = 0) codes as 0 | | |
| OP7BR1<br>OP7BR2<br>OP7BR3<br>OP7BR4<br>OP7BR5 | How have you usually used Palladone?<br>Please select all that apply.<br><br>Swallowed<br>Snorted/Sniffed<br>Smoked<br>injected in skin or muscle<br>injected in vein | | How have you usually used Palladone?<br>Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP7BR1 = Swallowed<br>OP7BR2 = Snorted/Sniffed<br>OP7BR3 = Smoked<br>OP7BR4 = non-IV injection<br>OP7BR5 = IV injection | | | |

FIG. 6CCCC

| Question ID | Onscreen Text | Actor | Audio Recordings | ASI-MV Codes | Skip Logic | Consistency | Extreme Values |
|---|---|---|---|---|---|---|---|
| OP7BW1<br>OP7BW2<br>OP7BW3<br>OP7BW4<br>OP7BW5<br>OP7BW6<br>OP7BW7<br>OP7BW8 | Where did you get the Palladone? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Palladone? Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP7BW1 = Own prescriptions<br>OP7BW2 = More than one Doctor<br>OP7BW3 = Internet shopping<br>OP7BW4 = Family<br>OP7BW5 = A dealer<br>OP7BW6 = Forgery<br>OP7BW7 = Stealing<br>OP7BW8 = Other | | | |
| OP7C30 | How many days in the past 30 days did you use Other hydromorphone in a way not prescribed by your doctor? That is using it for how it made you feel and not to help with pain.<br><br>Days<br>None | | How many days in the past 30 days did you use Other hydromorphone in a way not prescribed by your doctor? That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | If skipped (b/c OP7C = 0) codes as 0 | | |

FIG. 6DDDD

| Question ID | Onscreen Text | Actor | Audio Recordings | ASI-MV Codes | Skip Logic | Consistency | Extreme Values |
|---|---|---|---|---|---|---|---|
| OP7CR1<br>OP7CR2<br>OP7CR3<br>OP7CR4<br>OP7CR5 | How have you usually used Other hydromorphone? Please select all that apply.<br><br>Swallowed<br>Snorted/Sniffed<br>Smoked<br>Injected in skin or muscle<br>Injected in vein | | How have you usually used Other hydromorphone? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP7CR1 = Swallowed<br>•<br>•<br>• | | | |
| OP7CW1<br>OP7CW2<br>OP7CW3<br>OP7CW4<br>OP7CW5<br>OP7CW6<br>OP7CW7<br>OP7CW8 | Where did you get the Other hydromorphone? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Other hydromorphone? Please click on all that apply.<br><br>- Your own prescriptions (from one Dr.)<br>- Multiple Doctors (from several Drs or emergency services)<br>- internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP7CW1 = Own prescriptions<br>OP7CW2 = More than one Doctor<br>OP7CW3 = Internet shopping<br>OP7CW4 = Family<br>OP7CW5 = A dealer<br>OP7CW6 = Forgery<br>OP7CW7 = Stealing<br>OP7CW8 = Other | | | |

FIG. 6EEEE

| Question ID | Onscreen Text | Actor | Audio Recordings | ASI-MV Codes | Skip Logic | Consistency | Extreme Values |
|---|---|---|---|---|---|---|---|
| OP8 (no screen = 8)<br>OP8A = MS-Contin<br>OP8B = MS-IR<br>OP8C = Kadian<br>OP8D = Avinza<br>OP8E = Other morphine<br>OP8F = none | If you have taken MS-Contin, Morphine, MS-IR, Kadian or Avinza in the past 30 days please select the appropriate boxes below.<br>Remember to only select the boxes if you recognize the picture of the medications you used. These medications are also called D-cets.<br>[IMAGE BOXES]<br>MS-Contin<br>MS-IR<br>Kadian<br>Avinza<br>Other morphine<br>none | | If you have taken MS-Contin, Morphine, MS-IR, Kadian or Avinza in the past 30 days please select the appropriate boxes below.<br>If none, click here.<br>Remember to only select the boxes if you recognize the picture of the medication you used. These medications are also called M, MS, Dreamer, Emsel, First line, God's drug, Hows, Miss Emma, Mister blue, Morph, Morpho, and Unkie. | Each variable will be given a separate value<br>1 = Yes/Selected<br>0 = No/Not selected<br>OP8A = MS-Contin<br>OP8B = MS-IR<br>OP8C = Kadian<br>OP8D = Avinza<br>OP8E = Other morphine<br>OP8F = none | If OP8A = 1, enable OPRATE and go to OP8A30<br>If OP8B = 1, enable OPRATE and go to OP8B30<br>If OP8C = 1, enable OPRATE and go to OP8C30<br>. . . | | |
| OP8A30 | How many days in the past 30 days did you use MS-Contin in a way not prescribed by your doctor?<br>That is using it for how it made you feel and not to help with pain.<br>Days<br>None | | How many days in the past 30 days did you use MS-Contin in a way not prescribed by your doctor?<br>That is using it for how it made you feel and not to help with pain.<br>Please click on the up or down arrow on the counter to show the number of days - or if None, click here. | Coded as 2 digit variable (MAX = 30)<br>0 = None<br>(-1 = 0) | If skipped (b/c OP8A = 0) codes as 0 | | |

FIG. 6FFFF

| Question ID | Onscreen Text | Actor | Audio Recordings | ASI-MV Codes | Skip Logic | Consistency | Extreme Values |
|---|---|---|---|---|---|---|---|
| OP8AR1<br>OP8AR2<br>OP8AR3<br>OP8AR4<br>OP8AR5 | How have you usually used MS Contin? Please select all that apply.<br>- Swallowed<br>- Snorted/Sniffed<br>- Smoked<br>- Injected in skin or muscle<br>- Injected in vein | | How have you usually used MS Contin?<br>Please select all that apply.<br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP8AR1 = Swallowed<br>•<br>•<br>• | | | |
| OP8AW1<br>OP8AW2<br>OP8AW3<br>OP8AW4<br>OP8AW5<br>OP8AW6<br>OP8AW7<br>OP8AW8 | Where did you get the MS Contin? Please click on all that apply.<br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the MS Contin? Please click on all that apply.<br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP8AW1 = Own prescriptions<br>OP8AW2 = More than one Doctor<br>OP8AW3 = Internet shopping<br>OP8AW4 = Family<br>OP8AW5 = A dealer<br>OP8AW6 = Forgery<br>OP8AW7 = Stealing<br>OP8AW8 = Other | | | |

FIG. 6GGGG

| Question ID | Onscreen Text | Actor | Audio Recordings | ASI-MV Codes | Skip Logic | Consistency | Extreme Values |
|---|---|---|---|---|---|---|---|
| OP8B30 | How many days in the past 30 days did you use MS-IR in a way not prescribed by your doctor?<br><br>That is using it for how it made you feel and not to help with pain.<br><br>Days<br>None | | How many days in the past 30 days did you use MS-IR in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP8B = 0) codes as 0 | | |
| OP8BR1<br>OP8BR2<br>OP8BR3<br>OP8BR4<br>OP8BR5 | How have you usually used MS-IR? Please select all that apply.<br>Swallowed<br>Snorted/Sniffed<br>Smoked<br>Injected in skin or muscle<br>Injected in vein | | How have you usually used MS-IR? Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP8BR1 = Swallowed<br>OP8BR2 = Snorted/Sniffed<br>OP8BR3 = Smoked<br>OP8BR4 = non-IV Injection<br>OP8BR5 = IV injection | | | |

FIG. 6HHHHH

| Question ID | Onscreen Text | Actor | Audio Recordings | ASI-MV Codes | Skip Logic | Consistency | Extreme Values |
|---|---|---|---|---|---|---|---|
| OP8BW1<br>OP8BW2<br>OP8BW3<br>OP8BW4<br>OP8BW5<br>OP8BW6<br>OP8BW7<br>OP8BW8 | Where did you get the MS-IR? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the MS-IR? Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP8BW1 = Own prescriptions<br>OP8BW2 = More than one Doctor<br>OP8BW3 = Internet shopping<br>OP8BW4 = Family<br>OP8BW5 = A dealer<br>OP8BW6 = Forgery<br>OP8BW7 = Stealing<br>OP8BW8 = Other | | | |
| OP8C30 | How many days in the past 30 days did you use Kadian in a way not prescribed by your doctor?<br>That is using it for how it made you feel and not to help with pain.<br>Days<br>None | | How many days in the past 30 days did you use Kadian in a way not prescribed by your doctor?<br>That is using it for how it made you feel and not to help with pain.<br>Please click on the up or down arrow on the counter to show the number of days - or if None, click here. | Coded as 2 digit variable (MAX = 30)<br><br>0 = None<br><br>(-1 = 0) | if skipped (b/c OP8C = 0) codes as 0 | | |

FIG. 6IIII

| Question ID | Onscreen Text | Actor | Audio Recordings | ASI-MV Codes | Skip Logic | Consistency | Extreme Values |
|---|---|---|---|---|---|---|---|
| OP8CR1<br>OP8CR2<br>OP8CR3<br>OP8CR4<br>OP8CR5 | How have you usually used Kadian? Please select all that apply.<br><br>Swallowed<br>Snorted/Sniffed<br>Smoked<br>Injected in skin or muscle<br>Injected in vein | | How have you usually used Kadian? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP8CR1 = Swallowed<br>•<br>•<br>• | | | |
| OP8CW1<br>OP8CW2<br>OP8CW3<br>OP8CW4<br>OP8CW5<br>OP8CW6<br>OP8CW7<br>OP8CW8 | Where did you get the Kadian? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Kadian? Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP8CW1 = Own prescriptions<br>OP8CW2 = More than one Doctor<br>OP8CW3 = Internet shopping<br>OP8CW4 = Family<br>OP8CW5 = A dealer<br>OP8CW6 = Forgery<br>OP8CW7 = Stealing<br>OP8CW8 = Other | | | |

FIG. 6JJJJ

| Question ID | Onscreen Text | Actor | Audio Recordings | ASI-MV Codes | Skip Logic | Consistency | Extreme Values |
|---|---|---|---|---|---|---|---|
| OP8D30 | How many days in the past 30 days did you use Avinza in a way not prescribed by your doctor?<br><br>That is using it for how it made you feel and not to help with pain.<br><br>Days<br>None | | How many days in the past 30 days did you use Avinza in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br>(-1 = 0) | if skipped (b/c OP8D = 0) codes as 0 | | |
| OP8DR1<br>OP8DR2<br>OP8DR3<br>OP8DR4<br>OP8DR5 | How have you usually used Avinza?<br>Please select all that apply.<br><br>Swallowed<br>Snorted/Sniffed<br>Smoked<br>Injected in skin or muscle<br>Injected in vein | | How have you usually used Avinza?<br>Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP8DR1 = Swallowed<br>OP8DR2 = Snorted/Sniffed<br>OP8DR3 = Smoked<br>OP8DR4 = non-IV Injection<br>OP8DR5 = IV injection | | | |

FIG. 6KKKK

| Question ID | Onscreen Text | Actor | Audio Recordings | ASI-MV Codes | Skip Logic | Consistency | Extreme Values |
|---|---|---|---|---|---|---|---|
| OP8DW1 OP8DW2 OP8DW3 OP8DW4 OP8DW5 OP8DW6 OP8DW7 OP8DW8 | Where did you get the Avinza? Please click on all that apply:<br><br>- Your own prescriptions (from one Dr.)<br>- Multiple Doctors (from several Drs or emergency services)<br>- internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Avinza? Please click on all that apply:<br><br>- Your own prescriptions (from one Dr.)<br>- Multiple Doctors (from several Drs or emergency services)<br>- internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP8DW1 = Own prescriptions<br>OP8DW2 = More than one Doctor<br>OP8DW3 = Internet shopping<br>OP8DW4 = Family<br>OP8DW5 = A dealer<br>OP8DW6 = Forgery<br>OP8DW7 = Stealing<br>OP8DW8 = Other | | | |
| OP8E30 | How many days in the past 30 days did you use Other morphine in a way not prescribed by your doctor? That is using it for how it made you feel and not to help with pain.<br><br>Days<br>None | | How many days in the past 30 days did you use Other morphine in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP8E = 0) codes as 0 | | |

FIG. 6LLLL

| Question ID | Onscreen Text | Actor | Audio Recordings | ASI-MV Codes | Skip Logic | Consistency | Extreme Values |
|---|---|---|---|---|---|---|---|
| OP8ER1<br>OP8ER2<br>OP8ER3<br>OP8ER4<br>OP8ER5 | How have you usually used Other morphine? Please select all that apply.<br><br>Swallowed<br>Snorted/Sniffed<br>Smoked<br>Injected in skin or muscle<br>Injected in vein | | How have you usually used Other morphine? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP8ER1 = Swallowed<br>•<br>• | | | |
| OP8EW1<br>OP8EW2<br>OP8EW3<br>OP8EW4<br>OP8EW5<br>OP8EW6<br>OP8EW7<br>OP8EW8 | Where did you get the Other morphine? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Other morphine? Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP8EW1 = Own prescriptions<br>OP8EW2 = More than one Doctor<br>OP8EW3 = Internet shopping<br>OP8EW4 = Family<br>OP8EW5 = A dealer<br>OP8EW6 = Forgery<br>OP8EW7 = Stealing<br>OP8EW8 = Other | | | |

FIG. 6MMMM

| Question ID | Onscreen Text | Actor | Audio Recordings | ASI-MV Codes | Skip Logic | Consistency | Extreme Values |
|---|---|---|---|---|---|---|---|
| OP9 (no screen = 9)<br>OP9A = Talacen<br>OP9B = Talwin Compound<br>OP9C = Talwin NX<br>OP9D = Other pentazocine<br>OP9E = none | If you have taken Talacen, Talwin Compound, Talwin NX, or other pentazocine in the past 30 days please select the appropriate boxes below.<br><br>Remember to only select the boxes if you recognize the picture of the medications you used. These medications are also called D-cets.<br><br>[IMAGE BOXES]<br>Talacen<br>Talwin Compound<br>Talwin NX<br>Other pentazocine<br>none | | If you have taken Talacen, Talwin Compound, Talwin NX, or other pentazocine in the past 30 days please select the appropriate boxes below.<br><br>If none, click here.<br><br>Remember to only select the boxes if you recognize the picture of the medication you used. These medications are also called Yellow Footballs (when mixed with Ritalin it's also known as—Crackers, One & ones, Poor man's heroin, Ritz & T's, and T's & R's). | Each variable will be given a separate value<br><br>1 = Yes/Selected<br>0 = No/Not selected<br><br>OP9A = Talacen<br>OP9B = Talwin Compound<br>OP9C = Talwin NX<br>OP9D = Other pentazocine<br>OP9E = none | If OP9A = 1, enable OPRATE and go to OP9A30<br>If OP9B = 1, enable OPRATE and go to OP9B30<br>If OP9C = 1, enable OPRATE and go to OP9C30<br>. . . | | |
| OP9A30 | How many days in the past 30 days did you use Talacen in a way not prescribed by your doctor?<br><br>That is using it for how it made you feel and not to help with pain.<br><br>Days<br>None | | How many days in the past 30 days did you use Talacen in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP9A = 0) codes as 0 | | |

FIG. 6NNNN

| Question ID | Onscreen Text | Actor | Audio Recordings | ASI-MV Codes | Skip Logic | Consistency | Extreme Values |
|---|---|---|---|---|---|---|---|
| OP9AR1<br>OP9AR2<br>OP9AR3<br>OP9AR4<br>OP9AR5 | How have you usually used Talacen? Please select all that apply.<br><br>Swallowed<br>Snorted/Sniffed<br>Smoked<br>Injected in skin or muscle<br>Injected in vein | | How have you usually used Talacen? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP9AR1 = Swallowed<br>•<br>•<br>• | | | |
| OP9AW1<br>OP9AW2<br>OP9AW3<br>OP9AW4<br>OP9AW5<br>OP9AW6<br>OP9AW7<br>OP9AW8 | Where did you get the Talacen? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Talacen? Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP9AW1 = Own prescriptions<br>OP9AW2 = More than one Doctor<br>OP9AW3 = Internet shopping<br>OP9AW4 = Family<br>OP9AW5 = A dealer<br>OP9AW6 = Forgery<br>OP9AW7 = Stealing<br>OP9AW8 = Other | | | |

FIG. 6OOOO

| Question ID | Onscreen Text | Actor | Audio Recordings | ASI-MV Codes | Skip Logic | Consistency | Extreme Values |
|---|---|---|---|---|---|---|---|
| OP9B30 | How many days in the past 30 days did you use Talwin Compound in a way not prescribed by your doctor?<br><br>That is using it for how it made you feel and not to help with pain.<br><br>Days<br>None | | How many days in the past 30 days did you use Talwin Compound in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | If skipped (b/c OP9B = 0) codes as 0 | | |
| OP9BR1<br>OP9BR2<br>OP9BR3<br>OP9BR4<br>OP9BR5 | How have you usually used Talwin Compound? Please select all that apply.<br><br>Swallowed<br>Snorted/Sniffed<br>Smoked<br>Injected in skin or muscle<br>Injected in vein | | How have you usually used Talwin Compound?<br>Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP9BR1 = Swallowed<br>OP9BR2 = Snorted/Sniffed<br>OP9BR3 = Smoked<br>OP9BR4 = non-IV Injection<br>OP9BR5 = IV injection | | | |

FIG. 6PPPP

| Question ID | Onscreen Text | Actor | Audio Recordings | ASI-MV Codes | Skip Logic | Consistency | Extreme Values |
|---|---|---|---|---|---|---|---|
| OP9BW1<br>OP9BW2<br>OP9BW3<br>OP9BW4<br>OP9BW5<br>OP9BW6<br>OP9BW7<br>OP9BW8 | Where did you get the Talwin Compound? Please click on all that apply:<br><br>- Your own prescriptions (from one Dr.)<br>- Multiple Doctors (from several Drs or emergency services)<br>- internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Talwin Compound? Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP9BW1 = Own prescriptions<br>OP9BW2 = More than one Doctor<br>OP9BW3 = Internet shopping<br>OP9BW4 = Family<br>OP9BW5 = A dealer<br>OP9BW6 = Forgery<br>OP9BW7 = Stealing<br>OP9BW8 = Other | | | |
| OP9C30 | How many days in the past 30 days did you use Talwin NX in a way not prescribed by your doctor? That is using it for how it made you feel and not to help with pain.<br><br>Days<br>None | | How many days in the past 30 days did you use Talwin NX in a way not prescribed by your doctor? That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | If skipped (b/c OP9C = 0) codes as 0 | | |

FIG. 6QQQQ

| Question ID | Onscreen Text | Actor | Audio Recordings | ASI-MV Codes | Skip Logic | Consistency | Extreme Values |
|---|---|---|---|---|---|---|---|
| OP9CR1<br>OP9CR2<br>OP9CR3<br>OP9CR4<br>OP9CR5 | How have you usually used Talwin NX? Please click on all that apply.<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | How have you usually used Talwin NX? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP9CR1 = Swallowed<br>" "<br>" " | | | |
| OP9CW1<br>OP9CW2<br>OP9CW3<br>OP9CW4<br>OP9CW5<br>OP9CW6<br>OP9CW7<br>OP9CW8 | Where did you get the Talwin NX? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Talwin NX? Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP9CW1 = Own prescriptions<br>OP9CW2 = More than one Doctor<br>OP9CW3 = Internet shopping<br>OP9CW4 = Family<br>OP9CW5 = A dealer<br>OP9CW6 = Forgery<br>OP9CW7 = Stealing<br>OP9CW8 = Other | | | |

FIG. 6RRRR

| Question ID | Onscreen Text | Actor | Audio Recordings | ASI-MV Codes | Skip Logic | Consistency | Extreme Values |
|---|---|---|---|---|---|---|---|
| OP9D30 | How many days in the past 30 days did you use Other pentazocine in a way not prescribed by your doctor?<br><br>That is using it for how it made you feel and not to help with pain.<br><br>Days<br>None | | How many days in the past 30 days did you use Other pentazocine in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | If skipped (b/c OP9D = 0) codes as 0 | | |
| OP9DR1<br>OP9DR2<br>OP9DR3<br>OP9DR4<br>OP9DR5 | How have you usually used Other pentazocine? Please select all that apply.<br><br>Swallowed<br>Snorted/Sniffed<br>Smoked<br>Injected in skin or muscle<br>Injected in vein | | How have you usually used Other pentazocine?<br>Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP9DR1 = Swallowed<br>OP9DR2 = Snorted/Sniffed<br>OP9DR3 = Smoked<br>OP9DR4 = non-IV Injection<br>OP9DR5 = IV injection | | | |

FIG. 6SSSS

| Question ID | Onscreen Text | Actor | Audio Recordings | ASI-MV Codes | Skip Logic | Consistency | Extreme Values |
|---|---|---|---|---|---|---|---|
| <br>OP9EW1<br>OP9EW2<br>OP9EW3<br>OP9EW4<br>OP9EW5<br>OP9EW6<br>OP9EW7<br>OP9EW8 | Where did you get the Other pentazocine? Please click on all that apply.<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Other pentazocine? Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP9EW1 = Own prescriptions<br>OP9EW2 = More than one Doctor<br>OP9EW3 = Internet shopping<br>OP9EW4 = Family<br>OP9EW5 = A dealer<br>OP9EW6 = Forgery<br>OP9EW7 = Stealing<br>OP9EW8 = Other | | | |

FIG. 6TTTT

| Question ID | Onscreen Text | Actor | Audio Recordings | ASI-MV Codes | Skip Logic | Consistency | Extreme Values |
|---|---|---|---|---|---|---|---|
| OP10 (no screen = 10) OP10A = Darvocet OP10B = Darvon OP11C = Other propoxyphene OP11D = none | If you have taken Darvocet, Darvon or other propoxyphene in the past 30 days please select the appropriate boxes below. Remember to only select the boxes if you recognize the picture of the medications you used. These medications are also called D-cets. [IMAGE BOXES] Darvocet Darvon Other propoxyphene none | | If you have taken Darvocet, Darvon or other propoxyphene in the past 30 days please select the appropriate boxes below. If none, click here. Remember to only select the boxes if you recognize the picture of the medication you used. These medications are also called D-cets. | Each variable will be given a separate value 1 = Yes/Selected 0 = No/Not selected OP10A = Darvocet OP10B = Darvon OP10B = Other propoxyphene OP10C = none | If OP10A = 1, enable OPRATE and go to OP10A30 If OP11B = 1, enable OPRATE and go to OP10B30 If OP11C = 1, enable OPRATE and go to OP10B30 | | |
| OP10A30 | How many days in the past 30 days did you use Codeine in a way not prescribed by your doctor? That is using it for how it made you feel and not to help with pain. Days None | | How many days in the past 30 days did you use Codeine in a way not prescribed by your doctor? That is using it for how it made you feel and not to help with pain. Please click on the up or down arrow on the counter to show the number of days - or if None, click here. | Coded as 2 digit variable (MAX = 30) 0 = None (-1 = 0) | If skipped (b/c OP10A = 0) codes as 0 | | |

FIG. 6UUUU

| Question ID | Onscreen Text | Actor | Audio Recordings | ASI-MV Codes | Skip Logic | Consistency | Extreme Values |
|---|---|---|---|---|---|---|---|
| OP10AR1<br>OP10AR2<br>OP10AR3<br>OP10AR4<br>OP10AR5 | How have you usually used Darvocet? Please select all that apply.<br>Swallowed<br>Snorted/Sniffed<br>Smoked<br>Injected in skin or muscle<br>Injected in vein | | How have you usually used Darvocet? Please select all that apply.<br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br>OP10AR1 = Swallowed<br>•<br>•<br>• | | | |
| OP10AW1<br>OP10AW2<br>OP10AW3<br>OP10AW4<br>OP10AW5<br>OP10AW6<br>OP10AW7<br>OP10AW8 | Where did you get the Darvocet? Please click on all that apply:<br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Darvocet? Please click on all that apply.<br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br>OP10AW1 = Own prescriptions<br>OP10AW2 = More than one Doctor<br>OP10AW3 = Internet shopping<br>OP10AW4 = Family<br>OP10AW5 = A dealer<br>OP10AW6 = Forgery<br>OP10AW7 = Stealing<br>OP10AW8 = Other | | | |

FIG. 6VVVV

| Question ID | Onscreen Text | Actor | Audio Recordings | ASI-MV Codes | Skip Logic | Consistency | Extreme Values |
|---|---|---|---|---|---|---|---|
| OP10B30 | How many days in the past 30 days did you use Darvon in a way not prescribed by your doctor?<br><br>Days<br>None | | How many days in the past 30 days did you use Darvon in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | If skipped (b/c OP10B = 0) codes as 0 | | |
| OP10BR1<br>OP10BR2<br>OP10BR3<br>OP10BR4<br>OP10BR5 | How have you usually used Darvon? Please select all that apply.<br><br>Swallowed<br>Snorted/Sniffed<br>Smoked<br>injected in skin or muscle<br>injected in vein | | How have you usually used Darvon? Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP10BR1 = Swallowed<br>OP10BR2 = Snorted/Sniffed<br>OP10BR3 = Smoked<br>OP10BR4 = non-IV Injection<br>OP10BR5 = IV injection | | | |

FIG. 6WWWW

| Question ID | Onscreen Text | Actor | Audio Recordings | ASI-MV Codes | Skip Logic | Consistency | Extreme Values |
|---|---|---|---|---|---|---|---|
| OP10BW1<br>OP10BW2<br>OP10BW3<br>OP10BW4<br>OP10BW5<br>OP10BW6<br>OP10BW7<br>OP10BW8 | Where did you get the Darvon? Please click on all that apply.<br><br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Darvon? Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP10BW1 = Own prescriptions<br>OP10BW2 = More than one Doctor<br>OP10BW3 = Internet shopping<br>OP10BW4 = Family<br>OP10BW5 = A dealer<br>OP10BW6 = Forgery<br>OP10BW7 = Stealing<br>OP10BW8 = Other | | | |
| OP10C30 | How many days in the past 30 days did you use Other propoxyphene in a way not prescribed by your doctor?<br><br>That is using it for how it made you feel and not to help with pain.<br><br>Days<br>None | | How many days in the past 30 days did you use Other propoxyphene in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP12C = 0) codes as 0 | | |

FIG. 6XXXX

| Question ID | Onscreen Text | Actor | Audio Recordings | ASI-MV Codes | Skip Logic | Consistency | Extreme Values |
|---|---|---|---|---|---|---|---|
| OP10CR1<br>OP10CR2<br>OP10CR3<br>OP10CR4<br>OP10CR5 | How have you usually used Other propoxyphene? Please select all that apply.<br><br>Swallowed<br>Snorted/Sniffed<br>Smoked<br>Injected in skin or muscle<br>Injected in vein | | How have you usually used Other propoxyphene? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP10CR1 = Swallowed<br>•<br>•<br>• | | | |
| OP11AW1<br>OP11AW2<br>OP11AW3<br>OP11AW4<br>OP11AW5<br>OP11AW6<br>OP11AW7<br>OP11AW8 | Where did you get the Other propoxyphene? Please click on all that apply:<br><br>- Your own prescriptions (from one Dr.)<br>- Multiple Doctors (from several Drs or emergency services)<br>- internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Other propoxyphene? Please click on all that apply:<br><br>- Your own prescriptions (from one Dr.)<br>- Multiple Doctors (from several Drs or emergency services)<br>- internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP10CW1 = Own prescriptions<br>OP10CW2 = More than one Doctor<br>OP10CW3 = Internet shopping<br>OP10CW4 = Family<br>OP10CW5 = A dealer<br>OP10CW6 = Forgery<br>OP10CW7 = Stealing<br>OP10CW8 = Other | | | |

FIG. 6YYYY

| Question ID | Onscreen Text | Actor | Audio Recordings | ASI-MV Codes | Skip Logic | Consistency | Extreme Values |
|---|---|---|---|---|---|---|---|
| OP11 (no screen = 11) OP11A = Codeine OP11B = Tylenol with Codeine OP11C = none | If you have taken Codeine or Tylenol with Codeine in the past 30 days please select the appropriate boxes below. Remember to only select the boxes if you recognize the picture of the medications you used. These medications are also called T1s, T2s, T3s, and T4s. [IMAGE BOXES] Codeine Tylenol with Codeine none | | If you have taken Codeine or Tylenol with Codeine in the past 30 days please select the appropriate boxes below. If none, click here. Remember to only select the boxes if you recognize the picture of the medication you used. These medications are also called T1s, T2s, T3s, and T4s. | Each variable will be given a separate value 1 = Yes/Selected 0 = No/Not selected OP11A = Codeine OP11B = Tylenol with Codeine OP11C = none | If OP11A = 1, enable OPRATE and go to OP11A30 If OP11B = 1, enable OPRATE and go to OP11B30 If OP11C = 1, recode OP11A = 0 & OP11B = 0 If OP11A & OP11B = 0 go to OP12 | | |
| OP11A30 | How many days in the past 30 days did you use Codeine in a way not prescribed by your doctor? That is using it for how it made you feel and not to help with pain. Days None | | How many days in the past 30 days did you use Codeine in a way not prescribed by your doctor? That is using it for how it made you feel and not to help with pain. Please click on the up or down arrow on the counter to show the number of days - or if None, click here. | Coded as 2 digit variable (MAX = 30) 0 = None (-1 = 0) | If skipped (b/c OP11A = 0) codes as 0 | | |

FIG. 6ZZZZ

| Question ID | Onscreen Text | Actor | Audio Recordings | ASI-MV Codes | Skip Logic | Consistency | Extreme Values |
|---|---|---|---|---|---|---|---|
| OP11AR1<br>OP11AR2<br>OP11AR3<br>OP11AR4<br>OP11AR5 | How have you usually used Codeine? Please select all that apply.<br><br>Swallowed<br>Snorted/Sniffed<br>Smoked<br>Injected in skin or muscle<br>Injected in vein | | How have you usually used Codeine? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP11AR1 = | | | |
| OP11AW1<br>OP11AW2<br>OP11AW3<br>OP11AW4<br>OP11AW5<br>OP11AW6<br>OP11AW7<br>OP11AW8 | Where did you get the Codeine? Please click on all that apply.<br><br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Codeine? Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP11AW1 = Own prescriptions<br>OP11AW2 = More than one Doctor<br>OP11AW3 = Internet shopping<br>OP11AW4 = Family<br>OP11AW5 = A dealer<br>OP11AW6 = Forgery<br>OP11AW7 = Stealing<br>OP11AW8 = Other | | | |

FIG. 6AAAAA

| Question ID | Onscreen Text | Actor | Audio Recordings | ASI-MV Codes | Skip Logic | Consistency | Extreme Values |
|---|---|---|---|---|---|---|---|
| OP11B30 | How many days in the past 30 days did you use Tylenol with Codeine in a way not prescribed by your doctor?<br><br>That is using it for how it made you feel and not to help with pain.<br><br>Days<br>None | | How many days in the past 30 days did you use Tylenol with Codeine in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | If skipped (b/c OP11B = 0) codes as 0 | | |
| OP11BR1<br>OP11BR2<br>OP11BR3<br>OP11BR4<br>OP11BR5 | How have you usually used Tylenol with Codeine? Please select all that apply.<br><br>Swallowed<br>Snorted/Sniffed<br>Smoked<br>Injected in skin or muscle<br>Injected in vein | | How have you usually used Tylenol with Codeine? Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP11BR1 = Swallowed<br>OP11BR2 = Snorted/Sniffed<br>OP11BR3 = Smoked<br>OP11BR4 = non-IV Injection<br>OP11BR5 = IV injection | | | |

FIG. 6BBBBB

| Question ID | Onscreen Text | Actor | Audio Recordings | ASI-MV Codes | Skip Logic | Consistency | Extreme Values |
|---|---|---|---|---|---|---|---|
| OP11AW1<br>OP11AW2<br>OP11AW3<br>OP11AW4<br>OP11AW5<br>OP11AW6<br>OP11AW7<br>OP11AW8 | Where did you get the Tylenol with Codeine? Please click on all that apply:<br>- Your own prescriptions (from one Dr.)<br>- Multiple Doctors (from several Drs or emergency services)<br>- Internet shopping (without a doctor's visit)<br>- Family, friend or acquaintance<br>-A dealer(someone known to sell drugs)<br>- Prescription forgery (Writing or buying fake prescriptions)<br>- Stole them<br>- Other | | Where did you get the Tylenol with Codeine?<br>Please click on all that apply:<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP11AW1 = Own prescriptions<br>OP11AW2 = More than one Doctor<br>OP11AW3 = Internet shopping<br>OP11AW4 = Family<br>OP11AW5 = A dealer<br>OP11AW6 = Forgery<br>OP11AW7 = Stealing<br>OP11AW8 = Other | | | |
| OP12 (no screen = 12)<br>OP12A = Ultram<br>OP12B = Ultracet<br>OP12C = other tramadol<br>OP12D = none | If you have taken Ultram, Ultracet, or other tramadol in the past 30 days please select the appropriate boxes below.<br>Remember to only select the boxes if you recognize the picture of the medication you<br>. . .<br>. . . | | If you have taken Ultram, Ultracet, or other tramadol in the past 30 days please select the appropriate boxes below.<br>If none, click here.<br>Remember to only select the boxes if you recognize the picture of the medication you used. | Each variable will be given a separate value<br><br>1 = Yes/Selected<br>0 = No/Not selected<br><br>OP12A = Ultram<br>OP12B = Ultracet<br>OP12C = other tramadol<br>OP12D = none | If OP12A = 1, enable OPRATE and go to OP12A30<br>If OP12B = 1, enable OPRATE<br>. . .<br>. . . | | |

FIG. 6CCCCC

| Question ID | Onscreen Text | Actor | Audio Recordings | ASI-MV Codes | Skip Logic | Consistency | Extreme Values |
|---|---|---|---|---|---|---|---|
| OP12A30 | How many days in the past 30 days did you use Ultram in a way not prescribed by your doctor?<br><br>That is using it for how it made you feel and not to help with pain.<br><br>Days<br>None | | How many days in the past 30 days did you use Ultram in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | If skipped (b/c OP12A = 0) codes as 0 | | |
| OP12AR1<br>OP12AR2<br>OP12AR3<br>OP12AR4<br>OP12AR5 | How have you usually used Ultram?<br>Please select all that apply.<br><br>Swallowed<br>Snorted/Sniffed<br>Smoked<br>injected in skin or muscle<br>injected in vein | | How have you usually used Ultram?<br>Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP12AR1 = Swallowed<br>OP12AR2 = Snorted/Sniffed<br>OP12AR3 = Smoked<br>OP12AR4 = non-IV Injection<br>OP12AR5 = IV injection | | | |

FIG. 6DDDDD

| Question ID | Onscreen Text | Actor | Audio Recordings | ASI-MV Codes | Skip Logic | Consistency | Extreme Values |
|---|---|---|---|---|---|---|---|
| OP12AW1<br>OP12AW2<br>OP12AW3<br>OP12AW4<br>OP12AW5<br>OP12AW6<br>OP12AW7<br>OP12AW8 | Where did you get the Ultram? Please click on all that apply.<br><br>- Your own prescriptions (from one Dr.)<br>- Multiple Doctors (from several Drs or emergency services)<br>- internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Ultram? Please click on all that apply:<br><br>- Your own prescriptions (from one Dr.)<br>- Multiple Doctors (from several Drs or emergency services)<br>- internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP12AW1 = Own prescriptions<br>OP12AW2 = More than one Doctor<br>OP12AW3 = Internet shopping<br>OP12AW4 = Family<br>OP12AW5 = A dealer<br>OP12AW6 = Forgery<br>OP12AW7 = Stealing<br>OP12AW8 = Other | | | |
| OP12B30 | How many days in the past 30 days did you use Ultracet in a way not prescribed by your doctor?<br>That is using it for how it made you feel and not to help with pain.<br><br>Days<br>None | | How many days in the past 30 days did you use Ultracet in a way not prescribed by your doctor?<br>That is using it for how it made you feel and not to help with pain.<br>Please click on the up or down arrow on the counter to show the number of days - or if None, click here. | Coded as 2 digit variable (MAX = 30)<br><br>0 = None<br><br>(-1 = 0) | if skipped (b/c OP12B = 0) codes as 0 | | |

FIG. 6EEEEE

| Question ID | Onscreen Text | Actor | Audio Recordings | ASI-MV Codes | Skip Logic | Consistency | Extreme Values |
|---|---|---|---|---|---|---|---|
| OP12BR1<br>OP12BR2<br>OP12BR3<br>OP12BR4<br>OP12BR5 | How have you usually used Ultracet? Please select all that apply.<br><br>Swallowed<br>Snorted/Sniffed<br>Smoked<br>Injected in skin or muscle<br>Injected in vein | | How have you usually used Ultracet? Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP12BR1 =<br>• <br>• <br>• | | | |
| OP12BW1<br>OP12BW2<br>OP12BW3<br>OP12BW4<br>OP12BW5<br>OP12BW6<br>OP12BW7<br>OP12BW8 | Where did you get the Ultracet? Please click on all that apply:<br><br>- Your own prescriptions (from one Dr.)<br>- Multiple Doctors (from several Drs or emergency services)<br>- Internet shopping (without a doctor's visit)<br>- Family, friend or acquaintance<br>- A dealer(someone known to sell drugs)<br>- Prescription forgery (Writing or buying fake prescriptions)<br>- Stole them<br>- Other | | Where did you get the Ultracet? Please click on all that apply.<br><br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP12BW1 = Own prescriptions<br>OP12BW2 = More than one Doctor<br>OP12BW3 = Internet shopping<br>OP12BW4 = Family<br>OP12BW5 = A dealer<br>OP12BW6 = Forgery<br>OP12BW7 = Stealing<br>OP12BW8 = Other | | | |

FIG. 6FFFFF

| Question ID | Onscreen Text | Actor | Audio Recordings | ASI-MV Codes | Skip Logic | Consistency | Extreme Values |
|---|---|---|---|---|---|---|---|
| OP12C30 | How many days in the past 30 days did you use Other tramadol in a way not prescribed by your doctor?<br><br>That is using it for how it made you feel and not to help with pain.<br><br>Days<br>None | | How many days in the past 30 days did you use Other tramadol in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP12C = 0) codes as 0 | | |
| OP12CR1<br>OP12CR2<br>OP12CR3<br>OP12CR4<br>OP12CR5 | How have you usually used Other tramadol? Please select all that apply.<br><br>Swallowed<br>Snorted/Sniffed<br>Smoked<br>Injected in skin or muscle<br>Injected in vein | | How have you usually used Other tramadol? Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP12CR1 = Swallowed<br>OP12CR2 = Snorted/Sniffed<br>OP12CR3 = Smoked<br>OP12CR4 = non-IV Injection<br>OP12CR5 = IV injection | | | |

FIG. 6GGGGG

| Question ID | Onscreen Text | Actor | Audio Recordings | ASI-MV Codes | Skip Logic | Consistency | Extreme Values |
|---|---|---|---|---|---|---|---|
| OP12FW1<br>OP12FW2<br>OP12FW3<br>OP12FW4<br>OP12FW5<br>OP12FW6<br>OP12FW7<br>OP12FW8 | Where did you get the other tramadol? Please click on all that apply.<br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the other tramadol? Please click on all that apply.<br>- Your own prescriptions (from one Dr.)<br>- Multiple Doctors (from several Drs or emergency services)<br>- Internet shopping (without a doctor's visit)<br>- Family, friend or acquaintance<br>- A dealer or acquaintance<br>- Prescription forgery (Writing or buying fake prescriptions)<br>- Stole them<br>- Other | Each variable will be given a separate value<br><br>1 = Yes/Selected<br>0 = No/Not selected<br><br>OP12FW1 = Own prescriptions<br>OP12FW2 = More than one Doctor<br>OP12FW3 = Internet shopping<br>OP12FW4 = Family<br>OP12FW5 = A dealer<br>OP12FW6 = Forgery<br>OP12FW7 = Stealing<br>OP12FW8 = Other | | | |
| OP13 (no screen = 13)<br>OP13A = Subutex<br>OP13B = Suboxone<br>OP13C = other buprenorphine<br>OP13D = none | If you have taken Subutex, Suboxone or other buprenorphine in the past 30 days please select the appropriate boxes below.<br>Remember to only select the boxes if you recognize the picture of the medication you<br>.<br>.<br>. | | If you have taken Subutex, Suboxone or other buprenorphine in the past 30 days please select the appropriate boxes below.<br>If none of these, click here.<br>Remember to only select the boxes if you recognize the picture of the medication you used. | Each variable will be given a separate value<br><br>1 = Yes/Selected<br>0 = No/Not selected<br><br>OP13A = Subutex<br>OP13B = Suboxone<br>OP13C = other buprenorphine<br>OP13D = none | If OP13A = 1, enable OPRATE and go to OP13A30<br>If OP13B = 1, enable OPRATE and<br>.<br>.<br>. | | |

FIG. 6HHHHH

| Question ID | Onscreen Text | Actor | Audio Recordings | ASI-MV Codes | Skip Logic | Consistency | Extreme Values |
|---|---|---|---|---|---|---|---|
| OP13A30 | How many days in the past 30 days did you use Subutex in a way not prescribed by your doctor?<br><br>That is using it for how it made you feel and not to help with pain.<br><br>Days<br>None | | How many days in the past 30 days did you use Subutex in a way not prescribed by your doctor?<br><br>That is using it for how it made you feel and not to help with pain.<br><br>Please click on the up or down arrow on the counter to show the number of days - or if None, click here. | Coded as 2 digit variable (MAX = 30)<br><br>0 = None<br><br>(-1 = 0) | if skipped (b/c OP13A = 0) codes as 0 | | |
| OP13AR1<br>OP13AR2<br>OP13AR3<br>OP13AR4<br>OP13AR5 | How have you usually used Subutex?<br>Please select all that apply.<br>Swallowed<br>Snorted/Sniffed<br>Smoked<br>Injected in skin or muscle<br>Injected in vein | | How have you usually used Subutex?<br>Please select all that apply.<br><br>• Swallowed<br>• Snorted/Sniffed<br>• Smoked<br>• Injected in the skin or in the muscle<br>• Injected into a vein | Each variable will be given a separate value<br><br>1 = Yes/Selected<br>0 = No/Not selected<br><br>OP13AR1 = Swallowed<br>OP13AR2 = Snorted/Sniffed<br>OP13AR3 = Smoked<br>OP13AR4 = non-IV Injection<br>OP13AR5 = IV injection | | | |

FIG. 6IIIII

| Question ID | Onscreen Text | Actor | Audio Recordings | ASI-MV Codes | Skip Logic | Consistency | Extreme Values |
|---|---|---|---|---|---|---|---|
| OP13AW1<br>OP13AW2<br>OP13AW3<br>OP13AW4<br>OP13AW5<br>OP13AW6<br>OP13AW7<br>OP13AW8 | Where did you get the Subutex? Please click on all that apply:<br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Subutex? Please click on all that apply.<br>- Your own prescriptions (from one Dr.)<br>- Multiple Doctors (from several Drs or emergency services)<br>- Internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br>OP13AW1 = Own prescriptions<br>OP13AW2 = More than one Doctor<br>OP13AW3 = Internet shopping<br>OP13AW4 = Family<br>OP13AW5 = A dealer<br>OP13AW6 = Forgery<br>OP13AW7 = Stealing<br>OP13AW8 = Other | | | |
| OP13B30 | How many days in the past 30 days did you use Suboxone in a way not prescribed by your doctor? That is using it for how it made you feel and not to help with pain.<br>Days<br>None | | How many days in the past 30 days did you use Suboxone in a way not prescribed by your doctor? That is using it for how it made you feel and not to help with pain.<br>Please click on the up or down arrow on the counter to show the number of days - or if None, click here. | Coded as 2 digit variable (MAX = 30)<br>0 = None<br>(-1 = 0) | if skipped (b/c OP13B = 0) codes as 0 | | |

FIG. 6JJJJJ

| Question ID | Onscreen Text | Actor | Audio Recordings | ASI-MV Codes | Skip Logic | Consistency | Extreme Values |
|---|---|---|---|---|---|---|---|
| OP13BR1<br>OP13BR2<br>OP13BR3<br>OP13BR4<br>OP13BR5 | How have you usually used Suboxone? Please select all that apply.<br>Swallowed<br>Snorted/Sniffed<br>Smoked<br>Injected in skin or muscle<br>Injected in vein | | How have you usually used Suboxone?<br>Please select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>OP13BR1 =<br>•<br>•<br>• | | | |
| OP13BW1<br>OP13BW2<br>OP13BW3<br>OP13BW4<br>OP13BW5<br>OP13BW6<br>OP13BW7<br>OP13BW8 | Where did you get the Suboxone? Please click on all that apply:<br>- Your own prescriptions (from one Dr.)<br>- Multiple Doctors (from several Drs or emergency services)<br>- internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the Suboxone?<br>Please click on all that apply:<br><br>- Your own prescriptions (from one Dr.)<br>- Multiple Doctors (from several Drs or emergency services)<br>- internet shopping (without a doctor's visit)<br>- Family or friend<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br><br>OP13BW1 = Own prescriptions<br>OP13BW2 = More than one Doctor<br>OP13BW3 = Internet shopping<br>OP13BW4 = Family<br>OP13BW5 = A dealer<br>OP13BW6 = Forgery<br>OP13BW7 = Stealing<br>OP13BW8 = Other | | | |

FIG. 6KKKKK

| Question ID | Onscreen Text | Actor | Audio Recordings | ASI-MV Codes | Skip Logic | Consistency | Extreme Values |
|---|---|---|---|---|---|---|---|
| OP13C30 | How many days in the past 30 days did you use Other buprenorphine in a way not prescribed by your doctor? That is using it for how it made you feel and not to help with pain. Days None | | How many days in the past 30 days did you use Other buprenorphine in a way not prescribed by your doctor? That is using it for how it made you feel and not to help with pain. Please click on the up or down arrow on the counter to show the number of days - or if None, click here. | Coded as 2 digit variable (MAX = 30) 0 = None (-1 = 0) | If skipped (b/c OP13C = 0) codes as 0 | | |
| OP13CR1 OP13CR2 OP13CR3 OP13CR4 OP13CR5 | How have you usually used Other buprenorphine? Please select all that apply. Swallowed Snorted/Sniffed Smoked Injected in skin or muscle Injected in vein | | How have you usually used Other buprenorphine? Please select all that apply. • Swallowed • Snorted/Sniffed • Smoked • Injected in the skin or in the muscle • Injected into a vein | Each variable will be given a separate value 1 = Yes/Selected 0 = No/Not selected OP13CR1 = Swallowed OP13CR2 = Snorted/Sniffed OP13CR3 = Smoked OP13CR4 = non-IV Injection OP13CR5 = IV injection | | | |

FIG. 6LLLLL

| Question ID | Onscreen Text | Actor | Audio Recordings | ASI-MV Codes | Skip Logic | Consistency | Extreme Values |
|---|---|---|---|---|---|---|---|
| OP13DW1<br>OP13DW2<br>OP13DW3<br>OP13DW4<br>OP13DW5<br>OP13DW6<br>OP13DW7<br>OP13DW8 | Where did you get the other buprenorphine not shown? Please click on all that apply:<br>- Your own prescriptions (from one Dr.)<br>- Multiple Doctors (from several Drs or emergency services)<br>- Internet shopping (without a doctor's visit)<br>- Family, friend or acquaintance<br>- A dealer (someone known to sell drugs)<br>- Prescription forgery (Writing or buying fake prescriptions)<br>- Stole them<br>- Other | | Where did you get the other buprenorphine not shown? Please click on all that apply:<br>- Your own prescriptions (from one Dr.)<br>- Multiple Doctors (from several Drs or emergency services)<br>- Internet shopping (without a doctor's visit)<br>- Family or friend or acquaintance<br>- A dealer or acquaintance<br>- Prescription forgery (Writing or buying fake prescriptions)<br>- Stole them<br>- Other | Each variable will be given a separate value<br>1 = Yes/Selected<br>0 = No/Not selected<br>OP13DW1 = Own prescriptions<br>OP13DW2 = More than one Doctor<br>OP13DW3 = Internet shopping<br>OP13DW4 = Family<br>OP13DW5 = A dealer<br>OP13DW6 = Forgery<br>OP13DW7 = Stealing<br>OP13DW8 = Other | | | |
| OPOTHR | Have you used other opiate pain medications, but did not see them in the pictures shown to you?<br>Do not include non-opiate pain medication such as Vioxx, Celebrex, Motrin, Tylenol and Aleve.<br>- Yes<br>- No | | Have you used other opiate pain medications, but did not see them in the pictures shown to you?<br>Do not include non-opiate pain medication such as Vioxx, Celebrex, Motrin, Tylenol and Aleve.<br>- Yes<br>- No | 1 = Yes<br>0 = No | | | |

FIG. 6MMMMM

| Question ID | Onscreen Text | Actor | Audio Recordings | ASI-MV Codes | Skip Logic | Consistency | Extreme Values |
|---|---|---|---|---|---|---|---|
| OPRATE | Considering all the alcohol and drugs you use, how would you rank the opiate pain medications you selected:<br><br>- Primary or most serious problem<br>- Secondary or second most serious problem<br>- Tertiary or third most serious problem<br>- Not a problem for me | | Considering all the alcohol and drugs you use, how would you rank the opiate pain medications you selected:<br><br>- Primary or most serious problem<br>- Secondary or second most serious problem<br>- Tertiary or third most serious problem<br>- Not a problem for me | 0 = not a problem<br>1 = Primary problem<br>2 = Secondary problem<br>3 = Tertiary problem | | | |
| (ASID006D)<br>(Composite Question) | In the past 30 days, estimate how many days you used barbiturates.<br><br>Examples of barbiturates include: seconal, tuinol, Nembutal, Phenobarbital, florinal, fioricet, restoril, and pentobarbital.<br><br>Days<br>None | | In the past 30 days, estimate how many days you used barbiturates.<br><br>Examples of barbiturates include: seconal, tuinol, Nembutal, Phenobarbital, florinal, fioricet, restoril, and pentobarbital.<br><br>If None, click here. | Coded as 2 digit variable (MAX = 30)<br><br>0 = None<br><br>(-1 = 0) | - if skipped (b/c ASIDALLD = 0) codes as 0<br><br>If -2 (refused), show No-Skip Alert | If ASID006D > 0 and ASID015B = 0 or 2 Consistency Alert<br><br>If no: FLAG (if they don't change it, accept answer and add both questions and ... |  |

FIG. 6NNNNNN

| Question ID | Onscreen Text | Actor | Audio Recordings | ASI-MV Codes | Skip Logic | Consistency | Extreme Values |
|---|---|---|---|---|---|---|---|
| (ASID005Y) | Estimate the total number of years that you used barbiturates at least 3 days a week.<br><br>Please include prescribed and non-prescribed use.<br><br>Years<br><br>If less than 1 year choose one of the following:<br>Between 6 months and 1 year<br>Less than 6 months<br>Tried it a few times | | Estimate the total number of years that you used barbiturates at least 3 days a week.<br><br>Please include prescribed and non-prescribed use.<br><br>If less than 1 year choose one of the following:<br>• Between 6 months and 1 year<br>• Less than 6 months<br>• Tried it a few times | Coded as 2 digit variable<br>.7 = 6 mos -1 year<br>.5 = Less than 6 mos<br>0 = Tried it a few times<br>(-1 = 0)<br>(MAX value = AGE) | - if skipped (b/c ASIDALLD = 0) codes as 0 | | |
| D6c<br>D6R1<br>D6R2<br>D6R3<br>D6R4<br>D6R5 | How have you usually used barbiturates?<br><br>Please include prescribed and non-prescribed use.<br><br>Select all that apply.<br><br>Swallowed<br>Snorted/Sniffed<br>Smoked<br>Injected in skin or muscle<br>Injected in vein | | How have you usually used barbiturates?<br><br>Please include prescribed and non-prescribed use.<br><br>Select all that apply.<br><br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected<br><br>D6R1 = Swallowed<br>D6R2 = Snorted/Snorted/.<br>.<br>. | - if skipped (b/c prev questions are 0 ) code as -1 | | |

FIG. 600000

| Question ID | Onscreen Text | Actor | Audio Recordings | ASI-MV Codes | Skip Logic | Consistency | Extreme Values |
|---|---|---|---|---|---|---|---|
| (ASID007D) (Composite Question) | In the past 30 days, estimate how many days you used tranquilizers, sedatives or sleeping pills.<br><br>Examples of tranquilizers, sedatives or sleeping pills include: valium, Librium, Xanax, Ativan, thorazine, stelazine, stelazine, haldol, ambien, serax, and Quaaludes.<br><br>Days<br>None | | In the past 30 days, estimate how many days you used tranquilizers, sedatives or sleeping pills.<br><br>Examples of tranquilizers, sedatives or sleeping pills include: valium, Librium, Xanax, Ativan, thorazine, stelazine, haldol, ambien, serax, and Quaaludes.<br><br>If None, click this button. | Coded as 2 digit variable<br>(MAX = 30)<br><br>0 = None<br>(-1 = 0) | - if skipped (b/c ASIDALLE = 0) codes as 0<br><br>If -2 (refused), show No-Skip Alert | If ASID007D > 0 and ASID015B = 0 or 2 Consistency Alert<br><br>If no: FLAG (if they don't change it, accept answer | . . . |
| (ASID007Y) | Estimate the total number of years that you used tranquilizers, sedatives or sleeping pills at least 3 days a week.<br><br>Please include prescribed and non-prescribed use.<br><br>Years<br>If less than 1 year choose one of the following:<br>• Between 6 months and 1 year<br>• Less than 6 months<br>• Tried it a few times | | Estimate the total number of years that you used tranquilizers, sedatives or sleeping pills at least 3 days a week.<br><br>Please include prescribed and non-prescribed use.<br><br>If less than 1 year choose one of the following:<br>• Between 6 months and 1 year<br>• Less than 6 months<br>• Tried it a few times | Coded as 2 digit variable<br>.7 = 6 mos -1 year<br>.5 = Less than 6 mos<br>0 = Tried it a few times<br>(-1 = 0)<br>(MAX value = AGE) | - if skipped (b/c ASIDALLE = 0) codes as 0 | | |

FIG. 6PPPPP

| Question ID | Onscreen Text | Actor | Audio Recordings | ASI-MV Codes | Skip Logic | Consistency | Extreme Values |
|---|---|---|---|---|---|---|---|
| D7c | How have you usually used tranquilizers, sedatives or sleeping pills? | | How have you usually used tranquilizers, sedatives or sleeping pills? | Each variable will be given a separate value<br>1 = Yes/Selected<br>0 = No/Not selected | - If skipped (b/c prev questions are 0) code as -1 | | |
| D7R1<br>D7R2<br>D7R3<br>D7R4<br>D7R5 | Please include prescribed and non-prescribed use.<br>Please select all that apply.<br>Swallowed<br>Snorted/Sniffed<br>Smoked<br>Injected in skin or muscle<br>Injected in vein | | Please include prescribed and non-prescribed use.<br>Please select all that apply.<br>• Swallowed<br>• Snorted/Sniffed<br>• Smoked<br>• Injected in the skin or in the muscle<br>• Injected into a vein | D7R1 = Swallowed<br>D7R2 = Snorted/<br>•<br>•<br>• | | | |
| (ASID008D)<br>(Composite Question) | In the past 30 days, estimate how many days you used cocaine or crack.<br>Days<br>None | | In the past 30 days, estimate how many days you used cocaine or crack.<br>If None, click this button. | Coded as 2 digit variable<br>(MAX = 30)<br>0 = None<br>(-1 = 0) | - if skipped (b/c ASIDALLF = 0) codes as 0<br>If -2 (refused), show No-Skip Alert | If ASID008D > 0 and ASID015B = 0<br>•<br>• | |
| (ASID008Y) | Estimate the total number of years that you used cocaine or crack at least 3 days a week.<br>Years<br>If less than 1 year choose one of the following:<br>Between 6 months and 1 year<br>Less than 6 months<br>Tried it a few times | | Estimate the total number of years that you used cocaine or crack at least 3 days a week.<br>If less than 1 year choose one of the following:<br>• Between 6 months and 1 year<br>• Less than 6 months<br>• Tried it a few times | Coded as 2 digit variable<br>.7 = 6 mos -1 year<br>.5 = Less than 6 mos<br>0 = Tried it a few times<br>(-1 = 0) | - if skipped (b/c ASIDALLF = 0) codes as 0 | | |

FIG. 6QQQQ

| Question ID | Onscreen Text | Actor | Audio Recordings | ASI-MV Codes | Skip Logic | Consistency | Extreme Values |
|---|---|---|---|---|---|---|---|
| D8c<br><br>D8R1<br>D8R2<br>D8R3<br>D8R4<br>D8R5 | How have you usually used cocaine or crack?<br>Please select all that apply.<br>Swallowed<br>Snorted/Sniffed<br>Smoked<br>Injected in skin or muscle<br>Injected in vein | | How have you usually used cocaine or crack?<br>Please select all that apply.<br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected | - if skipped (b/c prev questions are 0 ) code as -1 | | |
| (ASID009D)<br><br>(Composite Question) | In the past 30 days, estimate how many days you used amphetamines or uppers.<br>Examples of amphetamines or uppers include: crank, ice, meth, Dexedrine, Ritalin or speed.<br>Days<br>None | | In the past 30 days, estimate how many days you used amphetamines or uppers.<br>Examples of amphetamines or uppers include: crank, ice, meth, Dexedrine, Ritalin or speed.<br>If None, click this button. | Coded as 2 digit variable<br>(MAX = 30)<br>0 = None<br>.<br>.<br>(-1 = 0) | - if skipped (b/c ASIDALLG = 0) codes as 0<br>If -2 (refused), show No-Skip Alert | If ASID009D > 0 and ASID015B = 0 or 2 Consistency Alert | |
| (ASID009Y) | Estimate the total number of years that you used amphetamines or uppers at least 3 days a week.<br>Please include prescribed and non-prescribed use.<br>Years<br>If less than 1 year choose one of the following:<br>• Between 6 months and 1 year<br>• Less than 6 months<br>• Tried it a few times | | Estimate the total number of years that you used amphetamines or uppers at least 3 days a week.<br>Please include prescribed and non-prescribed use.<br>If less than 1 year choose one of the following:<br>• Between 6 months and 1 year<br>• Less than 6 months<br>• Tried it a few times | Coded as 2 digit variable<br>.7 = 6 mos -1 year<br>.5 = Less than 6 mos<br>0 = Tried it a few times<br>.<br>.<br>(-1 = 0) | - if skipped (b/c ASIDALLG = 0) codes as 0 | | |

FIG. 6RRRRR

| Question ID | Actor | Onscreen Text | Audio Recordings | ASI-MV Codes | Skip Logic | Consistency | Extreme Values |
|---|---|---|---|---|---|---|---|
| D9c | | How have you usually used amphetamines or uppers? | How have you usually used amphetamines or uppers? | Each variable will be given a separate value 1 = Yes/Selected 0 = No/Not selected D9R1 = ... | - if skipped (b/c prev questions are 0 ) code as -1 | | |
| D9R1 | | Please select all that apply. | Please select all that apply. | | | | |
| D9R2 | | Swallowed | · Swallowed | | | | |
| D9R3 | | Snorted/Sniffed | · Snorted/Sniffed | | | | |
| D9R4 | | Smoked | · Smoked | | | | |
| D9R5 | | Injected in skin or muscle | · Injected in the skin or in the muscle | | | | |
| | | Injected in vein | · Injected into a vein | | | | |
| (ASID010D) (Composite Question) | | In the past 30 days, estimate how many days you used marijuana or hashish.<br><br>Days<br>None | In the past 30 days, estimate how many days you used marijuana or hashish.<br><br>If None, click this button. | Coded as 2 digit variable (MAX = 30)<br><br>0 = None<br>(-1 = 0) | - if skipped (b/c ASIDALLH = 0) codes as 0<br>If -2 (refused), show No-Skip Alert | If ASID010D > 0 and ASID015B = 0 ... | |
| (ASID010Y) | | Estimate the total number of years that you used marijuana or hashish at least 3 days a week.<br><br>Years<br><br>If less than 1 year choose one of the following:<br><br>· Between 6 months and 1 year<br>· Less than 6 months<br>· Tried it a few times | Estimate the total number of years that you used marijuana or hashish at least 3 days a week.<br><br>Please include prescribed and non-prescribed use.<br><br>If less than 1 year choose one of the following:<br><br>· Between 6 months and 1 year<br>· Less than 6 months<br>· Tried it a few times | Coded as 2 digit variable<br>.7 = 6 mos -1 year<br>.5 = Less than 6 mos<br>0 = Tried it a few times | - if skipped (b/c ASIDALLH = 0) codes as 0 | ... | |

FIG. 6SSSSS

| Question ID | Onscreen Text | Actor | Audio Recordings | ASI-MV Codes | Skip Logic | Consistency | Extreme Values |
|---|---|---|---|---|---|---|---|
| D10c | How have you usually used marijuana or hashish? | | How have you usually used marijuana or hashish? | Each variable will be given a separate value | | | |
| D10R1<br>D10R2<br>D10R3<br>D10R4<br>D10R5 | Please select all that apply.<br>Swallowed<br>Snorted/Sniffed<br>Smoked<br>Injected in skin or muscle<br>Injected in vein | | Please select all that apply.<br>• Swallowed<br>• Snorted/Sniffed<br>• Smoked<br>• Injected in the skin or in the muscle<br>• Injected in a vein | 1 = Yes/Selected<br>0 = No/Not selected<br>D10R1 =<br>.<br>.<br>. | - if skipped (b/c prev questions are 0 ) code as -1 | | |
| (ASID011D)<br>(Composite Question) | In the past 30 days, estimate how many days you used hallucinogens.<br>Examples of hallucinogens include: LSD or acid, PCP or angel dust, mescaline, or mushrooms.<br>Days<br>None | | In the past 30 days, estimate how many days you used hallucinogens.<br><br>Examples of hallucinogens include: LSD or acid, PCP or angel dust, mescaline, or mushrooms.<br><br>If None, click this button. | Coded as 2 digit variable<br>(MAX = 30)<br><br>0 = None<br><br>(-1 = 0) | - if skipped (b/c ASIDALLI = 0) codes as 0<br><br>If -2 (refused), show No-Skip Alert | If ASID011D > 0 and ASID015B = 0 or 2 Consistency Alert<br>If no: FLAG<br>.<br>.<br>. | |
| (ASID011Y) | Estimate the total number of years that you used hallucinogens at least 3 days a week.<br>Years<br>If less than 1 year choose one of the following:<br>Between 6 months and 1 year<br>Less than 6 months<br>Tried it a few times | | Estimate the total number of years that you used hallucinogens at least 3 days a week.<br>If less than 1 year choose one of the following:<br><br>• Between 6 months and 1 year<br>• Less than 6 months<br>• Tried it a few times | Coded as 2 digit variable<br>.7 = 6 mos - 1 year<br>.5 = Less than 6 mos<br>0 = Tried it a few times<br>.<br>.<br>. | - if skipped (b/c ASIDALLI = 0) codes as 0 | | |

FIG. 6TTTTT

| Question ID | Onscreen Text | Actor | Audio Recordings | ASI-MV Codes | Skip Logic | Consistency | Extreme Values |
|---|---|---|---|---|---|---|---|
| D11c<br>D11R1<br>D11R2<br>D11R3<br>D11R4<br>D11R5 | How have you usually used hallucinogens like LSD, mushrooms, or acid? Please select all that apply.<br>Swallowed<br>Snorted/Sniffed<br>Smoked<br>Injected in skin or muscle<br>Injected in vein | | How have you usually used hallucinogens like LSD, mushrooms, or acid? Please select all that apply.<br>• Swallowed<br>• Snorted/Sniffed<br>• Smoked<br>• Injected in the skin or in the muscle<br>• Injected into a vein | Each variable will be given a separate value<br>1 = Yes/Selected<br>0 = No/Not selected | - if skipped (b/c prev questions are 0 ) code as -1 | | |
| (ASID012D)<br>(Composite Question) | In the past 30 days, estimate how many days you used inhalants.<br>Examples of inhalants include: airplane glue, gasoline, nitrous oxide, whippets or poppers.<br>Days<br>None | | In the past 30 days, estimate how many days you used inhalants.<br>Examples of inhalants include: airplane glue, gasoline, nitrous oxide, whippets or popper.<br>If None, click this button. | Coded as 2 digit variable<br>(MAX = 30)<br>0 = None<br>(-1 = 0) | - if skipped (b/c ASIDALLJ = 0) codes as 0<br>If -2 (refused), show No-Skip Alert | If ASID012D > 0 and ASID015B = 0 or 2 Consistency Alert | |
| (ASID012Y) | Estimate the total number of years that you used inhalants at least 3 days a week.<br>Years<br>If less than 1 year choose one of the following:<br>Between 6 months and 1 year<br>Less than 6 months<br>Tried it a few times | | Estimate the total number of years that you used inhalants at least 3 days a week.<br>If less than 1 year choose one of the following:<br>• Between 6 months and 1 year<br>• Less than 6 months<br>• Tried it a few times | Coded as 2 digit variable<br>.7 = 6 mos -1 year<br>.5 = Less than 6 mos<br>0 = Tried it a few | - if skipped (b/c ASIDALLJ = 0) codes as 0 | | |
| (ASID012R) | NO SCREEN—populated only if ASID012D and ASID012Y are asked | | | If ASID012D > 0 or ASID012Y > 0, ASID12R = 2 | | | |

FIG. 6UUUUU

| Question ID | Onscreen Text | Actor | Audio Recordings | ASI-MV Codes | Skip Logic | Consistency | Extreme Values |
|---|---|---|---|---|---|---|---|
| (ASID013D) (Composite Question) | In the past 30 days, estimate how many days you used more than one substance, including alcohol, in the same day. Days None | | In the past 30 days, estimate how many days you used more than one substance, including alcohol, in the same day. If None, click this button. | Coded as 2 digit variable 0 = None If ASIDALLK = 1, ASID013D is skipped and coded as 0 (-1 = 0) | If -2 (refused), show No-Skip Alert | If ASID013D > 0 and ASID015B = 0 or 2 Consistency Alert | |
| (ASID013Y) | Estimate the total number of years you used more than one substance, including alcohol, at least 3 times a week. Years If less than 1 year choose one of the following: Between 6 months and 1 year Less than 6 months Tried it a few times None | | Estimate the total number of years you used more than one substance, including alcohol, at least 3 times a week. If less than 1 year choose one of the following: • Between 6 months and 1 year • Less than 6 months • Tried it a few times • None | Coded as 2 digit variable .7 = 6 mos -1 year .5 = Less than 6 mos 0 = Tried it a few times (-1 = 0) (MAX value = AGE) | | | |
| (ASID024) | In the past 30 days, how much money have you spent on drugs? None | | In the past 30 days, how much money have you spent on drugs? If None, click here. | Coded as 5 digit variable 0 = None (-1 = 0) | | | If ASID024 > 3000, Extreme Alert |

FIG. 6VVVVV

| Question ID | Onscreen Text | Actor | Audio Recordings | ASI-MV Codes | Skip Logic | Consistency | Extreme Values |
|---|---|---|---|---|---|---|---|
| (ASID014P) | Of the substances you reported using, which one is the primary or most serious problem for you?<br><br>-ALCOHOL<br>-Heroin<br>-Methadone or LAAM<br>-Other opiates or painkillers like morphine, darvon, percodan, vicodin, talwin, dilaudid, or codeine<br>-Barbiturates like seconal, tuinol, Nembutal,<br>-Phenobarbital and fiorinal, (also known as barbs, reds and yellows)<br>-Sedatives, tranquilizers or sleeping pills like valium, Librium, Xanax, Ativan, ambien, serax, and Quaaludes (also known as downers or tranks)<br>-Cocaine or Crack<br>-Amphetamines or uppers like crank, ice, meth, Ritalin, Dexedrine, speed, or other<br>*<br>* | | Of the substances you reported using, which one is primary or most serious problem for you?<br><br>• ALCOHOL<br>• Heroin<br>• Methadone or LAAM<br>• Other opiates or painkillers like morphine, darvon, percodan, vicodin, talwin, dilaudid, or codeine<br>• Barbiturates like seconal, tuinol, Nembutal. Phenobarbital and fiorinal, (also known as barbs, reds and yellows)<br>• Sedatives, tranquilizers or sleeping pills like valium, Librium, Xanax, Ativan, ambien, serax, and Quaaludes (also known as downers or tranks)<br>• Cocaine or Crack<br>• Amphetamines or uppers like crank, ice, meth, Ritalin, Dexedrine, speed, or other stimulants<br>• Marijuana or hashish<br>• Hallucinogens like LSD or acid, PCP or angel dust, mescaline, or mushrooms<br>• inhalants like glue, gasoline, nitrous oxide, whippets, or poppers<br>• None | Coded by number for substance<br><br>- None = 0<br>- Alcohol = 2<br>- Heroin = 3<br>- Methadone = 4<br>- Other Opiates = 5<br>- Barbs = 6<br>- Sedatives = 7<br>- Cocaine = 8<br>- Amphetamines = 9<br>- Marijuana = 10<br>- Hallucinogens = 11<br>- Inhalants = 12<br><br>(-1=0) | If ASID014 is NOT = 2 (if alcohol is not selected), go to ASID014A<br><br>If ASID014 = 1 (alcohol is selected), go to ASID015A | | |

FIG. 6WWWWW

| Question ID | Onscreen Text | Actor | Audio Recordings | ASI-MV Codes | Skip Logic | Consistency | Extreme Values |
|---|---|---|---|---|---|---|---|
| (ASID014S) | Of the other substances you reported using, which one is the secondary or second most serious problem for you?<br><br>-ALCOHOL<br>-Heroin<br>-Methadone or LAAM<br>-Other opiates or painkillers like morphine, darvon, percodan, vicodin, talwin, dilaudid, or codeine<br>-Barbiturates like seconal, tuinol, Nembutal, Phenobarbital and fiorinal, (also known as barbs, reds and yellows)<br>-Sedatives, tranquilizers or sleeping pills like valium, Librium, Xanax, Ativan, ambien, serax, and Quaaludes (also known as downers or tranks)<br>-Cocaine or Crack<br>-Amphetamines or uppers like crank, ice, meth, Ritalin, Dexedrine, speed, or other | | Of the other substances you reported using, which one is the secondary or second most serious problem for you?<br><br>• ALCOHOL<br>• Heroin<br>• Methadone or LAAM<br>• Other opiates or painkillers like morphine, darvon, percodan, vicodin, talwin, dilaudid, or codeine<br>• Barbiturates like seconal, tuinol, Nembutal, Phenobarbital and fiorinal, (also known as barbs, reds and yellows)<br>• Sedatives, tranquilizers or sleeping pills like valium, Librium, Xanax, Ativan, serax, and Quaaludes (also known as downers or tranks)<br>• Cocaine or Crack<br>• Amphetamines or uppers like crank, ice, meth, Ritalin, Dexedrine, speed, or other stimulants<br>• Marijuana or hashish<br>• Hallucinogens like LSD or acid, PCP or angel dust, mescaline, or mushrooms<br>• Inhalants like glue, gasoline, nitrous oxide, whippets, or poppers<br>• None | Coded by number for substance<br><br>- None = 0<br>- Alcohol = 2<br>- Heroin = 3<br>- Methadone = 4<br>- Other Opiates = 5<br>- Barbs = 6<br>- Sedatives = 7<br>- Cocaine = 8<br>- Amphetamines = 9<br>- Marijuana = 10<br>- Hallucinogens = 11<br>- Inhalants = 12<br><br>(-1=0) | | | |

FIG. 6XXXXX

| Question ID | Onscreen Text | Actor | Audio Recordings | ASI-MV Codes | Skip Logic | Consistency | Extreme Values |
|---|---|---|---|---|---|---|---|
| (ASID014) | NO SCREEN CALCULATED VARIABLE | | | If ASID014P =2 thru 12 and ASID014S = 0, code ASID014=ASI DO14P<br><br>If ASID014P=0 | | | |
| (ASID015A) | Was there ever a time when you were not using your major or primary substance for at least a month or more?<br><br>Do not include times when you could not use because you were in prison or in a hospital.<br><br>Yes<br>No | | Was there ever a time when you were not using your major or primary substance for at least a month or more?<br><br>Do not include times when you could not use because you were in prison or in a hospital.<br><br>Click Yes or No. | 1 = Yes<br>0 = No | If ASID015A = 0, go to ASID017<br>If ASID015A = 1, go to ASID015 | | |
| (ASID015) | How long ago were you able to stay clean and sober on your own?<br><br>Year<br>Month<br>Less than a month | | How long were you able to stay clean and sober on your own?<br><br>If less than a month ago, click this button | Year/month counter So (year X12) + months = total | | | |

FIG. 6YYYYY

| Question ID | Onscreen Text | Actor | Audio Recordings | ASI-MV Codes | Skip Logic | Consistency | Extreme Values |
|---|---|---|---|---|---|---|---|
| (ASID015B) | Are you currently clean and sober?<br><br>Yes, clean and sober for a month or more<br>Yes, clean and sober for less than a month<br>No | | Are you currently clean and sober?<br><br>• Yes, clean and sober for a month or more<br>• Yes, clean and sober for less than a month<br>• No | Yes, clean for 1 month = 1<br>Yes, clean for less than one month = .1<br>No = 0 | If ASID015B > 0, go to ASID017<br><br>If ASID15B = 0, go to ASID016 | | |
| (ASID016) | How long ago did you begin using again?<br>Year<br>Month<br>Less than a month ago | | How long ago did you begin using again?<br><br>If it was less than a month ago, click this button. | Year/month counter So (year X12) + months = total months | | | |
| (ASID017) | How many times have you had DTs?<br>[Side bar]<br>That is one or two days after you stopped or cut down heavy drinking and felt confused, agitated, feverish, and saw things, hear voices or felt things crawling on you.<br><br>Times [2 digit counter]<br>Never | | How many times have you had DTs?<br><br>That is one or two days after you stopped or cut down heavy drinking and felt confused, agitated, feverish, and saw things, hear voices or felt things crawling on you.<br><br>If you never had DTs, click this button. | Coded as 2 digit variable<br><br>0 = None (never had DTs) | | | If ASID017 > 5, Extreme Alert and if not changed, add question and answer to the Extreme Values Report |

FIG. 6ZZZZZ

| Question ID | Onscreen Text | Actor | Audio Recordings | ASI-MV Codes | Skip Logic | Consistency | Extreme Values |
|---|---|---|---|---|---|---|---|
| (ASID017) F/up | Since the last time you took this ASI interview, how many times have you had DTs? [Side bar] That is, one or two days after you stopped or cut down heavy drinking and felt confused, agitated, feverish, and saw things, heard voices or felt things crawling on you. Times (counter) NONE | | Since the last time you took this ASI interview, how many times have you had DTs? That is, one or two days after you stopped or cut down heavy drinking and felt confused, agitated, feverish, and saw things, heard voices or felt things crawling on you. Times NONE or no times since last interview | Coded as 2 digit variable 0 = NONE or no times since last interview | | | If ASID017> 5, Extreme Alert and if not changed, add question and answer to the Extreme Values Report |
| (ASID018) | How many times have you overdosed on drugs seriously enough that you needed someone else's help to recover – not just sleeping it off? [Side bar] Include suicide attempts by overdosing. Times (counter) Never | | How many times have you overdosed on drugs seriously enough that you needed someone else's help to recover – not just sleeping it off? Include suicide attempts by overdosing. If Never, click this button. | Coded as 2 digit variable 0 = Never | | | If ASID018> 5, Extreme Alert and if not changed, add question and answer to the Extreme Values Report |

FIG. 6AAAAAA

| Question ID | Onscreen Text | Actor | Audio Recordings | ASI-MV Codes | Skip Logic | Consistency | Extreme Values |
|---|---|---|---|---|---|---|---|
| (ASID018)<br>F/up | Since the last time you took this ASI interview, how many times have you overdosed on drugs seriously enough that you needed someone else's help to recover – not just sleeping it off?<br>[Side bar]<br>Include suicide attempts by overdosing.<br>Times (counter)<br>NONE | | Since the last time you took this ASI interview, how many times have you overdosed on drugs seriously enough that you needed someone else's help to recover – not just sleeping it off?<br>Include suicide attempts by overdosing.<br>Times<br>NONE or no times since last interview | Coded as 2 digit variable<br><br>0 = NONE or no times since last interview | | | If ASID018> 5, Extreme Alert and if not changed, add question and answer to the Extreme Values Report |
| (ASID025) | In the past 30 days, about how many days did you attend any outpatient treatment or counseling for alcohol or drug problems.<br>Do not include days you attended AA, NA, or other self-help meetings.<br>Days<br>None | | In the past 30 days, about how many days did you attend any outpatient treatment or counseling for alcohol or drug problems.<br>Do not include days you attended AA, NA, or other self-help meetings.<br>If None, click this button. | Coded as 2 digit variable (MAX = 30)<br><br>0 = NONE<br>FINAL code for ASID025 = RESPONSE TO ASID025 + ASID025A (MAX = 30) | | | |
| (ASID025A) | In the past 30 days, estimate how many days you attended self-help meetings such as AA, NA, or CA.<br>Days<br>None | | In the past 30 days, estimate how many days you attended self-help meetings such as AA, NA, or CA.<br>If None, click this button. | Coded as 2 digit variable (MAX = 30)<br><br>0 = None | | | |

FIG. 6BBBBB

| Question ID | Onscreen Text | Actor | Audio Recordings | ASI-MV Codes | Skip Logic | Consistency | Extreme Values |
|---|---|---|---|---|---|---|---|
| | About how many different times in your life have you entered treatment for the following: | | About how many different times in your life have you entered treatment for the following: | | | | |
| (ASID019) | [Side bar] Include detox, halfway houses, inpatient and outpatient counseling, and periods where you attended AA or NA at least three times a month. Also, include treatment received in prison. | | • Alcohol only<br>• Drugs only<br>• Both alcohol and drugs | CODING RULES ASID019 = alcohol only + both drug and alcohol | If ASID019 and ASID020 = 0, go to ASID026 | | If ASID019 > 15, Extreme Alert and if not changed, add question and answer to the Extreme Values Report |
| (ASID020) | Counters/Buttons<br>- I have been in treatment for alcohol problem (not drugs)<br>- I have been in treatment for drug problem (not alcohol)<br>- I have been in treatment for both alcohol and drug problems<br>Never been in treatment | | Include detox, halfway houses, inpatient and outpatient counseling, and periods where you attended AA or NA at least three times a month.<br><br>Also, include treatment received in prison.<br><br>If you have never been in treatment before, click this button. | ASID020 = drug only + both drug and alcohol<br><br>Never been in tx = ASID019 = 0 & ASID020 = 0 | | If ASIG019 = 3, and ASID019 + ASID020 = 0, FLAG | If ASID020 > 15, Extreme Alert and if not changed, add question and answer to the Extreme Values Report |

FIG. 6CCCCCC

| Question ID | Onscreen Text | Actor | Audio Recordings | ASI-MV Codes | Skip Logic | Consistency | Extreme Values |
|---|---|---|---|---|---|---|---|
| (ASID019) (ASID020) F/up | Since the last time you took this ASI interview, about how many different times have you entered treatment for the following: [Side bar] Include detox, halfway houses, inpatient and outpatient counseling, and periods where you attended AA or NA at least three times a month. Also, include treatment received in prison. Counters/Buttons - I have been in treatment for alcohol problem (not drugs) - I have been in treatment for drug problem (not alcohol) - I have been in treatment for both alcohol and drug problems Never been in treatment | | Since the last time you took this ASI interview, about how many different times have you entered treatment for the following: -Alcohol only -Drugs only -Both alcohol and drugs Include detox, halfway houses, inpatient and outpatient counseling, and periods where you attended AA or NA at least three times a month. Also, include treatment received in prison. If you have not been in treatment since the last time you were interviewed, click this button. | CODING RULES ASID019 = alcohol only + both drug and alcohol ASID020 = drug only + both drug and alcohol Never been in tx = ASID019 = 0 & ASID020 = 0 | If ASID019 & ASID020 = 0, go to ASID026 | | If ASID019 > 15, Extreme Alert and if not changed, add question and answer to the Extreme Values Report If ASID020 > 15, Extreme Alert and if not changed, add question and answer to the Extreme Values Report |

FIG. 6DDDDD

| Question ID | Onscreen Text | Actor | Audio Recordings | ASI-MV Codes | Skip Logic | Consistency | Extreme Values |
|---|---|---|---|---|---|---|---|
| (ASID021) (ASID022) | Estimate how many of these treatments were for detox only. Counters/Buttons Estimate how many of the alcohol treatments were detox only. Estimate how many of the drug treatments were detox only. Estimate how many of the alcohol and drug treatments were detox only. Never been in treatment | | • Estimate how many of the alcohol treatments were detox only. <br>• Estimate how many of the drug treatments were detox only. <br>• Estimate how many of the alcohol and drug treatments were detox only. <br>If you've never been in detox, click this button. | CODING RULES ASID021 = alcohol only + both drug and alcohol <br><br>ASID022 = drug only + both drug and alcohol <br><br>Never been in tx = ASID021 = 0 & • • • | | | If ASID021 > 10, Extreme Alert and if not changed, add question and answer to the Extreme Values Report <br><br>If ASID022 > 10, Extreme Alert and if not changed, add question and answer to the Extreme Values Report |
| (ASID021) (ASID022) F/up | Since the last time you took this ASI interview, estimate how many of these treatments were for detox only. Counters/Buttons Estimate how many of the alcohol treatments were detox only. Estimate how many of the drug treatments were detox only. | | Since the last time you took this ASI interview <br><br>Estimate how many of the alcohol treatments were detox only. <br><br>Estimate how many of the drug treatments were detox only. <br><br>Estimate how many of the alcohol and drug treatments were detox only. <br><br>If you've never been in detox, click this button. | CODING RULES ASID021 = alcohol only + both drug and alcohol <br><br>ASID022 = drug only + both drug and alcohol <br><br>Never been in tx = ASID021 = 0 & • • • | | | If ASID021 > 10, Extreme Alert and if not changed, add question and answer to the Extreme Values Report <br><br>If ASID022 > 10, Extreme Alert and if not changed, add question and answer to the Extreme Values Report |

FIG. 6EEEEE

| Question ID | Onscreen Text | Actor | Audio Recordings | ASI-MV Codes | Skip Logic | Consistency | Extreme Values |
|---|---|---|---|---|---|---|---|
| (ASID026) (Composite Question) | In the past 30 days, about how many days have you had problems related to drinking alcohol. [Side bar] Examples of problems include: craving or strong urges to drink, withdrawal or sickness, not being able to stop drinking, arguments or poor work performance. Days None | | In the past 30 days, about how many days have you had problems related to drinking alcohol. Examples of problems include: craving or strong urges to drink, withdrawal or sickness, not being able to stop drinking, arguments or poor work performance. If None, click here. | Coded as 2 digit variable (MAX = 30) 0 = None | | If ASID026 > 0 and ASID028 =0 Consistency Alert If no: FLAG (if they don't change it, accept answer and add both questions and answers to Consistency Report and Sum in CONSISTotal variable) | |
| (ASID028) (Composite Question) | In the past 30 days, how troubled or bothered have you been by alcohol problems? Not at all Slightly Moderately Considerably Extremely | | In the past 30 days, how troubled or bothered have you been by alcohol problems? • Not at all • Slightly • Moderately • Considerably • Extremely | 0 = Not at all 1 = Slightly 2 = Moderately 3 = Considerably 4 = Extremely | If -2 (refused), show No-Skip Alert | If ASID026 > 0 and ASID028 =0 Consistency Alert If ASID026 > 0 and ASID030 = 0 • • • | |
| (ASID030) (Composite Question) | How important is it to you now to receive treatment for alcohol problems? Not at all • • • | | How important is it to you now to receive treatment for alcohol problems? • Not at all • • • | 0 = Not at all 1 = Slightly 2 = Moderately 3 = Considerably 4 = Extremely | If -2 (refused), show No-Skip Alert | If ASID026 = 0 and ASID030 or ASID028 > 1 Consistency Alert If no: FLAG • • • | |

FIG. 6FFFFF

| Question ID | Onscreen Text | Actor | Audio Recordings | ASI-MV Codes | Skip Logic | Consistency | Extreme Values |
|---|---|---|---|---|---|---|---|
| (ASID027) (Composite Question) | In the past 30 days, about how many days have you had problems related to using drugs. [Side bar] Examples include: craving or strong urges to use drugs, withdrawal or sickness, not being able to stop using drugs, arguments or poor work performance. Days None | | In the past 30 days, about how many days have you had problems related to using drugs. Examples include: craving or strong urges to use drugs, withdrawal or sickness, not being able to stop using drugs, arguments or poor work performance If None, click here. | Coded as 2 digit variable (MAX = 30) 0 = None | | | |
| (ASID029) (Composite Question) | In the past 30 days, how troubled or bothered have you been by drug problems? Not at all Slightly Moderately Considerably Extremely | | In the past 30 days, how troubled or bothered have you been by drug problems? • Not at all • Slightly • Moderately • Considerably • Extremely | 0 = Not at all 1 = Slightly 2 = Moderately 3 = Considerably 4 = Extremely | If -2 (refused), show No-Skip Alert | | |
| (ASID031) (Composite Question) | How important is it to you now to receive treatment for drug problems? Not at all • • • | | How important is it to you now to receive treatment for drug problems? • Not at all • • • | 0 = Not at all 1 = Slightly 2 = Moderately 3 = Considerably 4 = Extremely | If -2 (refused), show No-Skip Alert | | |

FIG. 6GGGGGG

| Question ID | Onscreen Text | Actor | Audio Recordings | ASI-MV Codes | Skip Logic Consistency Extreme Values |
|---|---|---|---|---|---|
| (ASID032) | | | | (Calculated Variable) Alcohol Severity Rating | Recode: ASID001Y .5 = 0; .7 = 1 See Severity Ratings COMPUTE alcurr = ASID001D + ASID002D + ASID026. COMPUTE alcdura = ASID001Y + ASID002. COMPUTE ASD032 = (ASID030 * .976) + (alcdura * .02974) + (alcurr * .01357) + (ASID028 * .23) + 1.469 . Round ASD032 to nearest whole number. If <= 1.5 then 0 if > 1.51 OR <1.99 then 1 If >= 9 then 9 Otherwise regular rounding |
| (ASID033) | | | | (Calculated Variable) Drug Severity Rating | Recode: ASID003Y, ASID004Y, ASID005Y, ASID006Y, ASID007Y, ASID008Y, ASID009Y, ASID010Y, ASID011Y, ASID012Y, ASID013Y .5 = 0; .7 = 1 COMPUTE drugsev = ASID003D + ASID004D + ASID005D + ASID006D + ASID007D + ASID008D + ASID009D + ASID010D + ASID011D + ASID012D + ASID013D + ASID027 .compute drugnua = ASID003Y + ASID004Y + ASID005Y + ASID006Y + ASID007Y + ASID008Y + ASID009Y + ASID010Y + ASID011Y + ASID012Y + ASID013Y. COMPUTE ASID033 = (ASID031 * .996) + (drugnua * .01189) + (ASID029 * .182) + (drugsev * .004416) + 2.414 . Round ASD033 to nearest whole number. If <= 2.414 then 0 If > 2.415 OR < 2.62 then 1 If > 2.63 OR < 2.99 then 2 If > 3 OR < 3.5 then 3 if >8 then 9 Otherwise regular rounding |

FIG. 6HHHHHHH

| Question ID | Onscreen Text | Actor | Audio Recordings | ASI-MV Codes | Skip Logic | Consistency | Extreme Values |
|---|---|---|---|---|---|---|---|
| COMPALC (Calculated Variable) | | | | Alcohol Composite Score (.000-1.000) | Variables in data base:<br>asid001d : Days drank alcohol past 30 days<br>asid002d : Drink at least 5 drinks past 30 days<br>asid023 : Money spent on alcohol past 30 days<br>asid026 : Problems related to drinking past 30 days<br>asid028 : Troubled or bothered by alcohol past 30 days<br>asid030 : How important is treatment for alcohol problems<br>New variables:<br>LOGALC : Natural Log of variable asid020a<br>ALCOHOL : Temporary variable<br>COMPALC : Alcohol Composite Score<br>Recode: asid001d asid002d asid023 asid026 asid028 asid030 (-1) = 0 (-2) = missing (or blank)<br>Formulas:<br>IF (asid023 > 0) Then LOGALC = LN(asid023 ) / 44.<br>IF (asid023 = 0) Then LOGALC = 0<br>ALCOHOL = ( asid001d / 180)+( asid002d / 180)+( asid026 / 180) + ( asid028 / 24) + (asid030 / 24) .<br>COMPALC = ALCOHOL + LOGALC<br>RECODE: If >= 1.00 then 1.00 | | |

FIG. 6IIIII

| Question ID | Onscreen Text | Actor | Audio Recordings | ASI-MV Codes | Skip Logic | Consistency | Extreme Values |
|---|---|---|---|---|---|---|---|
| COMPDRUG (Calculated Variable) | | | | Drug Composite Score (.000-1.000) | asid010d asid011d asid013d asid027 asid029 asid031 (-1) = 0(-2) = missing (or blank) Formula: COMPDRUG = (asid003d / 390) + (asid004d / 390) + (asid005d / 390) + (asid006d/390) + (asid007d / 390) + (asid008d / 390) + (asid009d / 390) + (asid010d / 390) + (asid011d / 390) + (asid013d / 390) + (asid027 / 390) + (asid029 / 52) + (asid031/ 52). RECODE: If >= 1.00 then 1.00 | . . | |
| | | Mr. Fielder | Thank you for your time. Take care. | | | | |
| | | Angela | You've reached the halfway point. Only a little ways to go. Ms. Spanos needs to talk with you next about any legal issues you might have. Her door's across the street. Give it a click and we'll see you in a few minutes. | | | | |
| Legal Section | | | | | | | |
| | | Ms. Spanos | Hi. I'll need to ask you a few questions about any problems you might have had with the law. Let's get started. | | | | |

FIG. 6JJJJJJ

| Question ID | Onscreen Text | Actor | Audio Recordings | ASI-MV Codes | Skip Logic | Consistency | Extreme Values |
|---|---|---|---|---|---|---|---|
| Skip Alert Dialogue box | Are you sure you want to move on without answering this question? Yes No | Ms. Spanos | Are you sure you want to move on without answering this question? Yes, or No | If Yes, record -2 for skipped question | If Yes, go to next question. If No, return to question. ALL ASI-MV QUESTIONS GET THIS ALERT IF CLIENT SKIPS – UNLESS IT SPECIFIES AN EXTREME ALERT Add all -2 questions to Skipped Questions Report and Sum total in SKIPTotal variable | | |
| No-Skip Alert Dialogue box | This question is important, so please try to answer. Yes No | Ms. Spanos | This question is important, so would you please try to choose an answer? Yes No | If No, record -2 for skipped question | If No, go to next question. If Yes, return to ... | | |
| Extreme Alert Dialogue box | Is this the answer you want to give ___? Yes No | Ms. Spanos | Is this the answer you want to give? Yes No | If Yes, record answer to question | If No, return to question | | If Yes, add ... |
| Enter Prompt | none | Ms. Spanos | Remember, when you finish selecting your answer, click on the NEXT button to go to the next question. | none | | | |

FIG. 6KKKKKK

| Question ID | Onscreen Text | Actor | Audio Recordings | ASI-MV Codes | Skip Logic | Consistency | Extreme Values |
|---|---|---|---|---|---|---|---|
| (ASIL001) | Are you here because the legal or criminal justice system suggested it?<br><br>[Side bar]<br>For example, were you pressured/prompted by a judge, probation or parole officer?<br><br>Yes<br>No | Ms. Spanos | Are you here because the legal or criminal justice system suggested it?<br><br>For example, were you pressured or prompted by a judge, probation or parole officer?<br><br>Click Yes or No. | 1 = Yes<br>0 = No | | | |
| (ASIL002) | Are you currently on probation or parole?<br><br>Yes<br>No | Ms. Spanos | Are you currently on probation or parole?<br><br>Click Yes or No. | 1 = Yes<br>0 = No | | | |

FIG. 6LLLLLL

| Question ID | Onscreen Text | Actor | Audio Recordings | ASI-MV Codes | Skip Logic | Consistency | Extreme Values |
|---|---|---|---|---|---|---|---|
| ASIL003a = shoplifting ASIL004a = parole/probation ASIL005a = drug charges ASIL006a = forgery ASIL015a = contempt ASIL007a = weapons ASIL008a = burglary ASIL009a = robbery ASIL010a = assault ASIL011a = arson ASIL012a = rape ASIL013a = homicide ASIL016a = other ASIL016b = alimony? ASIL014a = prostitution ASILEVER = None | Have you ever been arrested and charged with any of the following? Please select all that apply. Include only charges since age 18. -Shoplifting or Vandalism -Parole or Probation violations -Drug charges or Possession -Forgery -Failure to pay alimony or child support -Weapons Offense -Burglary, Larceny, Breaking or entering -Robbery -Assault -Arson -Rape -Homicide or Manslaughter -Prostitution -Contempt of Court -Other (Do Not include misdemeanors) -None | Ms. Spanos | Have you ever been arrested and charged with any of the following? Please select all that apply. Include only charges since age 18. • Shoplifting or Vandalism • Parole or Probation violations • Drug charges or Possession • Forgery • Failure to pay alimony or child support • Weapons Offense • Burglary, Larceny, Breaking or entering • Robbery • Assault • Arson • Rape • Homicide or Manslaughter • Prostitution • Contempt of Court • Other (Do Not include misdemeanors) • None | 1 = Yes /selected 0 = No/not selected ASIL003a = shoplifting ASIL004a = parole/probation ASIL005a = drug charges ASIL006a = forgery ASIL015a = contempt ASIL007a = weapons ASIL008a = burglary ASIL009a = robbery ASIL010a = assault ASIL011a = arson ASIL012a = rape ASIL013a = homicide ASIL016a = other ASIL016b = alimony? ASIL014a = prostitution ASILEVER = None | IF ASIL003a = 1, go to ASIL003 IF ASIL004a = 1, go to ASIL004 IF ASIL005a = 1, go to ASIL005 IF ASIL006a = 1, go to ASIL006 IF ASIL015a = 1, go to ASIL015 IF ASIL007a = 1, go to ASIL007 IF ASIL008a = 1, go to ASIL008 IF ASIL009a = 1, go to ASIL009 IF ASIL010a = 1, go to ASIL010 IF ASIL011a = 1, go to ... | | |

FIG. 6MMMMM

| Question ID | Onscreen Text | Actor | Audio Recordings | ASI-MV Codes | Skip Logic | Consistency | Extreme Values |
|---|---|---|---|---|---|---|---|
| F/up | | | | | | | |
| ASIL_EVER | Since the last time you took this ASI interview, have you been arrested and charged with any of the following? Please select all that apply. include only charges since age 18. | | Since the last time you took this ASI interview, have you been arrested and charged with any of the following? Please select all that apply. Include only charges since age 18. | 1 = Yes /selected 0 = No/not selected | If ASIL003a = 1, go to ASIL003 IF ASIL004a = | | |
| ASIL003a = shoplifting | -Shoplifting or Vandalism | | -Shoplifting or Vandalism | ASIL003a = shoplifting | 1, go to ASIL004 IF ASIL005a = | | |
| ASIL004a = parole/probation | -Parole or Probation violations | | -Parole or Probation violations | ASIL004a = parole/probation | 1, go to ASIL005 | | |
| ASIL005a = drug charges | -Drug charges or Possession | | -Drug charges or Possession | ASIL005a = drug charges | IF ASIL006a = | | |
| ASIL006a = forgery | -Forgery | | -Forgery | ASIL006a = forgery | 1, go toASIL006 | | |
| ASIL015a = contempt | -Failure to pay alimony or child support | | -Failure to pay alimony or child support | ASIL015a = contempt | IF ASIL015a = 1, go to ASIL015 | | |
| ASIL007a = weapons | -Weapons Offense | | -Weapons Offense | ASIL007a = weapons | IF ASIL007a = 1, go to ASIL007 | | |
| ASIL008a = burglary | -Burglary, Larceny, Breaking or entering | | -Burglary, Larceny, Breaking or entering | ASIL008a = burglary | IF ASIL008a = 1, go to ASIL008 | | |
| ASIL009a = robbery | -Robbery | | -Robbery | ASIL009a = robbery | IF ASIL009a = 1, go to ASIL009 | | |
| ASIL010a = assault | -Assault | | -Assault | ASIL010a = assault | IF ASIL010a = 1, go to ASIL010 | | |
| ASIL011a = arson | -Arson | | -Arson | ASIL011a = arson | IF ASIL011a = 1, go to | | |
| ASIL012a = rape | -Rape | | -Rape | ASIL012a = rape | | | |
| ASIL013a = homicide | -Homicide or Manslaughter | | -Homicide or Manslaughter | ASIL013a = homicide | | | |
| ASIL016a = other | -Prostitution | | -Prostitution | ASIL016a = other | | | |
| ASIL016b = alimony? | -Contempt of Court | | -Contempt of Court | ASIL016b = alimony? | | | |
| ASIL014a = prostitution | -Other (Do Not include misdemeanors) | | -Other (Do Not include misdemeanors) | ASIL014a = prostitution | | | |
| ASILEVER = None | -None | | -None | ASILEVER = None | | | |

FIG. 6NNNNNN

| Question ID | Onscreen Text | Actor | Audio Recordings | ASI-MV Codes | Skip Logic | Consistency | Extreme Values |
|---|---|---|---|---|---|---|---|
| (ASIL003) | Estimate how many times you have been arrested and charged with shoplifting or vandalism. Times | Ms. Spanos | Estimate how many times you have been arrested and charged with shoplifting or vandalism. Remember, clicking and holding down the arrows will speed the counter up and down. | Coded as 2 digit variable | | | |
| (ASIL003) F/up | Since the last time you took this ASI interview, estimate how many times you have been arrested and charged with shoplifting or vandalism. Times | | Since the last time you took this ASI interview, estimate how many times you have been arrested and charged with shoplifting or vandalism. | Coded as 2 digit variable | | | |
| (ASIL004) | Estimate how many times you have been arrested and charged with parole or probation violations. Times | Ms. Spanos | Estimate how many times you have been arrested and charged with parole or probation violations. | Coded as 2 digit variable | | | |
| (ASIL004) F/up | Since the last time you took this ASI interview, estimate how many times you have been arrested and charged with parole or probation violations. Times | | Since the last time you took this ASI interview, estimate how many times you have been arrested and charged with parole or probation violations. | Coded as 2 digit variable | | | |
| (ASIL005) | Estimate how many times you have been arrested and charged with drug charges or possession. Times | Ms. Spanos | Estimate how many times you have been arrested and charged with drug charges or possession. | Coded as 2 digit variable | | | |

FIG. 6000000

| Question ID | Onscreen Text | Actor | Audio Recordings | ASI-MV Codes | Skip Logic | Consistency | Extreme Values |
|---|---|---|---|---|---|---|---|
| (ASIL005) F/up | Since the last time you took this ASI interview, estimate how many times you have been arrested and charged with drug charges or possession. Times | | Since the last time you took this ASI interview, estimate how many times you have been arrested and charged with drug charges or possession. | Coded as 2 digit variable | | | |
| (ASIL006) | Estimate how many times you have been arrested and charged with forgery. Times | Ms. Spanos | Estimate how many times you have been arrested and charged with forgery. | Coded as 2 digit variable | | | |
| (ASIL006) F/up | Since the last time you took this ASI interview, estimate how many times you have been arrested and charged with forgery. Times | | Since the last time you took this ASI interview, estimate how many times you have been arrested and charged with forgery. | Coded as 2 digit variable | | | |
| (ASIL016X) | Estimate how many times you have been arrested and charged with failure to pay alimony or child support. Times | Ms. Spanos | Estimate how many times you have been arrested and charged with failure to pay alimony or child support. | Coded as 2 digit variable Add to ASIL016 +ASIL016X = ASIL016 | | | |
| (ASIL016X) F/up | Since the last time you took this ASI interview, estimate how many times you have been arrested and charged with failure to pay alimony or child support. Times | | Since the last time you took this ASI interview, estimate how many times you have been arrested and charged with failure to pay alimony or child support. | Coded as 2 digit variable Add to ASIL016 +ASIL016X = ASIL016 | | | |

FIG. 6PPPPPP

| Question ID | Onscreen Text | Actor | Audio Recordings | ASI-MV Codes | Skip Logic | Consistency | Extreme Values |
|---|---|---|---|---|---|---|---|
| (ASIL007) | Estimate how many times you have been arrested and charged with a weapons offense. Times | Ms. Spanos | Estimate how many times you have been arrested and charged with a weapons offense. | Coded as 2 digit variable | | | |
| (ASIL007) F/up | Since the last time you took this ASI interview, estimate how many times you have been arrested and charged with a weapons offense. Times | | Since the last time you took this ASI interview, estimate how many times you have been arrested and charged with a weapons offense. | Coded as 2 digit variable | | | |
| (ASIL008) | Estimate how many times you have been arrested and charged with burglary, larceny, or breaking and entering. Times | Ms. Spanos | Estimate how many times you have been arrested and charged with burglary, larceny, or breaking and entering. | Coded as 2 digit variable | | | |
| (ASIL008) F/up | Since the last time you took this ASI interview, estimate how many times you have been arrested and charged with burglary, larceny, or breaking and entering. Times | | Since the last time you took this ASI interview, estimate how many times you have been arrested and charged with burglary, larceny, or breaking and entering. | Coded as 2 digit variable | | | |
| (ASIL009) | Estimate how many times you have been arrested and charged with robbery. Times | Ms. Spanos | Estimate how many times you have been arrested and charged with robbery. | Coded as 2 digit variable | | | |

FIG. 6QQQQQ

| Question ID | Onscreen Text | Actor | Audio Recordings | ASI-MV Codes | Skip Logic | Consistency | Extreme Values |
|---|---|---|---|---|---|---|---|
| (ASIL009) F/up | Since the last time you took this ASI interview, estimate how many times you have been arrested and charged with robbery. Times | | Since the last time you took this ASI interview, estimate how many times you have been arrested and charged with robbery. | Coded as 2 digit variable | | | |
| (ASIL010) | Estimate how many times you have been arrested and charged with assault. Times | Ms. Spanos | Estimate how many times you have been arrested and charged with assault. | Coded as 2 digit variable | | | |
| (ASIL010) F/up | Since the last time you took this ASI interview, estimate how many times you have been arrested and charged with assault. Times | | Since the last time you took this ASI interview, estimate how many times you have been arrested and charged with assault. | Coded as 2 digit variable | | | |
| (ASIL011) | Estimate how many times you have been arrested and charged with arson. Times | Ms. Spanos | Estimate how many times you have been arrested and charged with arson. | Coded as 2 digit variable | | | |
| (ASIL011) F/up | Since the last time you took this ASI interview, estimate how many times you have been arrested and charged with arson. Times | | Since the last time you took this ASI interview, estimate how many times you have been arrested and charged with arson. | Coded as 2 digit variable | | | |
| (ASIL012) | Estimate how many times you have been arrested and charged with rape. Times | Ms. Spanos | Estimate how many times you have been arrested and charged with rape. | Coded as 2 digit variable | | | |

FIG. 6RRRRRR

| Question ID | Onscreen Text | Actor | Audio Recordings | ASI-MV Codes | Skip Logic | Consistency | Extreme Values |
|---|---|---|---|---|---|---|---|
| (ASIL012) F/up | Since the last time you took this ASI interview, estimate how many times you have been arrested and charged with rape. Times | | Since the last time you took this ASI interview, estimate how many times you have been arrested and charged with rape. | Coded as 2 digit variable | | | |
| (ASIL013) | Estimate how many times you have been arrested and charged with homicide or manslaughter. Times | Ms. Spanos | Estimate how many times you have been arrested and charged with homicide or manslaughter. | Coded as 2 digit variable | | | |
| (ASIL013) F/up | Since the last time you took this ASI interview, estimate how many times you have been arrested and charged with homicide or manslaughter. Times | | Since the last time you took this ASI interview, estimate how many times you have been arrested and charged with homicide or manslaughter. | Coded as 2 digit variable | | | |
| (ASIL014) | Estimate how many times you have been arrested and charged with prostitution. Times | Ms. Spanos | Estimate how many times you have been arrested and charged with prostitution. | Coded as 2 digit variable | | | |
| (ASIL014) F/up | Since the last time you took this ASI interview, estimate how many times you have been arrested and charged with prostitution. Times | | Since the last time you took this ASI interview, estimate how many times you have been arrested and charged with prostitution. | Coded as 2 digit variable | | | |

FIG. 6SSSSSS

| Question ID | Onscreen Text | Actor | Audio Recordings | ASI-MV Codes | Skip Logic | Consistency | Extreme Values |
|---|---|---|---|---|---|---|---|
| (ASIL015) | Estimate how many times you have been arrested and charged with contempt of court.<br>[Side bar]<br>Do not include failure to pay alimony or child support charges.<br>Times | Ms. Spanos | Estimate how many times you have been arrested and charged with contempt of court.<br>Do not include failure to pay alimony or child support charges. | Coded as 2 digit variable | | | |
| (ASIL015)<br>F/up | Since the last time you took this ASI interview, estimate how many times you have been arrested and charged with contempt of court.<br>[Side bar]<br>Do not include failure to pay alimony or child support charges.<br>Times | | Since the last time you took this ASI interview, estimate how many times you have been arrested and charged with contempt of court. Do not include failure to pay alimony or child support charges. | Coded as 2 digit variable | | | |
| (ASIL016) | Estimate how many times you have been arrested and charged with other offenses.<br>[Side bar]<br>For example, illegal gambling, reckless endangering, or terrorist threats? Do not count misdemeanors.<br>Times | Ms. Spanos | Estimate how many times you have been arrested and charged with other offenses.<br>For example, illegal gambling, reckless endangering, or terrorist threats?<br>Do not count misdemeanors. | Add to ASIL016 + ASIL016X = ASIL016<br>Coded as 2 digit variable | | | |

FIG. 6TTTTT

| Question ID | Onscreen Text | Actor | Audio Recordings | ASI-MV Codes | Skip Logic | Consistency | Extreme Values |
|---|---|---|---|---|---|---|---|
| (ASIL016) F/up | Since the last time you took this ASI interview, estimate how many times you have been arrested and charged with other offenses.<br><br>[Side bar]<br>For example, illegal gambling, reckless endangering, or terrorist threats? Do not count misdemeanors.<br><br>Times | | Since the last time you took this ASI interview, estimate how many times you have been arrested and charged with other offenses. For example, illegal gambling, reckless endangering, or terrorist threats? Do not count misdemeanors. | Add to ASIL016 + ASIL016X = ASIL016<br><br>Coded as 2 digit variable | | | |
| (ASIL017) | Estimate how many of these charges resulted in convictions.<br><br>[Side bar]<br>Convictions include fines, probation, suspended and required sentences and guilty pleas. Charges for parole and probation violation are counted as convictions. Include all convictions since age 18.<br><br>Convictions None | Ms. Spanos | Estimate how many of these charges resulted in convictions.<br><br>Convictions include fines, probation, suspended and required sentences and guilty pleas.<br><br>Charges for parole and probation violation are counted as convictions.<br><br>Include all convictions since age 18.<br><br>If None, click here. | Coded as 2 digit variable<br><br>None = 0 | | NOTE: should not > # total charges. So ASIL017 ≤ sum (ASIL003 to ASIL016) | |

FIG. 6UUUUUU

| Question ID | Onscreen Text | Actor | Audio Recordings | ASI-MV Codes | Skip Logic | Consistency | Extreme Values |
|---|---|---|---|---|---|---|---|
| (ASIL017) F/up | Since the last time you took this ASI interview, estimate how many of these charges resulted in convictions. [Side bar] Convictions include fines, probation, suspended and required sentences and guilty pleas. Charges for parole and probation violation are counted as convictions<br><br>Times None | | Since the last time you took this ASI interview, estimate how many of these charges resulted in convictions. Convictions include fines, probation, suspended and required sentences and guilty pleas. Charges for parole and probation violation are counted as convictions<br><br>If None, click here. | Coded as 2 digit variable<br><br>None = 0 | | NOTE: should not > # total charges, So (ASIL017 ≤ sum (ASIL003 to ASIL016) | |
| (ASIL018) | Estimate how many times you have been arrested and charged with disorderly conduct, vagrancy, or public drunkenness. [Side bar] Count only those arrests for which you were charged with a misdemeanor.<br><br>Times Never | Ms. Spanos | Estimate how many times you have been arrested and charged with disorderly conduct, vagrancy, or public drunkenness. Count only those arrests for which you were charged with a misdemeanor.<br><br>If Never, click this button. | Coded as 2 digit variable<br><br>Never = 0 | | | |

FIG. 6VVVVVV

| Question ID | Onscreen Text | Actor | Audio Recordings | ASI-MV Codes | Skip Logic | Consistency | Extreme Values |
|---|---|---|---|---|---|---|---|
| (ASIL018) F/up | Since the last time you took this ASI interview, estimate how many times you have been arrested and charged with disorderly conduct, vagrancy, or public drunkenness. [Side bar] Count only those arrests for which you were charged with a misdemeanor. Times Never | | Since the last time you took this ASI interview, estimate how many times you have been arrested and charged with disorderly conduct, vagrancy, or public drunkenness. Count only those arrests for which you were charged with a misdemeanor. If Never, click this button. | Coded as 2 digit variable Never = 0 | | | |
| (ASIL019) | Estimate how many times in your life you have been arrested and charged with driving while intoxicated (DWI) or driving under the influence (DUI). Times Never | Ms. Sparros | Estimate how many times in your life you have been arrested and charged with driving while intoxicated (DWI) or driving under the influence (DUI). If Never, click this button. | Coded as 2 digit variable Never = 0 | | | |
| (ASIL019) F/up | Since the last time you took this ASI interview, estimate how many times you have been arrested and charged with driving while intoxicated (DWI). Times Never | | Since the last time you took this ASI interview, estimate how many times you have been arrested and charged with driving while intoxicated (DWI). If Never, click this button. | Coded as 2 digit variable Never = 0 | | | |

FIG. 6WWWWW

| Question ID | Onscreen Text | Actor | Audio Recordings | ASI-MV Codes | Skip Logic | Consistency | Extreme Values |
|---|---|---|---|---|---|---|---|
| (ASIL020) | Estimate how many times in your life you have been charged with other driving violations.<br><br>[Side bar] This includes reckless driving, speeding, driving without a license, etc. Do not include parking tickets or non-moving violations.<br><br>Times<br>Never | Ms. Spanos | Estimate how many times in your life you have been charged with other driving violations.<br><br>This includes reckless driving, speeding, driving without a license, etc.<br><br>Do not include parking tickets or non-moving violations.<br><br>If Never, click the button. | Coded as 2 digit variable<br><br>Never = 0 | | | |
| (ASIL020)<br>F/up | Since the last time you took this ASI interview, estimate how many times you have been charged with other driving violations.<br><br>[Side bar] This includes reckless driving, speeding, driving without a license, etc. Do not include parking tickets or non-moving violations.<br><br>Times<br>Never | | Since the last time you took this ASI interview, estimate how many times you have been charged with other driving violations. This includes reckless driving, speeding, driving without a license, etc. Do not include parking tickets or non-moving violations.<br><br>If Never, click the button. | Coded as 2 digit variable<br><br>Never = 0 | | | |

FIG. 6XXXXXX

| Question ID | Onscreen Text | Actor | Audio Recordings | ASI-MV Codes | Skip Logic | Consistency | Extreme Values |
|---|---|---|---|---|---|---|---|
| (ASIL021) | In your life, how much total time have you spent in jail or prison since age 18?<br><br>Years<br>Months<br>Between 2 weeks and 1 month<br>Less than 2 weeks<br>Never been in jail or prison | Ms. Spanos | In your life, how much total time have you spent in jail or prison since age 18?<br><br>• Between 2 weeks and 1 month<br>• Less than 2 weeks<br>• Never been in jail or prison<br><br>If more than one month, please use the counter to indicate how long. | Year/month counter So (year X12) + months = total months<br>- Coded as 3 digit (MAX value = AGE) | If ASIL021 = 0, go to ASIL025 (skip ASIL022 & ASIL023) | If ASIG019 =2 & ASIL021 = 0, Consistency Alert<br><br>If no: FLAG (if they don't change it. | |
| (ASIL021) F/up | Since the last time you took this ASI interview, how much total time have you spent in jail or prison since age 18?<br><br>Between 2 weeks and 1 month<br>Less than 2 weeks<br>Never been in jail or prison | | Since the last time you took this ASI interview, how much total time have you spent in jail or prison since age 18?<br><br>Between 2 weeks and 1 month<br>Less than 2 weeks<br>Never been in jail or prison<br><br>If more than one month, please use the counter to indicate how long. | Year/month counter variable coded in months So (year x12) + months = | If OCL021 = 0, go to ASIL025 (skip ASIL022 & ASIL023) | | |
| (ASIL022) | How long were you in jail or prison the last time you were there?<br><br>Years<br>Months<br>Between 2 weeks and 1 month<br>Less than 2 weeks<br>Never been in jail or prison | Ms. Spanos | How long were you in jail or prison the last time you were there?<br><br>• Between 2 weeks and 1 month<br>• Less than 2 weeks<br>• Never been in jail or prison<br><br>If more than one month, please use the counter to indicate how long. | Year/month counter variable coded in months So (year x12) + months = total months | Skipped if ASIL021=0 (coded as -1) | | |

FIG. 6YYYYYY

| Question ID | Onscreen Text | Actor | Audio Recordings | ASI-MV Codes | Skip Logic | Consistency | Extreme Values |
|---|---|---|---|---|---|---|---|
| (ASIF008) | Do you live with anyone who uses non-prescribed drugs or abuses prescription drugs?<br><br>Yes<br>No | Ms. Carter | Do you live with anyone who uses non-prescribed drugs or abuses prescription drugs?<br><br>Click Yes or No. | Yes = 1<br>No = 0 | | | |
| (ASIF009) | Who do you spend most of your free time with?<br><br>-with family<br>-with live-in significant other<br>-with boyfriend or girlfriend<br>-with friends<br>-alone | Ms. Carter | Who do you spend most of your free time with?<br><br>• with family<br>• with live-in significant other<br>• with boyfriend or girlfriend<br>• with friends<br>• alone | 1 = with family<br>2 = with live-in significant other<br>3 = with boyfriend or girlfriend<br>4 = with friends, or<br>0 = alone | | | |
| (ASIF0010) | Are you satisfied spending your free time this way?<br><br>Yes<br>No<br>Neither satisfied nor dissatisfied | Ms. Carter | Are you satisfied spending your free time this way?<br><br>• Yes<br>• Neither satisfied nor dissatisfied<br>• No | Yes = 2<br>No = 0<br>Neither satisfied nor dissatisfied = 1 | | | |
| (ASIF011) | Estimate how many people you would count as close friends.<br>[Side bar]<br>Do not include acquaintances<br>•<br>•<br>• | Ms. Carter | Estimate how many people you would count as close friends.<br>A close friend would be someone who you trust and feel you can talk to.<br>Do not include acquaintances or people you see only from time to time.<br><br>If None, click this button. | - Coded as a 2 digit variable<br>- None = 0 | | | If ASIF011 > 9, Extreme Alert and if not changed, add question and answer to the Extreme Values Report |

FIG. 6ZZZZZZ

| Question ID | Onscreen Text | Actor | Audio Recordings | ASI-MV Codes | Skip Logic | Consistency | Extreme Values |
|---|---|---|---|---|---|---|---|
| (ASIL023) | The last time you were in jail or prison, what were you in for? Please select all that apply.<br><br>Shoplifting or Vandalism<br>Parole or Probation Violations<br>Drug Charges or Possession<br>Forgery<br>Failure to Pay Alimony<br>Weapons Offense<br>Burglary, Larceny, or Breaking and Entering<br>Robbery<br>Assault<br>Arson<br>Rape<br>Homicide or Manslaughter<br>Prostitution<br>Contempt of Court<br>Disorderly Conduct or Vagrancy or Public Intoxication<br>Driving While Intoxicated<br>Major Driving Violations<br>Other (Do not include misdemeanors) | Ms. Spanos | The last time you were in jail or prison, what were you in for?<br><br>Please select all that apply.<br><br>• Shoplifting or Vandalism<br>• Parole or Probation Violations<br>• Drug Charges or Possession<br>• Forgery<br>• Failure to Pay Alimony<br>• Weapons Offense<br>• Burglary, Larceny, or Breaking and Entering<br>• Robbery<br>• Assault<br>• Arson<br>• Rape<br>• Homicide or Manslaughter<br>• Prostitution<br>• Contempt of Court<br>• Disorderly Conduct or Vagrancy or Public Intoxication<br>• Driving While Intoxicated<br>• Major Driving Violations<br>• Other (Do not include misdemeanors) | - Shoplifting/vandalis m = 6<br>- Parole/probation violations = 7<br>- Drug charges/possessio n = 8<br>- Forgery = 9<br>- Failure to pay alimony = 4<br>- Weapons offence = 10<br>- B/L/B&E = 11<br>- Robbery = 12<br>- Assault = 13<br>- Arson = 14<br>- Rape = 15<br>- Homicide/ manslaughter = 16<br>- Prostitution = 5<br>- Contempt of court = 4<br>- Disorderly conduct, vagrancy, public intoxication = 1<br>. . . | Skipped if ASIL021=0 (coded as -1) | | |

FIG. 6AAAAAAA

| Question ID | Onscreen Text | Actor | Audio Recordings | ASI-MV Codes | Skip Logic | Consistency | Extreme Values |
|---|---|---|---|---|---|---|---|
| (ASIL024) | NO SCREEN<br><br>Are you presently awaiting charges, trial, or sentence? | | [NO AUDIO] | ** Calculate from ASIL025 (new variable) -<br><br>If ASIL025 (new variable) >= 1<br>then ASIL024 = 1 (yes)<br>Else<br>   ASIL024 = 0 (no) | | | |

FIG. 6BBBBBB

| Question ID | Onscreen Text | Actor | Audio Recordings | ASI-MV Codes | Skip Logic | Consistency | Extreme Values |
|---|---|---|---|---|---|---|---|
| (ASIL025)<br><br>(Composite Question) | Are you awaiting charges, trial or sentencing for any of the following? Please select all that apply.<br><br>Shoplifting or Vandalism<br>Parole or Probation Violations<br>Drug Charges or Possession<br>Forgery<br>Failure to Pay Alimony<br>Weapons Offense<br>Burglary, Larceny, or Breaking and Entering<br>Robbery<br>Assault<br>Arson<br>Rape<br>Homicide or Manslaughter<br>Prostitution<br>Contempt of Court<br>Disorderly Conduct or Vagrancy or Public Intoxication<br>Driving While Intoxicated<br>Major Driving Violations<br>Other (Do not include misdemeanors)<br>NONE | Ms. Spanos | Are you awaiting charges, trial or sentencing for any of the following?<br><br>Please select all that apply.<br><br>• Shoplifting or Vandalism<br>• Parole or Probation Violations<br>• Drug Charges or Possession<br>• Forgery<br>• Failure to Pay Alimony<br>• Weapons Offense<br>• Burglary, Larceny, or Breaking and Entering<br>• Robbery<br>• Assault<br>• Arson<br>• Rape<br>• Homicide or Manslaughter<br>• Prostitution<br>• Contempt of Court<br>• Disorderly Conduct or Vagrancy or Public Intoxication<br>• Driving While Intoxicated<br>• Major Driving Violations<br>• Other (Do not include misdemeanors)<br>• None | - Shoplifting/vandalis m = 6<br>- Parole/probation violations = 7<br>- Drug charges/possessio n = 8<br>- Forgery = 9<br>- Failure to pay alimony= 4<br>- Weapons offence = 10<br>- B/L/B&E = 11<br>- Robbery = 12<br>- Assault = 13<br>- Arson = 14<br>- Rape = 15<br>- Homicide/ manslaughter = 16<br>- Prostitution = 5<br>- Contempt of court = 4.5<br>- Disorderly conduct, vagrancy, public intoxication = 1<br>. . . | If -2 (refused), show No-Skip Alert | | |

FIG. 6CCCCCC

| Question ID | Onscreen Text | Actor | Audio Recordings | ASI-MV Codes | Skip Logic | Consistency | Extreme Values |
|---|---|---|---|---|---|---|---|
| (ASIL026) (Composite Question) | In the past 30 days, estimate how many days were you in prison or jail. [Side bar] This includes being detained or being arrested, but released on the same day. Days None | Ms. Spanos | In the past 30 days, estimate how many days you were in prison or jail. This includes being detained or being arrested, but released on the same day. If None, click this button. | - Coded as 2 digit variable (MAX = 30) - None = 0 | | | |
| (ASIL027) (Composite Question) | In the past 30 days, estimate how many days you did anything illegal for profit, such as shoplifting, stealing, selling drugs, or prostitution. Days None | Ms. Spanos | In the past 30 days, estimate how many days you did anything illegal for profit, such as shoplifting, stealing, selling drugs, or prostitution. If None, click this button. | - Coded as 2 digit variable (MAX = 30) - None = 0 | If -2 (refused), show No-Skip Alert | | |
| L41Z | How serious do you feel your present legal problems involving your family are? [Side bar] For example, family or juvenile court issues, child custody involving DHS, divorce, domestic violence, etc. Not at all Slightly Moderately Considerably Extremely | | How serious do you feel your present legal problems involving your family are? For example, family or juvenile court issues, child custody involving DHS, divorce, domestic violence, etc. Not at all Slightly Moderately Considerably Extremely | Not at all = 0 Slightly = 1 Moderately = 2 Considerably = 3 Extremely = 4 | | | |

FIG. 6DDDDDDD

| Question ID | Onscreen Text | Actor | Audio Recordings | ASI-MV Codes | Skip Logic | Consistency | Extreme Values |
|---|---|---|---|---|---|---|---|
| L4ZZ | How important to you now is counseling or referral for legal problems involving your family?<br><br>[Side bar]<br>For example, family or juvenile court issues, child custody involving DHS, divorce, domestic violence, etc.<br><br>Not at all<br>Slightly<br>Moderately<br>Considerably<br>Extremely | | How important to you now is counseling or referral for legal problems involving your family? For example, family or juvenile court issues, child custody involving DHS, divorce, domestic violence, etc.<br><br>Not at all<br>Slightly<br>Moderately<br>Considerably<br>Extremely | Not at all = 0<br>Slightly = 1<br>Moderately = 2<br>Considerably = 3<br>Extremely = 4 | | | |
| (ASIL028)<br>(Composite Question) | How serious do you feel your present legal problems are?<br><br>[Side bar]<br>Do not include civil problems like custody fights, divorce, etc.<br><br>Not at all<br>Slightly<br>Moderately<br>Considerably<br>Extremely | Ms. Spanos | How serious do you feel your present legal problems are?<br><br>Do not include civil problems like custody fights or divorce.<br><br>• Not at all<br>• Slightly<br>• Moderately<br>• Considerably<br>• Extremely | 0 = Not at all<br>1 = Slightly<br>2 = Moderately<br>3 = Considerably<br>4 = Extremely | If -2 (refused), show No-Skip Alert | | |

FIG. 6EEEEEE

| Question ID | Onscreen Text | Actor | Audio Recordings | ASI-MV Codes | Skip Logic | Consistency | Extreme Values |
|---|---|---|---|---|---|---|---|
| (ASIL029)<br>(Composite Question) | How important to you now is counseling or referral for legal problems?<br><br>[Side bar]<br>Do not include civil problems like custody fights, divorce, etc.<br><br>Not at all<br>Slightly<br>Moderately<br>Considerably<br>Extremely | Ms. Spanos | How important to you now is counseling or referral for legal problems?<br><br>Do not include civil problems like custody fights or divorce.<br><br>• Not at all<br>• Slightly<br>• Moderately<br>• Considerably<br>• Extremely | 0 = Not at all<br>1 = Slightly<br>2 = Moderately<br>3 = Considerably<br>4 = Extremely | If -2 (refused), show No-Skip Alert | | |
| ASIL030 | | | | (Calculated Variable)<br>Legal Severity Rating | COMPUTE legalsev = SUM(ASIL026, ASIL027).<br>COMPUTE legaldur = SUM(ASIL003, ASIL004, ASIL005, ASIL006, ASIL007, ASIL008, ASIL009, ASIL010, ASIL011, ASIL012, ASIL013, ASIL014, ASIL015, ASIL018, ASIL019, ASIL020, ASIL021).<br>COMPUTE ASIL030 = (ASIL029 * .824) + (ASIL028 * .720) + (legaldur * .005558) + (legalsev * .01079) + .489 .<br>Round ASIL030 to nearest whole number.<br>If >= 9 then 9<br>Otherwise regular rounding. | | |

FIG. 6FFFFFF

| Question ID | Onscreen Text | Actor | Audio Recordings | ASI-MV Codes | Skip Logic | Consistency | Extreme Values |
|---|---|---|---|---|---|---|---|
| COMPLEG (Calculated Variable) | | | | Legal Composite Score (.000-1.000) | (-2) = missing (or blank) Formulas: IF (asil023 = 0) Then asil024 = 0 If (asil023 >= 1) Then asil024 = 1 IF ( asie017 > 0) Then LOGLEG = LN( asie017 )/46. IF ( asie017 = 0) Then LOGLEG = 0. LEGAL = (asil024 / 5) + (asil027 / 150) + (asil028 / 20) + (asil029 / 20) . COMPLEG = LEGAL + LOGLEG RECODE: if >= 1.00 then 1.00 | | |
| | | Ms. Spanos | Thanks for answering my questions. Goodbye. | | | | |
| | | George | Almost finished! Now you need to meet with Ms. Carter about how things are going with your family and friends. This should not take too long. That's her door right over there. Just click on it, and she'll see you right away. | | | | |
| Family and Social Section | | | | | | | |
| | | Ms. Carter | Welcome. I'll be asking you some questions about how things are going with you and your family. | | | | |

FIG. 6GGGGGGG

| Question ID | Onscreen Text | Actor | Audio Recordings | ASI-MV Codes | Skip Logic | Consistency | Extreme Values |
|---|---|---|---|---|---|---|---|
| Skip Alert Dialogue box | Are you sure you want to move on without answering this question? Yes No | Ms. Carter | Are you sure you want to move on without answering this question? Yes, or No | If Yes, record -2 for skipped question | If Yes, go to next question. If No, return to question. ALL ASI-MV QUESTIONS GET THIS ALERT IF CLIENT SKIPS – UNLESS IT SPECIFIES AN EXTREME ALERT Add all -2 questions to Skipped Questions Report and Sum total in SKIPTotal variable | | |
| No-Skip Alert Dialogue box | This question is important, so please try to answer. Yes No | Ms. Carter | This question is important, so would you please try to choose an answer? Yes No | If No, record -2 for skipped question | If No, go to next question. If Yes, return to . . . | | |
| Extreme Alert Dialogue box | Is this the answer you want to give ___? Yes No | Ms. Carter | Is this the answer you want to give? Yes No | If Yes, record answer to question | If No, return to question | | If Yes, add . . . |
| Enter Prompt | none | Ms. Carter | Remember, when you finish selecting your answer, click on the NEXT button to go to the next question. | none | | | |

FIG. 6HHHHHHH

| Question ID | Onscreen Text | Actor | Audio Recordings | ASI-MV Codes | Skip Logic | Consistency | Extreme Values |
|---|---|---|---|---|---|---|---|
| (ASIF001) | What is your current marital status?<br><br>Single (never married)<br>Married or Living as married<br>Remarried<br>Widowed<br>Legally separated<br>Divorced | Ms. Carter | What is your current marital status?<br><br>• Single (never married)<br>• Married or Living as married<br>• Remarried<br>• Widowed<br>• Legally separated<br>• Divorced | - Single = 6<br>- Married or living as married = 1<br>- Remarried = 2<br>- Widowed = 3<br>- Legally separated = 4<br>- Divorced = 5 | | | |
| (ASIF002Y)<br>(ASIF002M) | How long have you been in your current marital status?<br><br>Between 2 weeks and 1 month<br>Under 2 weeks<br>If more than one month, please use the counter to indicate how long<br><br>Years<br>Months | Ms. Carter | How long have you been in your current marital status?<br><br>• Between 2 weeks and 1 month<br>• Under 2 weeks<br><br>If more than one month, please use the counter to indicate how long.<br><br>Remember, clicking and holding down the arrows will speed the counter up and down. | (MAX value = AGE)<br>-Between 2 weeks & 1 month = 1<br>-Under 2 weeks = 1 | | | |
| (ASIF003)<br>(Composite Question) | Are you satisfied with your current marital status?<br><br>Yes<br>Neither satisfied nor dissatisfied<br>No | Ms. Carter | Are you satisfied with your current marital status?<br><br>• Yes<br>• Neither satisfied nor dissatisfied<br>• No | Yes = 2<br>No = 0<br>Neither satisfied nor dissatisfied = 1 | If -2 (refused), show No-Skip Alert | | |

FIG. 6IIIIII

| Question ID | Onscreen Text | Actor | Audio Recordings | ASI-MV Codes | Skip Logic | Consistency | Extreme Values |
|---|---|---|---|---|---|---|---|
| (ASIF004) | What has been your usual living arrangement for most of the past 3 years?<br>-With significant other or spouse and children<br>-With significant other or spouse alone<br>-With children alone<br>-With parents<br>-With family<br>-With friends<br>-Alone<br>-Jail, hospital, inpatient rehab or halfway house<br>-No stable living arrangements (homeless, shelters, drifting) | Ms. Carter | What has been your usual living arrangement for most of the past 3 years?<br>• With Significant Other or Spouse and Children<br>• With Significant Other or Spouse Alone<br>• With Children Alone<br>• With Parents<br>• With Family<br>• With Friends<br>• Alone<br>• Jail, Hospital, Inpatient Rehab or Halfway House<br>• No Stable Living Arrangements (homeless, shelters, or drifting). | - w/ significant other/spouse & children = 1<br>- w/ significant other/spouse alone = 2<br>- w/ children alone = 3<br>- w/ parents = 4<br>- w/ family = 5<br>- w/ friends = 6<br>- alone = 7<br>- jail, hospital, inpatient rehab or halfway house = 8<br>- no stable living arrangements = 9 | | | |
| (ASIF004) F/up | Since the last time you took this ASI interview, what has been your usual living arrangement?<br>-With significant other or spouse and children<br>-With significant other/spouse alone<br>-With children alone<br>.<br>.<br>. | | Since the last time you took this ASI interview, what has been your usual living arrangement?<br>-With significant other or spouse and children<br>-With significant other/spouse alone<br>-With children alone<br>-With parents<br>-With family<br>.<br>.<br>. | - w/ significant other/spouse & children = 1<br>- w/ significant other/spouse alone = 2<br>- w/ children alone = 3<br>- w/ parents = 4<br>- w/ family = 5<br>.<br>.<br>. | | | |

FIG. 6JJJJJJJ

| Question ID | Onscreen Text | Actor | Audio Recordings | ASI-MV Codes | Skip Logic | Consistency | Extreme Values |
|---|---|---|---|---|---|---|---|
| (ASIF005y) (ASIF005m) | About how long have you lived in this arrangement? [Side bar] If you live with your parents or family, count only the time since age 18. Between 2 weeks and 1 month Under 2 weeks If more than one month, please use the counter to indicate how long. Years Months | Ms. Carter | About how long have you lived in this arrangement? If you live with your parents or family, count only the time since age 18. - Between 2 weeks and 1 month - Under 2 weeks If more than one month, please use the counter to indicate how long. | (MAX value = AGE) - Between 2 weeks & 1 month = 1 - Under 2 weeks = .1 | | | |
| (ASIF006) | Have you been satisfied with this living arrangement? Yes Neither satisfied nor dissatisfied No | Ms. Carter | Have you been satisfied with this living arrangement? • Yes • Neither satisfied nor dissatisfied • No | Yes = 2 No = 0 Neither satisfied nor dissatisfied = 1 | | | |

FIG. 6KKKKKK

| Question ID | Onscreen Text | Actor | Audio Recordings | ASI-MV Codes | Skip Logic | Consistency | Extreme Values |
|---|---|---|---|---|---|---|---|
| (ASIF006A) | Do you currently live: <br>-in a halfway house or other treatment facility <br>-supervised living facility <br>-in prison or jail <br>-in a hospital <br>-private home or apartment <br>-no stable living arrangement (homeless, shelters, drifting) | Ms. Carter | Do you currently live <br>• in a halfway house, <br>• supervised living facility, <br>• in a prison or jail, <br>• in a hospital, <br>• in a private home or apartment <br>• have no stable living arrangement, (homeless, shelters, or drifting)? | 1 = in a halfway house or in a halfway house <br>2 = supervised living facility | If ASIF006A = 0, go to ASIF006B, then ASIF006C <br><br>If ASIF006A = 1, go to ASIF007, then ASIF008 | | |
| (ASIF006B) | When you leave your current situation, will you be living with anyone who has an alcohol problem? <br>Yes <br>No <br>Not sure | Ms. Carter | When you leave your current situation, will you be living with anyone who has an alcohol problem? <br><br>Click Yes, No, or Unsure. | Yes = 1 <br>No = 0 <br>Not sure where I will be = -9 | After answering ASIF006B, go to ASIF006C <br><br>Answer for ASIF006B is coded as answer for ASIF007 | | |
| (ASIF006C) | When you leave your current situation, will you be living with anyone who uses non-prescribed drugs or abuses prescription drugs? <br>Yes <br>No <br>Not sure | Ms. Carter | When you leave your current situation, will you be living with anyone who uses non-prescribed drugs or abuses prescription drugs? <br><br>Click Yes, No, or Unsure. | Yes = 1 <br>No = 0 <br>Not sure where I will be = -9 | After answering ASIF006C, go to ASIF009 <br><br>Answer for ASIF006C is coded as answer for ASIF008 | | |
| (ASIF007) | Do you live with anyone who has an alcohol problem? <br>Yes <br>No | Ms. Carter | Do you live with anyone who has an alcohol problem? <br><br>Click Yes or No | Yes = 1 <br>No = 0 | | | |

FIG. 6LLLLLL

| Question ID | Onscreen Text | Actor | Audio Recordings | ASI-MV Codes | Skip Logic | Consistency | Extreme Values |
|---|---|---|---|---|---|---|---|
| (ASIF012) | Would you say that during your lifetime you have had a close, long-lasting, personal relationship with your mother?<br>Yes<br>No<br>Not sure | Ms. Carter | Would you say that during your lifetime you have had a close, long-lasting, personal relationship with your mother?<br>• Yes<br>• No<br>• Not sure<br>• Never knew my mother | Yes = 1<br>No = 0<br>Not sure = -9<br>No recent<br>Never knew my mother = -1 | If ASIF012 = -1, go to ASIF013 | | |
| (ASIF018P)<br>(Composite Question) | In the past 30 days, have you had arguments or serious problems getting along with your mother?<br>Yes<br>No<br>Not sure<br>No contact with my mother in past 30 days | Ms. Carter | In the past 30 days, have you had arguments or serious problems getting along with your mother?<br>• Yes<br>• No<br>• Not sure<br>• No contact with my mother in past 30 days | Yes = 1<br>No = 0<br>Not sure = -9<br>No recent contact w/ mother = -1 | If -2 (refused), show No-Skip Alert | | |
| (ASIF018L) | Have there been other periods in your life when you had serious problems getting along with your mother? | Ms. Carter | Have there been other periods in your life when you had serious problems getting along with your mother?<br>Click Yes, No, or Unsure. | Yes = 1<br>No = 0<br>Unsure = -9 | | | |
| (ASIF013) | Would you say that during your lifetime you have had a close, long-lasting, personal relationship with your father? | Ms. Carter | Would you say that during your lifetime you have had a close, long-lasting, personal relationship with your father?<br>•<br>•<br>• | Yes = 1<br>No = 0<br>Not sure = -9<br>Never knew my father = -1 | If ASIF013 = -1, go to ASIF014 | | |

FIG. 6MMMMMM

| Question ID | Onscreen Text | Actor | Audio Recordings | ASI-MV Codes | Skip Logic | Consistency | Extreme Values |
|---|---|---|---|---|---|---|---|
| (ASIF019P) (Composite Question) | In the past 30 days, have you had arguments or serious problems getting along with your father? Yes No Not sure No contact with my father in past 30 days | Ms. Carter | In the past 30 days, have you had arguments or serious problems getting along with your father? • Yes • No • Not sure • No contact with my father in past 30 days | Yes = 1 No = 0 Not sure = -9 No recent contact w/ father = -1 | If -2 (refused), show No-Skip Alert | | |
| (ASIF019L) | Have there been other periods in your life when you had serious problems getting along with your father? Yes No Not sure | Ms. Carter | Have there been other periods in your life when you had serious problems getting along with your father? • Yes • No • Not sure | Yes = 1 No = 0 Unsure = -9 | | | |
| (ASIF014) | Would you say that during your lifetime you have had a close, long-lasting, personal relationship with your brothers and sisters? No brothers or sisters Yes No Not sure Never knew my brothers or sisters | Ms. Carter | Would you say that during your lifetime you have had a close, long-lasting, personal relationship with any one of your brothers or sisters? • No brothers or sisters • Yes • No • Not sure • Never knew my brothers or sisters | No brothers/ sisters = 2 Yes = 1 No = 0 Not sure = -9 Never knew my siblings = -1 | If ASIF014 = -1, go to ASIF015 | | |

FIG. 6NNNNNN

| Question ID | Onscreen Text | Actor | Audio Recordings | ASI-MV Codes | Skip Logic | Consistency | Extreme Values |
|---|---|---|---|---|---|---|---|
| (ASIF020P)<br><br>(Composite Question) | In the past 30 days, have you had arguments or serious problems getting along with any one of your brother or sisters?<br>Yes<br>No<br>Not sure<br>No contact with my brothers or sisters in past 30 days | Ms. Carter | In the past 30 days, have you had arguments or serious problems getting along with any one of your brother or sisters?<br><br>• Yes<br>• No<br>• Not sure<br>• No contact with my brothers or sisters in past 30 days | Yes = 1<br>No = 0<br>Not sure = -9<br>No recent contact w/ my siblings = -1 | If -2 (refused), show No-Skip Alert | | |
| (ASIF020L) | Have there been other periods in your life when you had serious problems getting along with any one of your brothers or sisters?<br>Yes<br>No<br>Not sure | Ms. Carter | Have there been other periods in your life when you had serious problems getting along with any one of your brothers or sisters?<br><br>• Yes<br>• No<br>• Not sure | Yes = 1<br>No = 0<br>Unsure = -9 | | | |
| (ASIF015) | Would you say that during your lifetime you have had a close, long-lasting, personal relationship with your significant other or spouse?<br>No significant other or spouse<br>Yes<br>No<br>Not sure | Ms. Carter | Would you say that during your lifetime you have had a close, long-lasting, personal relationship with your significant other or spouse?<br><br>• No significant other or spouse<br>• Yes<br>• No<br>• Not sure | No significant other/spouse = -1<br>Yes = 1<br>No = 0<br>Not sure = -9 | If ASIF015 = -1, go to ASIF016 | | |

FIG. 6OOOOOO

| Question ID | Onscreen Text | Actor | Audio Recordings | ASI-MV Codes | Skip Logic | Consistency | Extreme Values |
|---|---|---|---|---|---|---|---|
| (ASIF021P) (Composite Question) | In the past 30 days, have you had arguments or serious problems getting along with your significant other or spouse? Yes No Not sure No contact with my significant other or spouse in past 30 days | Ms. Carter | In the past 30 days, have you had arguments or serious problems getting along with your significant other or spouse? • Yes • No • Not sure • No contact with my significant other or spouse in past 30 days | Yes = 1 No = 0 Not sure = -9 No recent contact w/ my significant other/spouse = -1 | If -2 (refused), show No-Skip Alert | | |
| (ASIF021L) | Have there been other periods in your life when you had serious problems getting along with a significant other or spouse? Yes No Not sure | Ms. Carter | Have there been other periods in your life when you had serious problems getting along with a significant other or spouse? Click Yes, No, or Unsure. | Yes = 1 No = 0 Unsure = -9 | | | |
| (ASIF016) | Would you say that during your lifetime you have had a close, long-lasting, personal relationship with any of your children? No children Yes No Not sure Never knew my children | Ms. Carter | Would you say that during your lifetime you have had a close, long-lasting, personal relationship with any of your children? • No children • Yes • No • Not sure • Never knew my children | No children = 2 Yes = 1 No = 0 Not sure = -9 Never knew my children = -1 | If ASIF016 = -1 or 2, go to ASIF023P | | |

FIG. 6PPPPPPP

| Question ID | Onscreen Text | Actor | Audio Recordings | ASI-MV Codes | Skip Logic | Consistency | Extreme Values |
|---|---|---|---|---|---|---|---|
| (ASIF022P) (Composite Question) | In the past 30 days, have you had arguments or serious problems getting along with any of your children?<br>Yes<br>No<br>Not sure<br>No contact with my children in past 30 days | Ms. Carter | In the past 30 days, have you had arguments or serious problems getting along with any of your children?<br>• Yes<br>• No<br>• Not sure<br>• No contact with my children in past 30 days | | If -2 (refused), show No-Skip Alert | | |
| (ASIF022L) | Have there been other periods in your life when you had serious problems getting along with any of your children?<br>Yes<br>No<br>Not sure | Ms. Carter | Have there been other periods in your life when you had serious problems getting along with any of your children?<br>• Yes<br>• No<br>• Not sure | Yes = 1<br>No = 0<br>Unsure = -9 | | | |
| F16A | How many children do you have under the age of 18 (birth or adopted, whether they live with you or not)? * * | Ms. Carter | How many children do you have under the age of 18 (birth or adopted, whether they live with you or not)?<br><br>If None click here. | - Coded as a 2 digit variable<br>- None = 0<br>Not sure = -9 | | | If F16A > 15, Extreme Alert and if not * * |
| F16B | How many days in the past 30 did at least one of your children live with you?<br>Days<br>None | Ms. Carter | How many days in the past 30 did at least one of your children live with you?<br><br>If None click here. | -Coded as a 2 digit variable<br>-None = 0<br>(MAX 30) | | | |

FIG. 6QQQQQQ

| Question ID | Onscreen Text | Actor | Audio Recordings | ASI-MV Codes | Skip Logic | Consistency | Extreme Values |
|---|---|---|---|---|---|---|---|
| F16C | Have any of your children ever been taken away from you because of a child protective order or other legal proceeding?<br>Yes<br>No<br>Unsure | Ms. Carter | Have any of your children ever been taken away from you because of a child protective order or other legal proceeding?<br><br>Click Yes, No, or Unsure. | Yes = 1<br>No = 0<br>Unsure = -9 | | | |
| (ASIF023P)<br>(Composite Question) | In the past 30 days, have you had arguments or serious problems getting along with any other significant family members?<br>Yes<br>No<br>Not sure | Ms. Carter | In the past 30 days, have you had arguments or serious problems getting along with any other significant family members?<br><br>Click Yes, No, or Unsure. | Yes = 1<br>No = 0<br>Unsure = -9 | If -2 (refused), show No-Skip Alert | | |
| (ASIF023L) | Have there been other periods in your life when you had serious problems getting along with any other significant family members?<br>Yes<br>No<br>Not sure | Ms. Carter | Have there been other periods in your life when you had serious problems getting along with any other significant family members?<br><br>Click Yes, No, or Unsure. | Yes = 1<br>No = 0<br>Unsure = -9 | | | |
| (ASIF017) | Would you say that you have had a close, long-lasting, personal relationship with any of your friends? * * | Ms. Carter | Would you say that you have had a close, long-lasting, personal relationship with any of your friends? * * | Yes = 1<br>No = 0<br>Not sure = -9<br>No friends = -1 | If ASIF017 = -1, go to ASIF025P | | |

FIG. 6RRRRRRR

| Question ID | Onscreen Text | Actor | Audio Recordings | ASI-MV Codes | Skip Logic | Consistency | Extreme Values |
|---|---|---|---|---|---|---|---|
| (ASIF024P) (Composite Question) | In the past 30 days, have you had arguments or serious problems getting along with any of your close friends? • Yes • No • Not sure • No contact with close friends in past 30 days | Ms. Carter | In the past 30 days, have you had arguments or serious problems getting along with any of your close friends? • Yes • No • Not sure • No contact with close friends in past 30 days | Yes = 1 No = 0 Not sure = -9 No recent contact w/ close friends = -1 | If -2 (refused), show No-Skip Alert | | |
| (ASIF024L) | Have there been other periods in your life when you had serious problems getting along with any of your close friends? • • • | Ms. Carter | Have there been other periods in your life when you had serious problems getting along with any of your close friends? • Yes • No • Not sure | Yes = 1 No = 0 Not sure = -9 | | | |
| (ASIF025P) (Composite Question) | In the past 30 days, have you had arguments or serious problems getting along with any of your neighbors? • • • | Ms. Carter | In the past 30 days, have you had arguments or serious problems getting along with any of your neighbors? • Yes • No • Not sure | Yes = 1 No = 0 Not sure = -9 No recent contact w/ neighbors = -1 | If -2 (refused), show No-Skip Alert | | |
| (ASIF025L) | Have there been other periods in your life when you had serious problems getting along with any of your neighbors? | Ms. Carter | Have there been other periods in your life when you had serious problems getting along with any of your neighbors? Click Yes, No, or Unsure. | Yes = 1 No = 0 Not sure = -9 | | | |

FIG. 6SSSSSSS

| Question ID | Onscreen Text | Actor | Audio Recordings | ASI-MV Codes | Skip Logic | Consistency | Extreme Values |
|---|---|---|---|---|---|---|---|
| (ASIF026P) (Composite Question) | In the past 30 days, have you had arguments or serious problems getting along with any of your co-workers? Yes No Not sure No co-workers | Ms. Carter | In the past 30 days, have you had arguments or serious problems getting along with any of your co-workers?<br>• Yes<br>• No<br>• Not sure<br>• No co-workers | Yes = 1<br>No = 0<br>Not sure = -9<br>No co-workers = -1 | If -2 (refused), show No-Skip Alert | | |
| (ASIF026L) | Have there been other periods in your life when you had serious problems getting along with any of your co-workers? | Ms. Carter | Have there been other periods in your life when you had serious problems getting along with any of your co-workers?<br>• Yes<br>• No<br>• Not sure<br>• No co-workers | Yes = 1<br>No = 0<br>Not sure = -9<br>No co-workers = -1 | | | |
| (ASIF027P) | In the past 30 days, have you been emotionally abused? [Side bar] | Ms. Carter | In the past 30 days, have you been emotionally abused? That means that people have yelled<br>•<br>•<br>• | Yes = 1<br>No = 0<br>Not sure = -9 | | | |
| (ASIF027L) | Have there been other times in your life when you were emotionally abused? | Ms. Carter | Have there been other times in your life when you were emotionally abused?<br>• Yes<br>• No<br>• Not sure | Yes = 1<br>No = 0<br>Not sure = -9 | | | |

FIG. 6TTTTTTT

| Question ID | Onscreen Text | Actor | Audio Recordings | ASI-MV Codes | Skip Logic | Consistency | Extreme Values |
|---|---|---|---|---|---|---|---|
| (ASIF028P) | In the past 30 days, have you been physically abused?<br>[Side bar] That means that you have been hit, pushed, or physically harmed.<br>Yes<br>No<br>Not sure | Ms. Carter | In the past 30 days, have you been physically abused?<br><br>That means that you have been hit, pushed, or physically harmed.<br><br>• Yes<br>• No<br>• Not sure | Yes = 1<br>No = 0<br>Not sure = -9 | | | |
| (ASIF028L) | Have there been other times in your life when you were physically abused?<br>Yes<br>No<br>Not sure | Ms. Carter | Have there been other times in your life when you were physically abused?<br><br>• Yes<br>• No<br>• Not sure | Yes = 1<br>No = 0<br>Not sure = -9 | | | |
| (ASIF029P) | In the past 30 days, have you been sexually abused?<br>[Side bar] That means that you have * * | Ms. Carter | In the past 30 days, have you been sexually abused?<br>That means that you have been forced or threatened to have sex or sexual contact against your will.<br>• Yes<br>• No<br>• Not sure | Yes = 1<br>No = 0<br>Not sure = -9 | | | |
| (ASIF029L) | Have there been other times in your life when you were sexually abused?<br>Yes<br>No<br>Not sure | Ms. Carter | Have there been other times in your life when you were sexually abused? | Yes = 1<br>No = 0<br>Not sure = -9 | | | |

FIG. 6UUUUUUU

| Question ID | Onscreen Text | Actor | Audio Recordings | ASI-MV Codes | Skip Logic | Consistency | Extreme Values |
|---|---|---|---|---|---|---|---|
| (ASIF030) (Composite Question) | In the past 30 days, estimate how many days you have had very serious conflicts with any family member or relative. Days None | Ms. Carter | In the past 30 days, estimate how many days you have had very serious conflicts with any family member or relative. If None, click this button. | -Coded as 2 digit variable (MAX = 30) -None = 0 | If -2 (refused), show No-Skip Alert | | |
| (ASIF032) (Composite Question) | In the past 30 days, how troubled or bothered have you been by family problems? Not at all Slightly Moderately Considerably Extremely | Ms. Carter | In the past 30 days, how troubled or bothered have you been by family problems? • Not at all • Slightly • Moderately • Considerably • Extremely | 0 = Not at all 1 = Slightly 2 = Moderately 3 = Considerably 4 = Extremely | | | |
| (ASIF034) (Composite Question) | How important is it to you right now to receive counseling or treatment for family problems? * * * | Ms. Carter | How important is it to you right now to receive counseling or treatment for family problems? • Not at all • • | 0 = Not at all 1 = Slightly 2 = Moderately 3 = Considerably 4 = Extremely | If -2 (refused), show No-Skip Alert | | |
| (ASIF031) | In the past 30 days, estimate how many days you have had very serious conflicts with anyone outside of your family. Days None | Ms. Carter | In the past 30 days, estimate how many days you have had very serious conflicts with anyone outside of your family. If None, click here. | -Coded as 2 digit variable (MAX = 30) -None = 0 | If -2 (refused), show No-Skip Alert | | |

FIG. 6VVVVVVV

| Question ID | Onscreen Text | Actor | Audio Recordings | ASI-MV Codes | Skip Logic | Consistency | Extreme Values |
|---|---|---|---|---|---|---|---|
| (ASIF033) | In the past 30 days, how troubled or bothered have you been by problems with people other than family?<br><br>[Side bar] Problems might include feeling isolated or lonely, being unable to interact, or having serious conflicts with people.<br>.<br>.<br>. | Ms. Carter | In the past 30 days, how troubled or bothered have you been by problems with people other than family?<br><br>Problems might include feeling isolated or lonely, being unable to interact, or having serious conflicts with people.<br><br>• Not at all<br>• Slightly<br>• Moderately<br>• Considerably<br>• Extremely | 0 = Not at all<br>1 = Slightly<br>2 = Moderately<br>3 = Considerably<br>4 = Extremely | | | |
| (ASIF035) | How important is treatment right now for problems with people other than family?<br>.<br>.<br>. | Ms. Carter | How important is treatment right now for problems with people other than family?<br>.<br>.<br>. | 0 = Not at all<br>1 = Slightly<br>2 = Moderately<br>3 = Considerably<br>4 = Extremely | | | |
| (ASIF036) | | | | (Calculated Variable) Family Severity Rating | | | |
| COMPFAM (Calculated Variable) | | | | Family Composite Score (.000-1.000) | COMPUTE famneed = ASIF034 + ASIF035 .<br>.<br>.<br>. | Variables in the data base: | |

FIG. 6WWWWWW

| Question ID | Onscreen Text | Actor | Audio Recordings | ASI-MV Codes | Skip Logic | Consistency | Extreme Values |
|---|---|---|---|---|---|---|---|
| | | | | | asif032 : How troubled or bothered are you by family problems<br>asif034 : How important is it to you to receive counseling<br>asif018p: Problems with Mother past 30 days<br>asif019p: Problems with Father past 30 days<br>asif020p: Problems with Siblings past 30 days<br>asif021p : Problems with Spouse past 30 days<br>asif022p: Problems with Children past 30 days<br>asif023p : Problems with Other Family Members past 30 days<br>asif024p: Problems with Close Friends past 30 days<br>asif025p: Problems with Neighbors past 30 days<br>asif026p : Problems with Co-Workers past 30 days<br><br>New variables:<br>FAMILY : Temporary variable<br>FAMCOUN1 : Temporary variable (count the number of YES (1) responses.<br>FAMCOUN2 : Temporary variable (count the number of YES (1) or NO (0) responses or Unsure (-9).<br>FAMTEMP : Temporary variable<br>FAMRATIO : Temporary variable (compute ratio)<br>COMPFAM : Family Composite Score<br>Recodes:<br>asif018p asif019p asif020p asif021p asif022p asif023p asif024p asif025p asif026p   (-1 OR -9 OR -2) = missing (or blank)<br><br>Temporary recode:  asif003   (0=2) (1=1) (2=0)  .<br>. . | | |

FIG. 6XXXXXXX

| Question ID | Onscreen Text | Actor | Audio Recordings | ASI-MV Codes | Skip Logic | Consistency | Extreme Values |
|---|---|---|---|---|---|---|---|
| | | | | | | If asif026p = 1 or 0 or -9 Then FAMCOUN2 = FAMCOUN2 + 1<br>FAMTEMP = (FAMCOUN1 / FAMCOUN2)<br>FAMRATIO = FAMTEMP / 5<br>COMPFAM = FAMILY + FAMRATIO<br>RECODE: If >= 1.00 then 1.00 | |
| | | Ms. Carter | Thanks a lot. Well, looks like you're almost done here. Hope it's all going well for you. | | | | |
| | | Angela | Last one! Now, Dr. Hamilton needs to ask you some questions about your emotional health. Her door is straight ahead. We'll see you in just a bit. | | | | |
| Psychiatric Section | | | | | | | |
| | | Dr. Hamilton | Hello. Welcome. I want to ask you some questions about your emotional health and how you've been feeling. | | | | |
| No-Skip Alert Dialogue box | Are you sure you want to move on without answering this question?<br>Yes<br>No | Dr. Hamilton | Are you sure you want to move on without answering this question?<br>Yes, or<br>No | If Yes, record -2 for skipped question | If Yes, go to next question.<br>If No, return to question. | | |

FIG. 6YYYYYYY

| Question ID | Onscreen Text | Actor | Audio Recordings | ASI-MV Codes | Skip Logic | Consistency | Extreme Values |
|---|---|---|---|---|---|---|---|
| No-Skip Alert Dialogue box | This question is important, so please try to answer.<br>Yes<br>No | Dr. Hamilton | This question is important, so would you please try to choose an answer?<br>Yes<br>No | If No, record -2 for skipped question | If No, go to next question.<br>If Yes, • • • | | |
| Extreme Alert Dialogue box | Is this the answer you want to give ____?<br>Yes<br>No | Dr. Hamilton | Is this the answer you want to give?<br>Yes<br>No | If Yes, record answer to question | If No, return to question | | If Yes, add question and answer to the Extreme Values Rpt |
| Enter Prompt | none | Dr. Hamilton | Remember, when you finish selecting your answer, click on the NEXT button to go to the next question. | none | | | |
| (ASIP001) | How many times in your life have you been treated for a psychological or emotional problem while in an inpatient setting or hospital?<br>[Side bar]<br>This includes psychological treatment while in an inpatient substance abuse unit or on an inpatient medical unit.<br>Times<br>None | Dr. Hamilton | Estimate how many times in your life you have been admitted to an inpatient setting or hospital for a psychological or emotional problem. Do not include hospitalizations for drug and alcohol related problems.<br>If Never, click this button. | - Coded as 2 digit variable<br>- Never = 0 | | If ASIG019 = 5 & ASIP001 = 0, Consistency Alert<br>If no: FLAG (if they don't change it, accept answer and add both questions and answers to • • • | If ASIP001 > 10, Extreme Alert and if not changed, add question and answer to the Extreme Values Report |

FIG. 6ZZZZZZZ

| Question ID | Onscreen Text | Actor | Audio Recordings | ASI-MV Codes | Skip Logic | Consistency | Extreme Values |
|---|---|---|---|---|---|---|---|
| (ASIP001) f/up | Since the last time you took this ASI interview, how many times have you been treated for a psychological or emotional problem while in an inpatient setting or hospital? This includes psychological treatment while in an inpatient substance abuse unit or on an inpatient medical unit.<br><br>Times<br>None | Dr. Hamilton | Since the last time you took this ASI interview, how many times have you been treated for a psychological or emotional problem while in an inpatient setting or hospital? This includes psychological treatment while in an inpatient substance abuse unit or on an inpatient medical unit.<br><br>If Never, click this button. | - Coded as 2 digit variable<br>- Never = 0 | | | If(ASIP001>10, Extreme Alert and if not changed, add question and answer to the Extreme Values Report |
| (ASIP002) | [Side bar]<br>Estimate how many different times in your life you have entered outpatient treatment or counseling for emotional or psychological problems.<br><br>Do not include drug or alcohol, family, or employment counseling.<br><br>Times<br>None | Dr. Hamilton | Estimate how many different times in your life you have entered outpatient treatment or counseling for emotional or psychological problems.<br><br>Do not include drug or alcohol, family, or employment counseling.<br><br>If Never, click this button. | - Coded as 2 digit variable<br>- Never = 0 | | | If ASIP002 > 15, Extreme Alert and if not changed, add question and answer to the Extreme Values Report |

FIG. 6AAAAAAAA

| Question ID | Onscreen Text | Actor | Audio Recordings | ASI-MV Codes | Skip Logic | Consistency | Extreme Values |
|---|---|---|---|---|---|---|---|
| (ASIP002) f/up | Since the last time you took this ASI interview, estimate how many different times you have entered outpatient treatment or counseling for emotional or psychological problems.<br><br>[Side bar]<br>.<br>.<br>. | Dr. Hamilton | Since the last time you took this ASI interview, estimate how many different times you have entered outpatient treatment or counseling for emotional or psychological problems. Do not include drug or alcohol, family, or employment counseling.<br><br>If Never, click this button. | - Coded as 2 digit variable<br>- Never = 0 | | | if ASIP002 > 15, Extreme Alert and if not changed, add question and answer to the Extreme Values Rpt |
| PZA1=Depression or Mood Disorder<br>PZA2=Manic Depression or Bi-polar illness<br>PZA3=Anxiety or Nervous disorder<br>PZA4=Phobias or fears such as Agoraphobia or a Social phobia<br>PZA5=Panic Disorder<br>PZA6=Obsessive Compulsive | To your knowledge, have you ever received a diagnosis for an emotional or psychological problem other than drug or alcohol abuse? Please select all that apply.<br><br>-Depression or Mood Disorder<br>-Manic Depression or Bi-polar illness<br>-Anxiety or Nervous disorder<br>-Phobias or fears such as Agoraphobia or a Social phobia<br>.<br>.<br>. | | To your knowledge, have you ever received a diagnosis for an emotional or psychological problem other than drug or alcohol abuse? Please select all that apply.<br><br>-Depression or Mood Disorder<br>-Manic Depression or Bi-polar illness<br>-Anxiety or Nervous disorder<br>-Phobias or fears such as Agoraphobia or a Social phobia<br>-Panic Disorder<br>-Obsessive Compulsive<br>.<br>.<br>. | Each variable will be given a separate value<br><br>1 = Yes [Selected]<br>0 = No [Not selected]<br><br>PZA1=Depression or Mood Disorder<br>PZA2=Manic Depression or Bi-polar illness<br>PZA3=Anxiety or Nervous disorder<br>PZA4=Phobias or fears such as Agoraphobia or<br>.<br>.<br>. | | | |

FIG. 6BBBBBBBB

| Question ID | Onscreen Text | Actor | Audio Recordings | ASI-MV Codes | Skip Logic | Consistency | Extreme Values |
|---|---|---|---|---|---|---|---|
| Disorder (OCD) PZA7=Eating Disorders such as anorexia and bulimia PZA8=Post-Traumatic Stress Disorder (PTSD) PZA9=Multiple Personality Disorder (MPD) PZA10=Personality Disorders such as Borderline, Antisocial, Passive-aggressive, Narcissistic, or Dependent. PZA11=Psychotic or Thought disorder PZA12=Schizophrenia or a Paranoid, | bulimia -Post-Traumatic Stress Disorder (PTSD) -Multiple Personality Disorder (MPD) -Personality Disorders such as Borderline, Antisocial, Passive-aggressive, Narcissistic, or Dependent. -Psychotic or Thought disorder -Schizophrenia or a Paranoid, Delusional disorder -Dissociative Disorder -No diagnosis -Unsure | | -Psychotic or Thought disorder -Schizophrenia or a Paranoid, Delusional disorder -Dissociative Disorder -No diagnosis -Unsure | anorexia and bulimia PZA8=Post-Traumatic Stress Disorder (PTSD) PZA9=Multiple Personality Disorder (MPD) PZA10=Personality Disorders such as Borderline, Antisocial, Passive-aggressive, Narcissistic, or Dependent. PZA11=Psychotic or Thought disorder PZA12=Schizophrenia or a Paranoid, Delusional disorder PZA13=Dissociative Disorder PZA14=No PZA15=Unsure | | | |

FIG. 6CCCCCCC

| Question ID | Onscreen Text | Actor | Audio Recordings | ASI-MV Codes | Skip Logic | Consistency | Extreme Values |
|---|---|---|---|---|---|---|---|
| Delusional disorder PZA13=Dissoc iative Disorder PZA14=No PZA15=Unsur | | | | | | | |
| (ASIP003) | Do you currently receive a pension or money for a psychiatric disability? *[side bar]* Do not include pensions for physical or medical problems. Yes No | Dr. Hamilton | Do you currently receive a pension or money for a psychiatric disability? Do not include pensions for physical or medical problems. Click Yes or No. | 1 = Yes 0 = No | | If ASIP003 = 1 & ASIE015 =0, Consistency Alert if no: FLAG (if they don't . . . | |
| (ASIP004P) (Composite Question) | In the past 30 days, have you felt seriously depressed? *[side bar]* This means you were feeling very sad, hopeless and overly guilty. You many have been crying a lot or had difficulty getting out of bed. Yes Only when high or in withdrawal from alcohol or drugs No | Dr. Hamilton | In the past 30 days, have you felt seriously depressed? This means you were feeling very sad, hopeless and overly guilty. You many have been crying a lot or had difficulty getting out of bed. • Yes . . . | - Yes = 1 - Only when high or in w/d from alcohol or drugs = 2 - No = 0 | If ASIP004P = 1, enable ASIP012 If -2 (refused), show No-Skip Alert | | |

FIG. 6DDDDDDD

| Question ID | Onscreen Text | Actor | Audio Recordings | ASI-MV Codes | Skip Logic | Consistency | Extreme Values |
|---|---|---|---|---|---|---|---|
| (ASIP004L) | Have there been other periods of time in your life when you felt seriously depressed?<br><br>*side bar]*<br>This means you were feeling very sad, hopeless and overly guilty. You may have been crying a lot or had difficulty getting out of bed.<br><br>Yes<br>Only when high or in withdrawal from alcohol or drugs<br>No | Dr. Hamilton | Have there been other periods of time in your life when you felt seriously depressed?<br><br>This means you were feeling very sad, hopeless and overly guilty.<br><br>You may have been crying a lot or had difficulty getting out of bed.<br><br>• Yes<br>• Only when high or in withdrawal from alcohol or drugs<br>• No | - Yes = 1<br>- Only when high or in w/d from alcohol or drugs = 2<br>- No = 0 | | | |
| (ASIP005P)<br><br>(Composite Question) | In the past 30 days, have you had serious anxiety or tension?<br><br>[side bar]<br>This means you were constantly feeling tense, uptight, unreasonably worried, or unable to relax.<br><br>Yes<br>• •<br>• • | Dr. Hamilton | In the past 30 days, have you had serious anxiety or tension?<br><br>This means you were constantly feeling tense, uptight, unreasonably worried, or unable to relax.<br><br>• Yes<br>• Only when high or in withdrawal from alcohol or drugs<br>• No | - Yes = 1<br>- Only when high or in w/d from alcohol or drugs = 2<br>- No = 0 | If ASIP005P = 1, enable ASIP012<br><br>If -2 (refused), show No-Skip Alert | | |

FIG. 6EEEEEEEE

| Question ID | Onscreen Text | Actor | Audio Recordings | ASI-MV Codes | Skip Logic | Consistency | Extreme Values |
|---|---|---|---|---|---|---|---|
| (ASIP005L) | Have there been other periods of time in your life when you had serious anxiety or tension?<br><br>For example, you were constantly feeling tense, uptight, unreasonably worried, or unable to relax.<br>Yes<br>Only when high or in withdrawal from alcohol or drugs<br>No | Dr. Hamilton | Have there been other periods of time in your life when you had serious anxiety?<br><br>For example, you were constantly feeling tense, uptight, unreasonably worried, or unable to relax.<br>• Yes<br>• Only when high or in withdrawal from alcohol or drugs<br>• No | - Yes = 1<br>- Only when high or in w/d from alcohol or drugs = 2<br>- No = 0 | | | |
| (ASIP006P)<br>(Composite Question) | In the past 30 days, have you heard voices or saw things that other people couldn't see and hear?<br>Yes  •<br>•<br>• | Dr. Hamilton | In the past 30 days, have you heard voices or saw things that other people couldn't see and hear?<br>• Yes  •<br>•<br>• | - Yes = 1<br>- Only when high or in w/d from alcohol or drugs = 2<br>- No = 0 | If ASIP006P = 1, enable ASIP012<br><br>If -2 (refused), show No-Skip Alert | | |
| (ASIP006L) | Have there been other periods of time in your life when you heard voices or saw things that other people couldn't see and hear?<br>Yes  •<br>•<br>• | Dr. Hamilton | Have there been other periods of time in your life when you heard voices or saw things that other people couldn't see and hear?<br>• Yes  •<br>•<br>• | - Yes = 1<br>- Only when high or in w/d from alcohol or drugs = 2<br>- No = 0 | | | |

FIG. 6FFFFFFFF

| Question ID | Onscreen Text | Actor | Audio Recordings | ASI-MV Codes | Skip Logic | Consistency | Extreme Values |
|---|---|---|---|---|---|---|---|
| (ASIP007P)<br><br>(Composite Question) | In the past 30 days, have you had trouble concentrating, understanding or remembering?<br><br>Yes<br>Only when high or in withdrawal from alcohol or drugs<br>No | Dr. Hamilton | In the past 30 days, have you had trouble concentrating, understanding or remembering?<br><br>• Yes<br>• Only when high or in withdrawal from alcohol or drugs<br>• No | - Yes = 1<br>- Only when high or in w/d from alcohol or drugs = 2<br>- No = 0 | If ASIP007P = 1, enable ASIP012<br><br>If -2 (refused), show No-Skip Alert | | |
| (ASIP007L) | Have there been other periods of time in your life when you had trouble concentrating, understanding or remembering?<br><br>Yes<br>Only when high or in withdrawal from alcohol or drugs<br>No | Dr. Hamilton | Have there been other periods of time in your life when you had trouble concentrating, understanding or remembering?<br><br>• Yes<br>• Only when high or in withdrawal from alcohol or drugs<br>• No | - Yes = 1<br>- Only when high or in w/d from alcohol or drugs = 2<br>- No = 0 | | | |
| (ASIP008P)<br><br>(Composite Question) | In the past 30 days, have you had trouble controlling your temper or violent behavior?<br><br>Yes<br>•<br>• | Dr. Hamilton | In the past 30 days, have you had trouble controlling your temper or violent behavior?<br><br>• Yes<br>•<br>• | - Yes = 1<br>- Only when high or in w/d from alcohol or drugs = 2<br>- No = 0 | If ASIP008P = 1, enable ASIP012<br><br>If -2 (refused), show No-Skip Alert | | |

FIG. 6GGGGGGGG

| Question ID | Onscreen Text | Actor | Audio Recordings | ASI-MV Codes | Skip Logic | Consistency | Extreme Values |
|---|---|---|---|---|---|---|---|
| (ASIP008L) | Have there been other periods of time in your life when you had trouble controlling your temper or violent behavior? | Dr. Hamilton | Have there been other periods of time in your life when you had trouble controlling your temper or violent behavior? | - Yes = 1<br>- Only when high or in w/d from alcohol or drugs = 2<br>- No = 0 | | | |
| (ASIP009P)<br>(Composite Question) | In the past 30 days, have you seriously considered a plan for killing yourself? | Dr. Hamilton | In the past 30 days, have you seriously considered a plan for killing yourself? | - Yes = 1<br>- Only when high or in w/d from alcohol or drugs = 2<br>- No = 0 | If ASIP009P = 1, enable ASIP012<br>If -2 (refused), show No-Skip Alert | | |
| (ASIP009L) | Have there been other times in your life when you seriously considered a plan for killing yourself? | Dr. Hamilton | Have there been other times in your life when you seriously considered a plan for killing yourself? | - Yes = 1<br>- Only when high or in w/d from alcohol or drugs = 2<br>- No = 0 | | | |
| (ASIP010P)<br>(Composite Question) | In the past 30 days, have you attempted suicide or tried to kill yourself? | Dr. Hamilton | In the past 30 days, have you attempted suicide or tried to kill yourself? | - Yes = 1<br>- Only when high or in w/d from alcohol or drugs = 2<br>- No = 0 | If ASIP010P = 1, enable ASIP012<br>If -2 (refused), show No-Skip Alert | | |

FIG. 6IIIIIIIIIIIIII

| Question ID | Onscreen Text | Actor | Audio Recordings | ASI-MV Codes | Skip Logic | Consistency | Extreme Values |
|---|---|---|---|---|---|---|---|
| (ASIP010L) | Have there been other times in your life when you attempted suicide or tried to kill yourself?<br><br>Yes<br>Only when high or in withdrawal from alcohol or drugs<br>No | Dr. Hamilton | Have there been other times in your life when you attempted suicide or tried to kill yourself?<br><br>• Yes<br>• Only when high or in withdrawal from alcohol or drugs<br>• No | 2 = 0    - Yes = 1<br>- Only when high or in w/d from alcohol or drugs = 2<br>- No = 0 | | | |
| (ASIP011P)<br>(Composite Question) | In the past 30 days, were you prescribed medication for emotional or psychiatric problems? Answer Yes if medication was prescribed, even if you did not take it.<br><br>Yes<br>No | Dr. Hamilton | In the past 30 days, were you prescribed medication for emotional or psychiatric problems?<br><br>Answer Yes if medication was prescribed, even if you did not take it.<br>Click Yes or No. | Yes = 1<br>No = 0 | If -2 (refused), show No-Skip Alert | | |
| (ASIP011L) | Have there been other times in your life when you were prescribed medication for emotional or psychiatric problems? Answer Yes if medication was prescribed, even if you did not take it.<br><br>Yes<br>No | Dr. Hamilton | Have there been other times in your life when you were prescribed medication for emotional or psychiatric problems?<br><br>Answer Yes if medication was prescribed, even if you did not take it.<br>Click Yes or No. | Yes = 1<br>No = 0 | | | |

FIG. 6IIIIIII

| Question ID | Onscreen Text | Actor | Audio Recordings | ASI-MV Codes | Skip Logic | Consistency | Extreme Values |
|---|---|---|---|---|---|---|---|
| (ASIP012) (Composite Question) | In the past 30 days, estimate how many days you have had any of the psychological or emotional problems mentioned earlier. These are:<br><br>-depression<br>-anxiety<br>•<br>•<br>• | Dr. Hamilton | In the past 30 days, estimate how many days you have had any of the psychological or emotional problems mentioned earlier.<br><br>These are: depression, anxiety, hallucinations, poor concentration,<br>•<br>•<br>• | Answer coded as 2 digit variable (MAX 30)<br><br>0 = None<br><br>(-1 = 0) | If ASIP004P & ASIP005P & ASIP006P & ASIP007P & ASIP008P & ASIP009P & ASIP010P = 0, skip ASIP012. | | |
| PZB | Are you currently receiving help from a professional for your psychological or emotional problems?<br><br>Yes<br>No | | Are you currently receiving help from a professional for your psychological or emotional problems?<br><br>Click Yes or No. | Yes = 1<br>No = 0 | | | |
| (ASIP013) (Composite Question) | In the past 30 days, how troubled or bothered have you been by emotional of psychological problems?<br><br>Not at all<br>Slightly<br>Moderately<br>Considerably<br>Extremely | Dr. Hamilton | In the past 30 days, how troubled or bothered have you been by emotional of psychological problems?<br><br>• Not at all<br>• Slightly<br>• Moderately<br>• Considerably<br>• Extremely | 0 = Not at all<br>1 = Slightly<br>2 = Moderately<br>3 = Considerably<br>4 = Extremely | If -2 (refused), show No-Skip Alert | | |

FIG. 6JJJJJJJ

| Question ID | Onscreen Text | Actor | Audio Recordings | ASI-MV Codes | Skip Logic | Consistency | Extreme Values |
|---|---|---|---|---|---|---|---|
| (ASIP014) (Composite Question) | How important is it that you receive treatment for psychological or emotional problems right now? Not at all Slightly Moderately Considerably Extremely | Dr. Hamilton | How important is it that you receive treatment for psychological or emotional problems right now? • Not at all • Slightly • Moderately • Considerably • Extremely | 0 = Not at all 1 = Slightly 2 = Moderately 3 = Considerably 4 = Extremely | If -2 (refused), show No-Skip Alert | | |
| (ASIP015) | Have you been feeling down, blue, and depressed today? Not at all Slightly Moderately Considerably Extremely | Dr. Hamilton | Have you been feeling down, blue, and depressed today? • Not at all • Slightly • Moderately • Considerably • Extremely | 0 = Not at all 1 = Slightly 2 = Moderately 3 = Considerably 4 = Extremely NOTE LEFT IN THE VA CODES • • | | | |
| (ASIP015A) | Have you been feeling helpless and hopeless today? Not at all Slightly Moderately Considerably Extremely | Dr. Hamilton | Have you been feeling helpless and hopeless today? • Not at all • Slightly • Moderately • Considerably • Extremely | 0 = Not at all 1 = Slightly 2 = Moderately 3 = Considerably 4 = Extremely **see ASIP015 (new variable) | | | |

FIG. 6KKKKKK

| Question ID | Onscreen Text | Actor | Audio Recordings | ASI-MV Codes | Skip Logic | Consistency | Extreme Values |
|---|---|---|---|---|---|---|---|
| (ASIP016) | Have you been feeling hostile today?<br><br>Not at all<br>Slightly<br>Moderately<br>Considerably<br>Extremely | Dr. Hamilton | Have you been feeling hostile today?<br><br>• Not at all<br>• Slightly<br>• Moderately<br>• Considerably<br>• Extremely | 0 = Not at all<br>1 = Slightly<br>2 = Moderately<br>3 = Considerably<br>4 = Extremely<br><br>VA CODING only- | | | |
| (ASIP016A) | Have you been feeling angry today?<br><br>Not at all<br>Slightly<br>Moderately<br>Considerably<br>Extremely | Dr. Hamilton | Have you been feeling angry today?<br><br>• Not at all<br>• Slightly<br>• Moderately<br>• Considerably<br>• Extremely | 0 = Not at all<br>1 = Slightly<br>2 = Moderately<br>3 = Considerably<br>4 = Extremely<br><br>**see ASIP016 (new variable) | | | |
| (ASIP016B) | Have you been feeling irritable today?<br><br>Not at all<br>Slightly<br>Moderately<br>Considerably<br>Extremely | Dr. Hamilton | Have you been feeling irritable today?<br><br>• Not at all<br>• Slightly<br>• Moderately<br>• Considerably<br>• Extremely | 0 = Not at all<br>1 = Slightly<br>2 = Moderately<br>3 = Considerably<br>4 = Extremely<br><br>**see ASIP016 (new variable) | | | |

FIG. 6LLLLLLLL

| Question ID | Onscreen Text | Actor | Audio Recordings | ASI-MV Codes | Skip Logic | Consistency | Extreme Values |
|---|---|---|---|---|---|---|---|
| (ASIP017) | Have you been feeling tense today?<br><br>Not at all<br>Slightly<br>Moderately<br>Considerably<br>Extremely | Dr. Hamilton | Have you been feeling tense today?<br><br>• Not at all<br>• Slightly<br>• Moderately<br>• Considerably<br>• Extremely | 0 = Not at all<br>1 = Slightly<br>2 = Moderately<br>3 = Considerably<br>4 = Extremely<br><br>VA CODING only- | | | |
| (ASIP017A) | Have you been feeling very worried today?<br><br>Not at all<br>Slightly<br>Moderately<br>Considerably<br>Extremely | Dr. Hamilton | Have you been feeling very worried today?<br><br>• Not at all<br>• Slightly<br>• Moderately<br>• Considerably<br>• Extremely | 0 = Not at all<br>1 = Slightly<br>2 = Moderately<br>3 = Considerably<br>4 = Extremely<br><br>**see ASIP017 (new variable) | | | |
| (ASIP019) | Have you had trouble concentrating today?<br><br>Not at all<br>Slightly<br>Moderately<br>Considerably<br>Extremely | Dr. Hamilton | Have you had trouble concentrating today?<br><br>• Not at all<br>• Slightly<br>• Moderately<br>• Considerably<br>• Extremely | 0 = Not at all<br>1 = Slightly<br>2 = Moderately<br>3 = Considerably<br>4 = Extremely<br><br>VA CODING - | | | |

FIG. 6MMMMMM

| Question ID | Onscreen Text | Actor | Audio Recordings | ASI-MV Codes | Skip Logic | Consistency | Extreme Values |
|---|---|---|---|---|---|---|---|
| (ASIP019A) | Have you had trouble thinking clearly today? <br><br> Not at all <br> Slightly <br> Moderately <br> Considerably <br> Extremely | Dr. Hamilton | Have you had trouble thinking clearly today? <br><br> • Not at all <br> • Slightly <br> • Moderately <br> • Considerably <br> • Extremely | 0 = Not at all <br> 1 = Slightly <br> 2 = Moderately <br> 3 = Considerably <br> 4 = Extremely <br><br> ** see ASIP019 (new variable) | | | |
| (ASIP018) | Have you been hearing voices today? <br><br> Not at all <br> Slightly <br> Moderately <br> Considerably <br> Extremely | Dr. Hamilton | Have you been hearing voices today? <br><br> • Not at all <br> • Slightly <br> • Moderately <br> • Considerably <br> • Extremely | 0 = Not at all <br> 1 = Slightly <br> 2 = Moderately <br> 3 = Considerably <br> 4 = Extremely <br><br> VA CODING - <br> . <br> . <br> . | | | |
| (ASIP020) | Have you been thinking of hurting yourself today? <br><br> Not at all <br> Slightly <br> Moderately <br> Considerably <br> Extremely | Dr. Hamilton | Have you been thinking of hurting yourself today? <br><br> • Not at all <br> • Slightly <br> • Moderately <br> • Considerably <br> • Extremely | 0 = Not at all <br> 1 = Slightly <br> 2 = Moderately <br> 3 = Considerably <br> 4 = Extremely <br><br> VA CODING - <br> . <br> . <br> . | | | |

FIG. 6NNNNNNN

| Question ID | Onscreen Text | Actor | Audio Recordings | ASI-MV Codes | Skip Logic | Consistency | Extreme Values |
|---|---|---|---|---|---|---|---|
| (ASIP021) | | | | (Calculated Variable) Psychiatric Severity Rating | compute psychsev = ASIP004P + ASIP005P + ASIP005P + ASIP007P + ASIP008P + ASIP009P + ASIP010P + ASIP011P. compute psychdur= ASIP004L + ASIP005L, +ASIP006L + | | |
| COMPPSY (Calculated Variable) | | | | Psychiatric Composite Score (.000-1.000) | Variables in data base: asip004p : Experienced serious depression asip005p: anxiety | | |
| | | Dr. Hamilton | That's all I have! Thank you for your time. | | | | |
| | | Angela | Great. Now that you've made it through the all the interviews, it's time to print out your certificate! Just give the button on the screen a click, and the printer will generate your customized certificate. | | | | |
| | | George | Thanks for your time today! | | | | |
| CONSISTotal | | | none | Sum of all inconsistencies (00-27) | | | |

FIG. 60000000000

| Question ID | Onscreen Text | Actor | Audio Recordings | ASI-MV Codes | Skip Logic | Consistency | Extreme Values |
|---|---|---|---|---|---|---|---|
| SKIPTotal | none | | none | Sum of all 2 responses | | | |

FIG. 6PPPPPPPP

NATIONAL ADDICTIONS VIGILANCE, INTERVENTION AND PREVENTION PROGRAM

RELATED APPLICATION

This application claims the benefit of U.S. Provisional Application No. 60/755,489 filed Dec. 29, 2005, the entire teachings of which are incorporated herein by reference.

BACKGROUND OF THE INVENTION

Pharmaceutical companies marketing drugs with abuse potential are required to manage the abuse risk, along with other risks, associated with their drugs. A Risk Management Action Plan (RiskMAP) and the implementation thereof, is required by the Food and Drug Administration, as a part of the New Drug Application (NDA) from the Pharmaceutical companies. Post marketing surveillance forms an important part of the RiskMAP to identify the risks associated with the target drug(s).

A. Thomas McLellan, Ph.D. and colleagues at the University of Pennsylvania in 1980 developed the Addiction Severity Index (ASI), a multidimensional assessment tool that is administered via semistructured interview to primarily patients entering substance abuse treatment centers. (McLellan A. T., Luborsky L, Woody G. E. & O'Brien C. P. (1980). *An improved diagnostic evaluation instrument for substance abuse patients. The Addiction Severity Index. The Journal of Nervous and Mental abuse patients. The Addiction Severity Index. The Journal of Nervous and Mental Disease*. January; 168 (1), 26-33, herein incorporated by reference.). The ASI gathers information on various problem areas of the respondent, including medical status, employment and support status, drug use, alcohol use, legal status, family and social relationships, and psychiatric status. Respondents are asked to answer specific questions about the problems they have experienced both recently—i.e. in the last 30 days—and over their lifetimes. Thus, both urgent concerns and longstanding, chronic problems are identified by the ASI. Respondents can also be asked to rate the extent of their difficulties and their need for treatment including indicating difficulties and needs in the problem areas listed above. Respondents' responses to the ASI inquiries are summarized into composite scores, which are considered to be objective and are used to measure change over time in response to treatment. As a result the ASI has become a standard assessment measure not only in the drug abuse field but also in substance abuse in general.

The ASI is used world-wide and is required in more than 30 states. It has been translated into 13 languages. It has also been expanded to specialized populations such as cocaine-abusing mothers, cocaine-freebase users, opiate dependent people, federal prisoners, psychiatrically ill substance abusers, homeless people, and individuals with antisocial personality disorder.

The ASI was adapted by A. Thomas McLellan, Ph.D. in his DENS software to do post marketing surveillance as a part of the Researched Abuse, Diversion, and Addiction-Related Surveillance (RADARS) System, but it suffered several drawbacks. First, the RADARS System consists of proprietary programs, of unknown accuracy or validity with little scientific basis and high cost. Second, for the ASI-DENS data to be meaningful, the clinicians, who conduct interviews of the substance users, require extensive training in administration, scoring and entering data into a database. To ensure reliability and validity of data, this ASI-based system is expensive to administer, score, and enter. Such cost concerns are significant for clinical facilities in the current era of financial cutbacks for social services. Third, the ASI assessed the abuse of a particular prescription drug without identifying the specific brands, the route of administration, or the source of the drug. Finally, deficient of a centralized system to collect and compute the data on substance abuse from a wide spectrum of locales and groups, the ASI did not permit consolidating the substance abuse data from one treatment community to the next.

Although improvements have been made to eliminate some of these deficiencies in the ASI, there is a need for a substance abuse surveillance system that can provide current substance abuse data and allow third parties to access the data in a user-friendly way.

SUMMARY OF THE INVENTION

The present invention addresses the foregoing problems of the prior art.

The present invention relates an automated survey system in general. The survey system can include a source of respondent responses to a self-administered virtual interview on a vertical market, and a data collecter coupled to receive from the source multiple respondent responses and analyzing the same in near real-time to form data on the vertical market, the data collector allowing access to the data by third parties, wherein the data collector is coupled to the source in a manner enabling delay-free, continuous feed of the respondent responses. Here, a vertical market can be a group of similar businesses and customers that engage in trade based on specific and specialized needs. Some common examples of vertical markets are healthcare, government, education, food and beverage, fast-moving consumer goods, real estate, manufacturing, oil and gas, banking, energy, retail, technology, telecommunications, transportation, and insurance. In a preferred embodiment, the present invention further includes an interview publishing system that enables a non-technical/non-software personnel to modify or update the contents of the self-administered interview.

Specifically, the present invention provides a multimedia version of the widely used ASI or equivalent and is directed to a substance abuse surveillance system. In one embodiment, the present invention provides a substance surveillance abuse system that includes a source of respondent responses to a self-administered virtual interview: A data collector is coupled to receive from the source multiple respondent responses and analyzes the same in near real-time to form current substance abuse data. The data collector allows access to the current substance abuse data by third parties. The data collector is coupled to the source in a manner enabling delay-free, continuous feed of the respondent responses.

In another embodiment, the present invention relates to a substance abuse surveillance system that includes an interactive medium configured to provide a self-administered virtual interview for obtaining information on a respondent's experience with one or more substances. The substance abuse surveillance system has a data collector in electronic communication with the interactive medium and configured to receive and analyze the information in near real-time to generate current substance abuse data. In a preferred embodiment, the present invention further includes an interview publishing system that enables a non-technical/non-software personnel to modify or update the contents of the self-administered interview.

In one embodiment, the present invention provides a method for obtaining data on substance abuse. The steps to the method include a step of receiving respondent responses to self-administered virtual interviews, each self-administered virtual interview regarding a respective respondent's experience with one or more substances. In another step, the invention method analyzes the received respondent responses and forming current substance abuse data in near real-time.

In another embodiment, the present invention provides a method for obtaining data on substance abuse. The method includes the step of preforming near real-time analysis, based on respondent responses regarding one or more substances. The responses are provided in self-administered virtual interviews via a global computer network. The real time analysis may be performed at a site of the self-administered virtual interview.

In another embodiment, the present invention provides a computer program product that includes a computer usable medium, and a set of computer program instructions embodied on the computer useable medium for forming current substance abuse data. When executed by a computer, the set of computer program instructions causes the computer to receive respondent responses to self-administered virtual interviews, each virtual interview regarding each respective respondent's experience with one or more substances, and to analyze the received respondent responses and form current substance abuse data in near real-time.

In another embodiment, the present invention is a computer system for obtaining data on substance abuse. The computer system includes an input means for conducting a self-administered virtual interview regarding a respondent's experience with one or more substances. The input means employs an interactive media. Digital processor means are coupled to the input means for receiving respondent responses from the self-administered virtual interview and analyze the respondent responses in near real-time forming current substance abuse data. Output means coupled to the digital processor means enable a third party to access to the current substance abuse data.

The present invention provides a cost effective alternative to the current ASI-based system to provide valid and reliable current substance abuse data, with less of a burden on clinical staff and to allow third parties to view the data.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

FIGS. 6A-6PPPPPPPP are excerpts from a sample script according to the present invention. The script contains some of the questions posed by the virtual interviewer to the respondents to obtain the respondents' information on their experience with one or more substance. The sample script and questions are presented for the purpose of illustration only, and therefore, it should be understood that the present invention is not construed as being limited thereto.

DETAILED DESCRIPTION OF THE INVENTION

Figure 1:
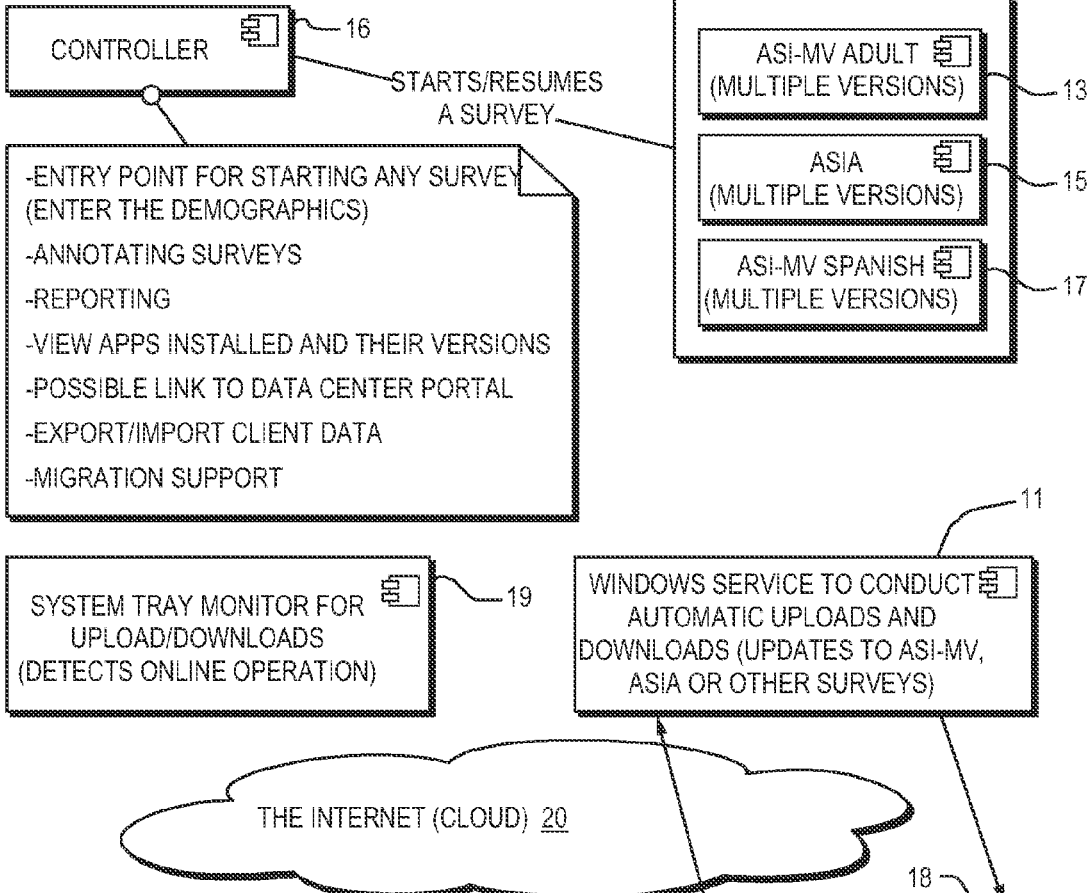
FIG. 1 is a schematic view of the components and their functions within an embodiment of the present invention.
Figure 1:
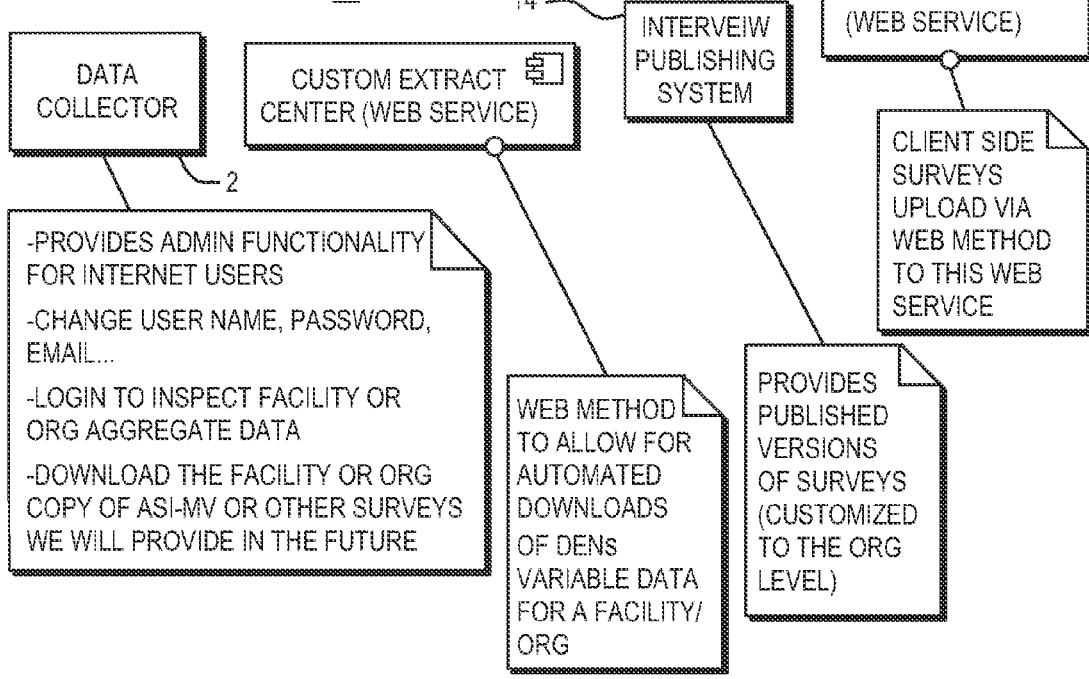

The preferred embodiment is a web-enabled substance abuse surveillance (as mentioned in the prior art) system that for the first time provides near real-time, product-specific, medically relevant data on rates and trends in substance abuse, using validated statistical methods. The preferred embodiment is a multimedia-based system that enables a respondent to self-administer an interview regarding the respondent's experience of a substance. The preferred embodiment collects data from various sources such as substance abuse centers, drug courts, Driving Under Influence programs, welfare programs, funded or unfunded research studies, to identify and measure the abuse of various substances, including prescription drugs, and method of administration by substance users. In one embodiment, the invention system is designed to collect information that differentiates the substances by brands and delivery systems and provides this information on a real-time or a near real-time basis to various stakeholders, including clinical facilities, pharmaceutical and medical entities (i.e. companies, hospitals, etc) and various substance rehabilitation facilities. The invention system can also collect medically relevant and actionable data on rates and trends in prescription substance abuse, using validated statistical methods. Scientific integrity and transparency are the backbone of the present invention system, starting from site selection to signal detection of "out of control" abuse rates to measuring the abuse rates of the substances.

While there are several other surveillance programs currently used by a number of users (i.e. clinical facilities or pharmaceutical companies, stockholders generally), each has some significant disadvantages in meeting surveillance needs:

1. The Drug Abuse Warning Network (DAWN) provides some real-time raw data and online queries to a limited audience, but only publishes drug abuse estimates annually. Its disadvantages include the fact that pharmaceutical companies have access to their own drugs only and they have no access to sub-national data breakdowns. Also, the prescription medication data are not product specific;

2. The Key Informant Network (KIN) is relatively inexpensive and is accepted by the Food and Drug Administration (FDA) and Drug Enforcement Administration (DEA). Its disadvantages include the fact that the accuracy and validity of the data are uncertain, there are no published validity checks of key respondents' responses and there are no efforts to address response biases of the respondents. Key Informant Networks produce subjective and qualitative data;

3. The National Survey on Drug Use and Health (formerly the National Household Survey on Drug Abuse) has some product specific data and is valid and reliable. Its disadvantages include the fact that the data are not real-time (2003 data was available September 2004), the population surveyed is not risk-relevant and changes are difficult to make; and 4. The Drug Evaluation Network Systems (DENS) collects substance abuse data from risk-relevant populations in mostly urban areas of the country. Its disadvantages include the fact that it is not real-time (June 2003 data was made available March 2004), and that it cannot make changes easily and is subject to rater bias during data collection.

Typically, these and similar ASI-based substance surveillance systems require a clinician, in a 40-60 minute session, to question a substance user (the interviewee) on the user's experience of a certain substance administered. The clinician must subsequently spend 10-20 minutes scoring an interviewee's responses depending on the level of expertise of the clinician and the complexity of the interviewee's substance use patterns. For the data to be meaningful, clinicians must undergo extensive training in administration, scoring and entering data into a database. To ensure reliability and validity of data, an existing ASI-based substance surveillance system can be quite expensive to administer, score, and enter. Clinicians paid to provide direct service must be diverted to learning and maintaining skills with the existing ASI-based substance surveillance system, in addition to the costs of data entry. Such cost concerns are significant for clinical facilities in this era of financial cutbacks for social services. Furthermore, even trained clinicians in research projects who undergo periodic review are known to "drift" with respect to their application of ASI scoring rules (Butler, S. F., Budman, S. H., Goldman, R. J., Beckley, K. E., Trottier, D., Newman, F. L. & Cacciola, J. S. (2001). *Initial Validation of a Computer-Assisted Addiction Severity Index: The ASI-MV. Psychology of Addictive Behaviors,* 15 (1), 4-12, herein incorporated by reference). The essential subjectivity inherent in the clinician's performance with respect to framing of questions, making ratings, and scoring can have large influences on the quality of the generated data. Therefore, clinical facilities are simultaneously called upon to both cut costs and provide more extensive and standardized assessments.

While, like similar substance surveillance systems, the present invention is developed based on the ASI, the present invention is a new system that is built to overcome the shortcomings of the existing systems exemplified above. The present invention provides the following inventive features that are critical for decision-making:

1. Providing data that identifies specific products (i.e. generic vs. branded drugs and oral pills vs. skin patches);

2. Near real-time data processing with on-line access;

3. Relevant geographic sampling (rural areas, undersampled in current systems, have been particularly beset with prescription drug abuse);

4. Determining the sources of diverted substances (i.e. questions on what proportion of respondents obtain substances from their own prescriptions, from patients, from thefts, from doctor shopping, forgery, etc.);

5. Assisting accurately to identify prescription drugs used and their experience, including details such as specific illness; and 6. Information identifying if abusers were prescribed drugs for therapeutic purposes (existing systems are silent on what proportion of abusers are pain patients)

7. Easily modifiable to assess new trends (the preferred embodiment is Internet-based and modular);

8. State-of-the-art signal detection strategies are employed to detect time points and regions of the country where abuse of a particular substance is greater than some standard (e.g., historical rate, absolute a priori rate, etc.);

9. Incorporating complementary and scientifically accepted qualitative methods for investigation and interpretation of signals (i.e. when a signal arises, a rapid investigation ensues for signal evaluation);

10. Respondent self-administered, research-based data gathering tool—Research-developed algorithm (allows for objective scoring of problem areas); and 11. Measuring outcome of interventions.

A CD-ROM version relating to the present invention (hereinafter "the CD-ROM" and incorporated by reference) has been previously developed, based on a public-domain, interview version of the ASI (McLellan, A. T., Luborsky, L., Woody, G. E., & O'Brien, C. P. (1980). *An improved evaluation instrument for substance abuse patients: The Addiction Severity Index. Journal of Nervous and Mental Disease,* 168, 26-33). Researchers found the CD-ROM be reliable and user-friendly (Butler, S. F.; Newman, F. L.; Cacciola, J. S.; Frank, A.; Budman, S. H.; McLellan, A. T.; Ford, S.; Blaine, J.; Gastfriend, D.; Moras, K.; Salloum, I. M.; Barber, J. P. (1998). *Predicting Addiction Severity Index (ASI) interviewer severity ratings for a computer-administered ASI. Psychological Assessment,* 10(4), 399-407; and Butler, S. F., Budman, S. H., Goldman, R. J., Beckley, K. E., Trottier, D., Newman, F. L. & Cacciola, J. S. (2001). *Initial Validation of a Computer-Assisted Addiction Severity Index: The ASI-MV. Psychology of Addictive Behaviors,* 15 (1), 4-12, which are herein incorporated by reference.). Respondents quickly mastered the CD-ROM regardless of education level, reading ability and computer experience. Furthermore, because it required minimal clinician time to administer, the CD-ROM accomplished the task with a fraction of the cost compared to a system that requires a human interviewer (clinician).

The CD-ROM questions respondents via a virtual interview. Despite the facile nature of its operation, the CD-ROM does not compromise the accuracy of the data it collects. The CD-ROM has built-in consistency checks for some of the questions that if not answered the same way, suggest that a respondent may misunderstand or be attempting to deceive the program. If not corrected when the respondent is prompted to do so, these inconsistencies are listed at the end of the Narrative Report for clinician follow-up.

The CD-ROM, however, does not permit real-time aggregate data processing within one clinical facility or across different facilities immediately after a respondent finishes the virtual interview on his substance experience. The results of the virtual interview are not immediately sent for data processing but stored with results of other respondents over a time interval. At the expiration of the time interval, the bundle of the stored results are sent to a center for data processing. Therefore, while there is less administrative cost compared to other existing substance surveillance systems, a clinical facility still has some administrative cost, the cost of storing the results and transmitting them to the data processing center.

Improving on the CD-ROM, the present invention, embodying key features of the CD-ROM, eliminates most of the administrative cost of storing and transmitting because the results of the virtual interview are sent immediately to the data processing center when the interview is ended. This feature on immediate transmission of the interview results facilitates the near real-time data processing for forming current substance abuse data. For purposes of describing substance use trends and pharmaceutical post-marketing surveillance, it is critical to obtain near real-time data on substance use of patients presenting for treatment or otherwise coming to the attention of authorities (e.g., criminal justice system, emergency rooms). Data that are collected or processed months later have a considerably reduced scientific and public health value for surveillance purposes.

Current substance abuse data referred to herein can include near real-time data on national, state and local prevalence and trends in illegal drug/substance use, the nonmedical use of prescription drugs, alcohol, and tobacco. The current substance abuse data can be targeted, for example, to a specific substance (i.e. heroin, oxycodone, or hydrocodone), a geographic location, a demographic group, an ethic group, depending on the type of the respondents involved in the interview process. In addition, based on the data, one may correlate substance use to other social problems such as legal problems, unemployment, and psychological distress (i.e. depression and suicidal tendencies).

In one embodiment, the present invention is a substance abuse surveillance system that includes a source of respondent responses to a self-administered virtual interview. A "source of respondent responses" herein can include a respondent who is providing the responses, or a clinical facility/medical establishment that is set up with a version of the present invention to enable the respondent to take the interview. The system can includes a web-enabled data collector coupled to receive from the source responses of multiple respondents.

Because the data collector can be connected via web, different constituents to the invention substance abuse surveillance system can access the data collector by visiting the hosting web site. Each constituent can browse the web-site to retrieve its respective information depending on their association to the substance abuse surveillance system. For example, a third party such as a pharmaceutical company or manager of a clinical facility can access the data collector to obtain information on rates and trends of abuse on a drug that the pharmaceutical company manufactures. Conversely, a clinical facility that provides for respondents to conduct the self-administered virtual interview can retrieve an analysis of responses from each respondent after the interview is terminated. Furthermore, an administrator of the data collector can access the web-site to modify the features of the data collector or to implement changes and/or updates thereof.

An embodiment of the present invention is configured to implement a dynamic system for building the self-administered virtual interview. This dynamic system enables the administrator to manage the data collector with much robustness that delivers much flexibility and efficiency. The dynamic system is a decision logic-based simulation of having the interview administered by a clinician. As such, the dynamic system is configured to make a multitude of decisions during the interview depending responses by a respondent. In one embodiment, the system uses outcome feedback to alter the questions it asks or clinical recommendations employing Artificial Intelligence algorithms. For example, the dynamic system can go back to a prior question, ask a series of questions, then decide if the interview should be resumed where it left off or ask a completetly different set of questions prior to resuming the interview. As explained earlier, while it is critical to obtain real-time data on substance use, it is also critical to timely implement different versions of a survey that include the questions of current issues as well (per drug, per respondent, per location/region, etc).

The features of the dynamic system are exemplified in the bullet points below to describe different embodiment thereof:

The Assessment/Survey construction platform has sets of questions grouped into "sections". A respondent answers the questions in a section and then goes on to the next section in the sequence or the next section can be skipped. The section(s) presented may be a function of the organization (or facility). Order of sections/questions can be customized by organization (or facility/clinical facility).

Questions of the interview are classified according to the type of responses to be validated. For example:

There may be a one of a mutually exclusive set (radio-button style);

Checkbox style (check one or more of the following);

Range answer (Respondent's answer falls into a range like scoring a test A, B, C, D, F or Likert scale);

Calendar for determining exact dates of events or just a count;

Spinner numeric answers; and

Type of the data for an answer can be date, time, text, currency or numeric (possibly an image map value as well).

Each version of the ASI generates composite scores and severitying ratings. A score or rating is defined as numeric summary quantities involving answers or other intermediate variables using a formula.

Questions, Answers, Versions, Sections, Sets of Questions (for National Outcome Measures (NOMS), Drug Evaluation Network System (DENS), American Society of Addiction Medicine (ASAM) are all first rate objects in the database and can be queried by standard statistical programs such as the Statistical Package for the Social Sciences (SPSS) or SAS to do ad hoc reporting.

Questions can be skipped depending upon the decision table logic behind a survey and this logic can be downloaded from the server to the respondent machine along with the questions, multimedia and answers.

A section based upon a downloadable configuration or condition can be disabled.

Questions can utilize text to speech technology.

Questions/Answers/Sections/Formulae for determining scores can all be versioned because more than one version may be in play on the respondent machine due to the 7-day window a respondent has for completion of an assessment.

Questions and answers can use techniques that do not require the respondent to be literate (e.g. blinking answers, a moving arrow pointing at the current answer, mouse activated slider, counters, big image radio-buttons, big image checkboxes, and graphics.)

The survey is configured to lock the respondent's information once entered so that the information cannot be changed by the respondent.

In setting up the logic flow of a survey, embodiments may place consistency or extreme value checks at any point in the process.

The severity ratings and composite scores can be calculated for each of the problem areas after each interview.

The client-side components can only upload completed surveys. A survey that is not completed after a predetermined period is deleted and the respondent will have to restart the test.

Local databases can be backed up and restored (or migrated) the data stored there to the new schema of the respondent data (probably SQL Express).

Integrating the current substance abuse data formed by the present invention with other external programs such as Netsmart or Smart.

Enabling self-registration, pay online for new subscribers (i.e. clinical facilities or pharmaceutical companies).

Creating an authoring tool to create a new report (the Interview Builder). The finished report can be configured to be available for all facilities/organizations/clinical facilities to download.

Tailoring questions to an organization (idiosyncratic to the organization and seen only by that organization).

Classifying questions by category.

Allowing facilities/organizations/clinical facilities to add, edit, or delete a facility specific ClientID that can be used by a system outside ASI-MV to track ASI-MV data.

Exposing a report of all drugs taken by an aggregate group of respondents to a third party such as a pharmaceutical company, including a report regarding a specific pharmaceutical product.

Printing a certificate of completion for each respondent that finishes the survey.

End User Licence Agreement when downloading the application.

Enabling the translation of the survey (in whole) to another language.

Any posts of upload data coming from different versions of the survey can be transferred to the new interim data center website and handled there.

The audio recording that reads the questions can be optionally turned off.

Tracking question, section and interview durations for analysis in the data center.

Implementing measures to prevent hacking out of the interview.

Configuring to allow customization of the respective home page of a customer. For example, a pharmaceutical company's homepage can be configured to show the data on the current abuse rate of the drug that the company manufactures. Conversely, a clinical facility's homepage can be configured to show the status of interviews that are being conducted.

Allowing the user to customize Quick Look to show, for example, what he deems the 10 most important questions.

In case a respondent pauses taking the interview in the middle of a section, the system is configured in such a way that he can start with the last question that he answered (retakes that question).

Creating a window of time for a respondent to finish the interview. For example, the system can be configured so that the respondent has to complete the interview in 7 days (start is time-stamped). He does not get extended an additional 7 days if he stops and resumes after the 7-day period. The system can be further configured so that if the respondent is actively taking the interview, the responses are not purged if the interview is outside the 7 day window.

Allowing the respondent to backtrack through the current section of an interview and change the answer to any question.

Repeating the entire set of questions and answers if the respondent desires.

Creating a Narrative Report which is a clinical report that summarizes and reports the responses to the ASI-MV of a single particular client or patient in a clinical facility. This report is made available in a standard word processor format (e.g., MS Word) and can be edited by the clinican. A print out of this report may be entered in a patient's clinical chart or other medical document.

In addition, the functionalities to the dynamic system also provide a set of authoring tools for non technical/software personnel with knowledge of how an interview should execute to build the virtual interview, including the tools make changes to:

the decision logic;
the visual format and multimedia component;
the rules that define how the narrative reports for interview administrators will work; and
the content that is to be provided in the narrative reports for interview administrators In managing different constituents to the substance abuse surveillance system of the present invention, the administrator can establish an account through the Data Center 2 by creating organizations/clinical facilities and any new users for that account, as shown in FIG. 1. In FIG. 1, the components are split into client-side 10 and server-side 12 categories. In the client-server configuration, the client programs may operate in a disconnected fashion while a self-administered virtual interview is underway. While connected background processes can upload completed respondent responses taken by the interview, download updated versions of purchased products or allow the clinician to browse the Data Collector 2. A client installation may be stopped and resumed and retains all data that it has experienced in a local data store and it can also upload the data to the Data Collector 2. The client installation provides relevant questions to respondents by considering all previously gathered data about the subject as well as data from many other sources and then dynamically decides what next questions to ask to include what content to present during said client installation.

The installation program installs and alters software for the client installation of the virtual interview, administrative tools and reports. The client tools, interview, reports and services can be downloaded from the internet or otherwise have the media put digitally on the client machine and installed. An administrator may make decisions to alter ways that the client installation interacts with the hosting hardware and software.

A System Tray Monitor 19 provides a visual cue when working online as well as shows which survey versions are installed and which are current. The user information is furnished by the user (user name, email, first name, last name, facility—parent organization if it exists). The Data Collector 2 automatically generates passwords and sends credentials to the user via email. The user is then able to change user name, email, first name, last name and email attributes after logging into the Data Collector 2. Any authorized user can log in and download the current version of the invention product they have purchased already tagged with their facility or organization name. Furthermore, the Interview Publishing System 14 of the server-side component is configured to provide different versions of the survey to the client-side components 10. The Interview Publishing System 14 enables a non-technical personnel to changes the questions, software, media, content of the interview. The Interview Publishing System 14 can implement approval process that is used to ensure that new changes to the interview are scientifically validated prior to public release. The Interview Publishing System 14 can also flag certain variants of the interview or items within a given interview to ensure that they are only available for download to select organizations, locations or other variants.

The System Tray Monitor 19 at the client-side 10 is provided for a visual cue when working on-line as well as showing which survey versions are installed and which are current. The automatic uploading of any updates or new versions of the survey uses Window Services 11.

The client-side 10 can be configured to upload different ASI programs such as ASI-MV Adult 13, ASIA (ASI-Adolescent) 15, or ASI-MV Spanish 17. Of the client-side components 10, the Controller 16 is a component that acts as a switchboard to spawn one of the surveys (or a particular version of a survey) or execute one of the other functions accessible to a clinician or administrator. The Controller 16 is the entry point for starting an interview. As referred to in the bullet points above, the client-side components 10 are configured with safety measures to prevent tampering and input of inaccurate or conflicting information by a respondent. For example, prior to initiating an interview, the clinician can enter a new respondent's demographic information and, the respondent cannot change the information once it is entered.

Furthermore, if the respondent cannot finish the interview in one sitting, the respondent can choose to resume the session later from the point he stopped previously. After the interview, the clinician may access a Narrative Report which can be annotated following a completed survey with comments or answers to extra questions about the respondent, but this information is not uploaded to the Upload Center 18 at the server-side components 12. Reports of aggregate data based on completed multiple surveys are accessible through the controller 16. An analysis of the responses from many respondents can be then exported to the server-side components via a a global computer network (i.e. the internet 20).

The interview questions to the respondent are presented in a virtual interview, which is "conducted" by virtual on-screen interviewers using multimedia and interactive media. These virtual interviewers introduce the respondent to the program, present the questions and offer further explanations and examples when needed, similar to a live interviewer.

In one embodiment, the invention is a client installation of monitoring services that includes a software for monitoring and notification of online status. The software monitors and communicates with a publishing server to check for new data, content and other information that may be uploaded or downloaded to a central repository or distributed location. The software is configured to be aware of the distributed system's status and can automatically transmit information, other software, content or media. This enables the client-component side 10 to install new data, content or any other digital medium for any variants of interviews or similar interview like experiences on the client machine or machine(s), to monitor for the online status, to upload a respondent's responses of an interview and to report the analysis of the responses to the Data Collector 2.

In another embodiment, the invention is administration tools for the administrator of each said installation of the virtual interview on a client machine including:

Administration tools for the administrator of each said installation to add new users to the system of any user type;

Administration tools for the administrator of each said installation to edit user information;

Administration tools for the administrator of each said installation to download new variants of the interview for trial;

Administration tools for the administrator of each said installation to download variants of the interview as a registered customer; and Administration tools for the administrator of each said installation to purchase additional uses or update license information.

Figure 2:
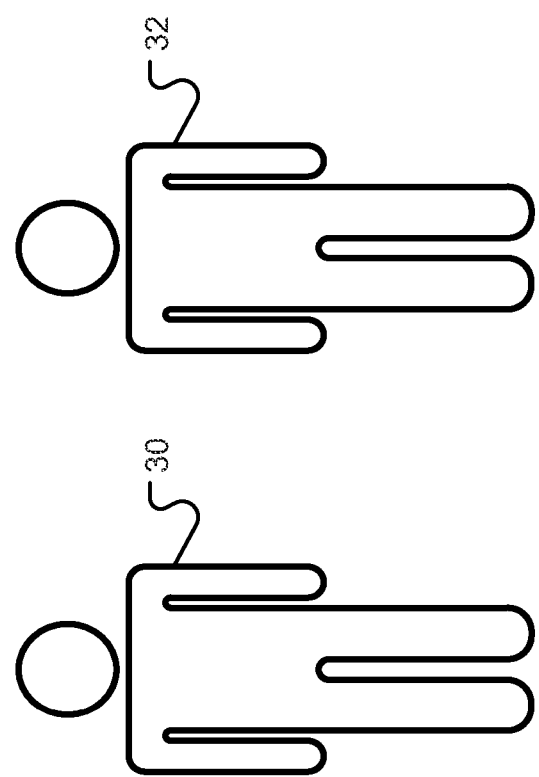
FIG. 2 is an illustration of virtual interviewers in a self-administered virtual interview of the present invention.

Excerpts from a sample script of the questions for the interview is presented in FIGS. 6.3, 6.6, 6.9, and 6.155. Using the dynamic system, which was described above, the questions can be developed or modified "on the fly" by trained individuals. Typically, at the beginning of and during the interview, a respondent can see and hear actors or a virtual interview on a medium (i.e. a monitor screen coupled of an interview server) providing directions on how to complete the self-administered virtual interview. For instance, as described in the excerpts from the script presented in FIGS. 6.3, 6.6, 6.9, and 6.155, when the respondent begins the interview, he sees two virtual interviewers 30, 32 appearing on a screen and providing an introduction to the interview, as shown FIG. 2. As the respondent proceeds with the interview, he would see a dialogue box with a question and hears an audio recording of the question read by the virtual interviewers. Because an audio recording that reads a question, an illiterate person can conduct the interview without difficulty.

Respondents are asked, by the virtual interviewers similar to 30 and 32, for instance, about their medical status, including medical problems/illnesses, medications, psychiatric history, whether they are on disability, and how many days in the past month medical problems interfere with their functioning. The questions are further explained and examples are given based on input from expertly trained interviewers during the applicant's research trials. Many questions like the ones on the script excerpts of FIGS. 6.3, 6.6, 6.9, and 6.155 are posed to the respondents.

Depending on the type, each question in the script is read by a different actor or a virtual interviewer. To provide authenticity, the present invention can be configured to have a different virtual interview appearing at a different stage of the interview as indicated in the script excerpts of FIGS. 6.3, 6.6, 6.9, and 6.155. For example, as the respondent proceeds questions from the subject matter of his background to the next on his medical history, a new virtual interviewer in a different audio reading appears. Therefore, one virtual interviewer asks the questions on alcohol and drug. Another virtual interviewer, for an instance questions the respondent on employment. The script excerpts of FIGS. 6.3, 6.6, 6.9, and 6.155 also includes other multiple virtual interviewers who ask questions on other areas regarding the respondent's life and substance use experience.

As previously discussed, the script excerpts of FIGS. 6C, 6F, 6I, and 6YYYYYY also include built-in decision-logic. This means that, like a human interviewer, the present invention is programmed to remember previous answers given (e.g., "I have never used heroin.") and skips subsequent questions that logically do not apply (e.g., "How many years have you used heroin?"). For example, if the respondent answers male to the question (see Question ASIG010 of the script excerpt in FIG. 6F) whether the respondent is male or female, the question (see Question M15AZ of the script excerpt in FIG. 6I) on whether the respondent is currently pregnant is skipped. Also, the script excerpts of FIGS. 6C, 6F, 6I, and 6YYYYYY include consistency checks to monitor whether the respondent answers consistently in relation to the respondent's other answer(s) in the virtual interview. For example, in the script excerpts of FIGS. 6C and 6YYYYYY, the answer to the question "In the last 30 days, have you been in a place where drugs and alcohol were not readily available, such as Jail or Prison" is checked against the answer to the question "In your life, how much total time have you spent in jail or prison since age 18?" Furthermore, checks on extreme values reported by respondents are included to help determine the validity of respondent's answers.

To accomplish this, questions are stored in a table or other data structure that links proper sequences of questions as a function of set responses. By following the human interviewer's logic, the present invention simulates for the respondent the experience of an interview. Respondents, even with no computer experience, have quickly learned to use the mouse to click on their answers with minimal assistance from staff. They not only were able to self-administer the program, but enjoyed doing so. They have numerous reports that respondents felt a sense of mastery when the certificate of completion is printed for them at the end. There have been some respondents who could not self-administer the present invention, due to physical limitations. In these unusual situations, clinicians have either entered the data for the respondent, or chosen an alternative assessment approach.

In one embodiment, for example, the following information can be obtained from the respondent through the virtual interview:

(i) the respondent (name, age, gender, heritage, health conditions, other medications/supplements routinely taken, residence location, occupation, education, legal problems, criminal activity, quality and structure of family and social relations, history of verbal, physical, and sexual abuse, history of psychological and emotional problems, sleeping habits, travel habits, eating habits, exercise regime, amount of time spent outdoor/indoors, etc);

(ii) the respondent's use of licit and illicit substances (name/chemical agent, lifetime use, quantity and frequency of use, specific brands of pharmaceutical agents used, how pharmaceutical agents are obtained, whether or not pharmaceutical agents are prescribed for medical problems, dosage taken, times of day taken, taken with/without food or water, prescribing person, dispensing pharmacist, temperature sensitivity, light sensitivity, forms taken by the respondent (liquid, tablet, capsule, powder or other forms of administration), etc); and (iii) related events (history of DTs and overdoses, treatment history, health and legal issues related to substance use, instances and duration of abstinence, reactions, changes in health of the respondent, dates/times start/end of each occurrence, etc); and various other details surrounding the use of the target substance(s) by the respondent.

The respondents are asked various questions. The invention system receives the information obtained through the virtual interview and stores the information in a relational database or similar datastore at a server. The datastore at the server is common or central to receiving and storing all such virtual interview collected data (by many users) across multiple and unrelated respondents accessing the system through a global computer network. The datastore at the server end stores the information in data cells logically related, cross-linked or otherwise indexed to each other for searching by various attributes and combinations thereof through any of the network respondents/servers (again achieving access through a global computer network). In this way, the present invention system provides a broader based collection of substance use data and enables various relationships among the data to be discovered/studied and reported to a wide variety of parties of interest who gain access via a global computer network.

In one embodiment of the present invention, the present invention system assesses various domains of functioning or problem areas related to addiction including: alcohol use, drug use, medical problems, psychiatric symptoms, family and social problems, legal problems, and employment problems. Questions are designed to obtain lifetime information about problem behaviors as well as those behaviors occurring during the 30 days prior to assessment.

The preferred embodiment has versatile applications and can be modified to target sub-sets of the population of substance abusers, including, but not limited to, different ethnic groups, genders, or different age demographics. In one embodiment of the present invention, the invention system is available in different languages, including, but not limited to, Spanish, Cantonese and Mandarin. In another embodiment, the invention system is adaptable to probe the risks associated with substance use/abuse in adolescents. In another embodiment, the invention system is adaptable to incarcerated individuals or others involved in the criminal justice system. Furthermore, in another embodiment of the present invention, the invention system is developed for respondents with handicaps. The invention system questions can be presented in both text and audio for those who cannot read. As various response "buttons" are read, the relevant button is highlighted, so illiterate individuals can tell which onscreen button represents their answer. Literate respondents can answer questions and move ahead at their own pace. Respondents indicate their answers using a mouse or other computer input devices. In another embodiment, modifications to the present invention can be made suitable for individuals who are sight impaired or blind. For example, the instructions of use and questions are read by the virtual interviewers so than a sight impaired respondent can participate.

Figure 3:
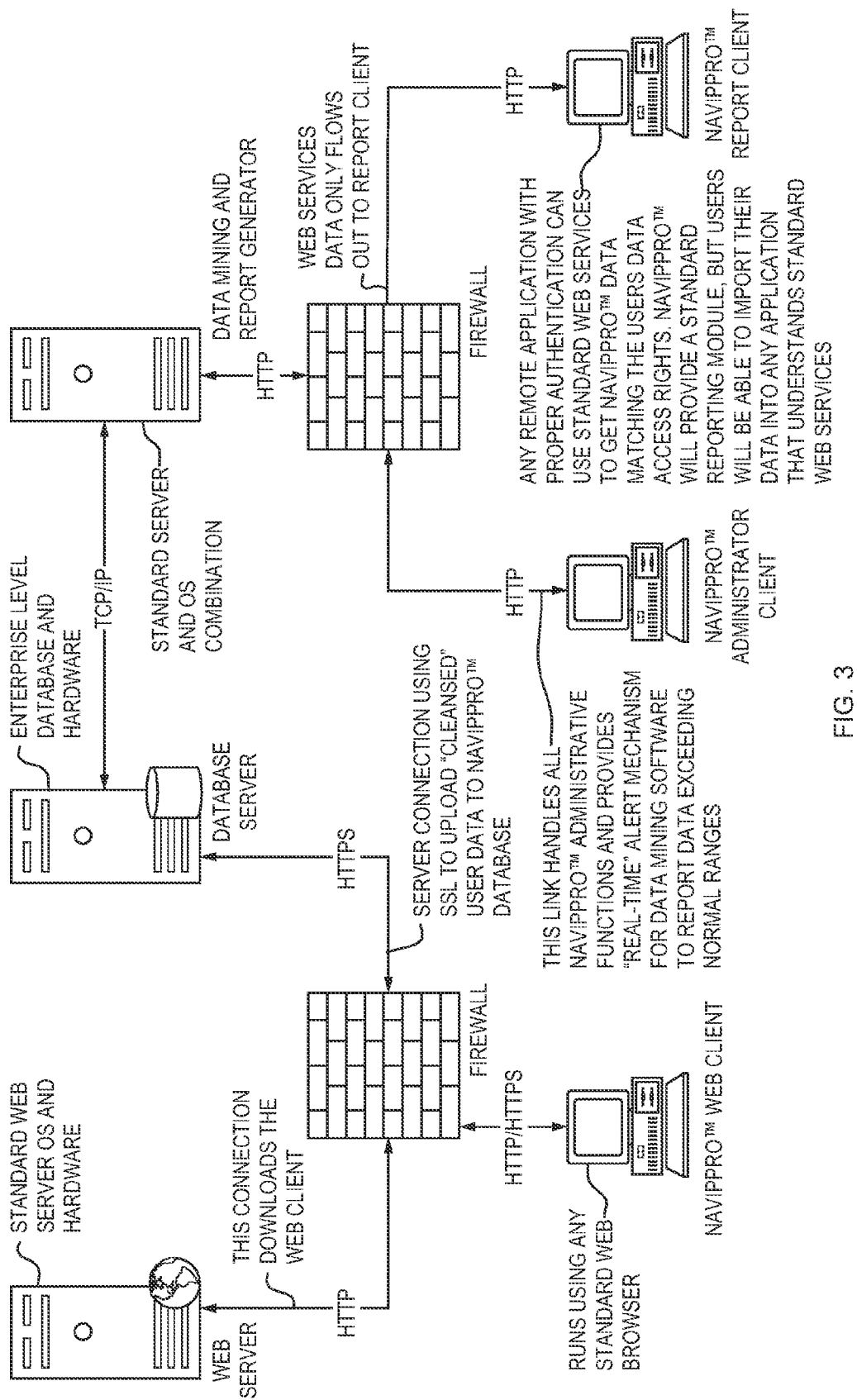
FIG. 3 is a schematic view of a computer network displaying how data is communicated between different entities in a study for assessing substance abuse rates according to the principles of the present invention.

A schematic view of a computer network embodying the present invention is presented in FIG. 3. In particular, FIG. 3 displays how data are collected and communicated between different entities in a study for assessing substance abuse rates in the present invention. A respondent can access the invention system at any of the data collection sites where the interview is to be administered and data is to be collected. An end node 34, to which a respondent logs on for taking/completing the interview, runs using any desktop application and connects to a web server 36 running a standard web server OS and hardware. The smart client can be any end node and it can be download using HTTP and upload the "cleansed" (i.e., respondent identifying material removed) data collected locally to an enterprise level database server 38 via an HTTP/HTTPS connection 40. These two servers 36, 38 are protected by a standard firewall 42. Upon the complete entry of the respondent's responses to the interview questions, the responses are analyzed at the end node 34, and the analysis can includes summary scores representing problem severity. The analysis is then transmitted from the database server 38 to the data mining and report generator server 44 running a standard server and OS combination using TCP/IP 46. This server 16 connects to an Administrator Client 47 and Report Client 48.

The Administrator Client 47 handles all administrative functions and provides a "real-time" alert mechanism for data mining software to report data exceeding normal ranges. It is connected to the Data mining and report generator server 44 via HTTP 45 and is also protected by a second firewall 43. For example, the Administrator Client 47 generates intelligent reports. These reports are able to pull out locally stored data that can be custom built for the client. There is also the datacenter. This is accessed through a web browser for doing the data mining and statistical reports.

The Report Client 48 is used by various third parties (i.e. pharmaceutical companies, clinical managers) to access near real-time data. A stakeholder can utilize standard web services and receive data generated by the data mining and report generator server 44 via HTTP 45. Any remote application with proper authentication can use standard web services to get the present invention data, matching the user's data access rights. The invention system can provide a standard reporting module, but the data can be imported into any application.

Figure 4:
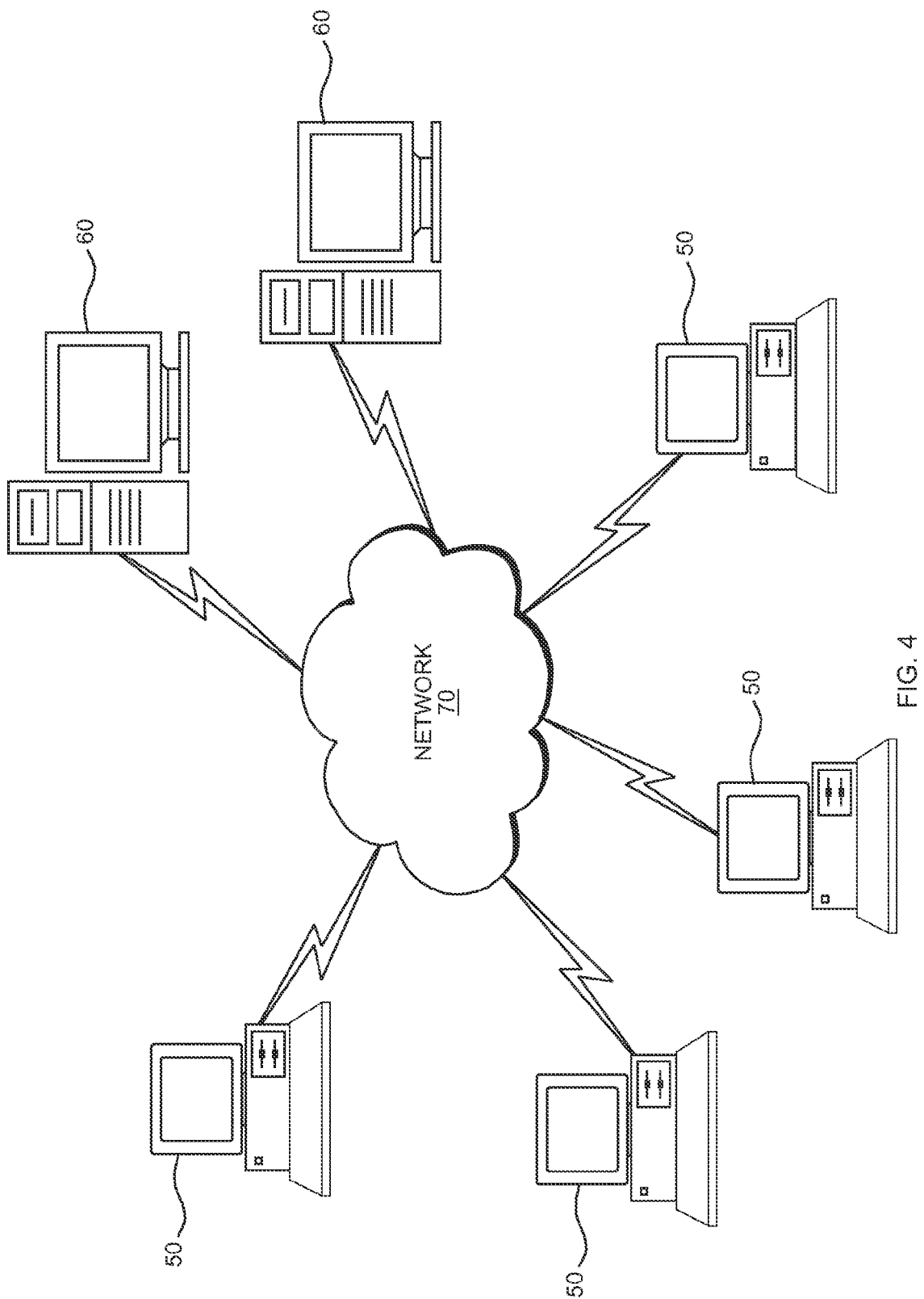
FIG. 4 is a schematic view of a computer network in which embodiments of the present invention may be implemented.

The end nodes 34, 47, 48 and servers 36, 38, 44 of the invention may be computer processes 50, 60 of a variety of networks as generally illustrated in FIG. 4. Referring to FIG. 4, client computer(s)/devices 50 and server computer(s) 60 provide processing, storage, and input/output devices executing application programs and the like. Client computer(s)/devices 50 can also be linked through communications network 70 to other computing devices, including other client devices/processes 50 and server computer(s) 60. Communications network 70 can be part of a remote access network, a global network (e.g., the Internet), a worldwide collection of computers, Local area or Wide area networks, and gateways that currently use respective protocols (TCP/IP, Bluetooth, etc.) to communicate with one another. Other electronic device/computer network architectures are suitable.

Figure 5:
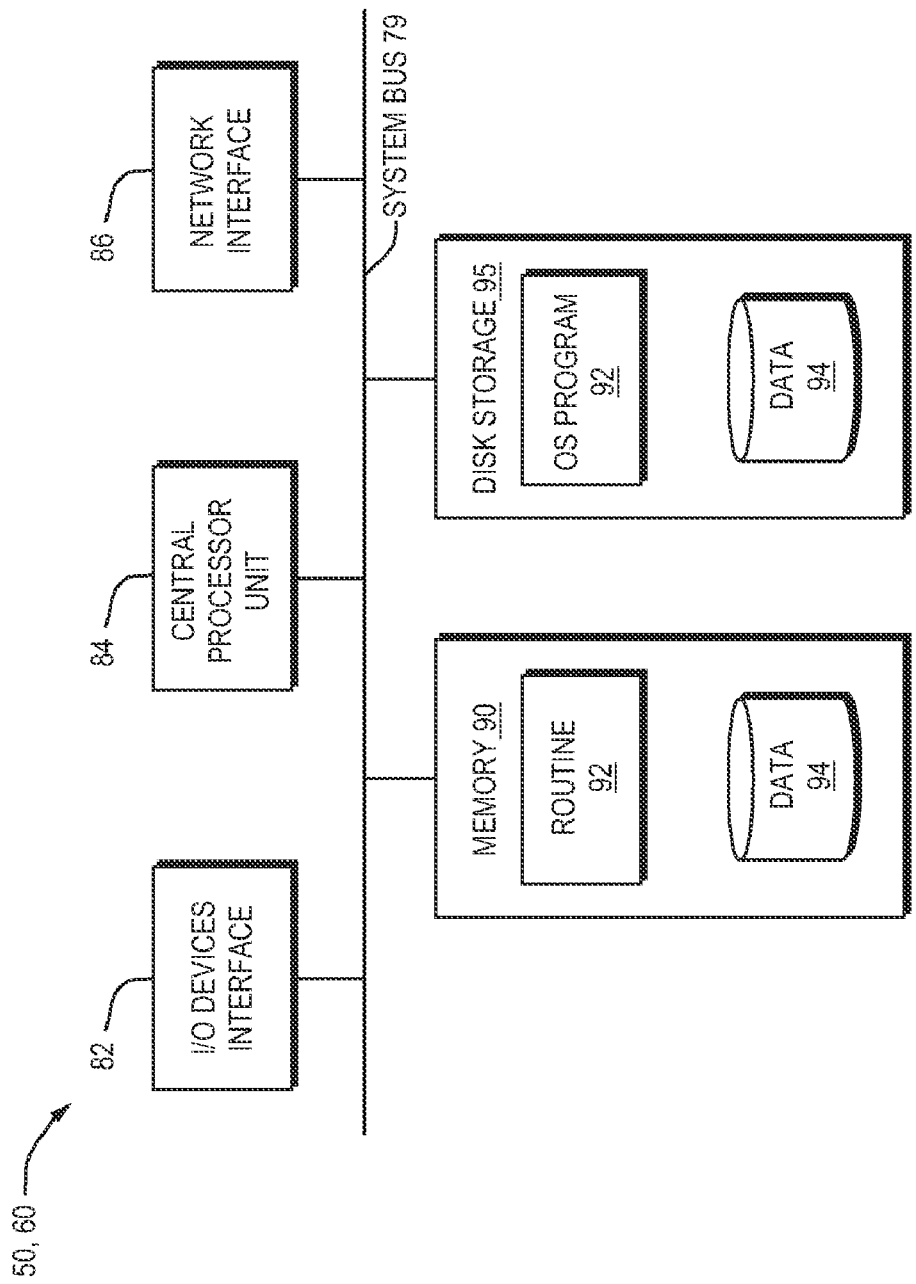
FIG. 5 is a block diagram of a computer mode of the network of FIG. 4.

FIG. 5 is a diagram of the internal structure of a computer (e.g., client processor/device 50 or server computers 60) in the computer system of FIG. 4. Each computer 50, 60 contains system bus 79, where a bus is a set of hardware lines used for data transfer among the components of a computer or processing system. Bus 79 is essentially a shared conduit that connects different elements of a computer system (e.g., processor, disk storage, memory, input/output ports, network ports, etc.) that enables the transfer of information between the elements. Attached to system bus 79 is I/O device interface 82 for connecting various input and output devices (e.g., keyboard, mouse, displays, printers, speakers, etc.) to the computer 50, 60. Network interface 86 allows the computer to connect to various other devices attached to a network (e.g., network 70 of FIG. 5). Memory 90 provides volatile storage for computer software instructions 92 and data 94 used to implement an embodiment of the present invention (e.g., the interview questions/answers database, data structures and invention system 7 discussed above in FIGS. 1-4). Disk storage 95 provides non-volatile storage for computer software instructions 92 and data 94 used to implement an embodiment of the present invention. Central processor unit 84 is also attached to system bus 79 and provides for the execution of computer instructions.

In one embodiment, the processor routines 92 and data 94 are a computer program product (generally referenced 92), including a computer readable medium (e.g., a removable storage medium such as one or more DVD-ROM's, CD-ROM's, diskettes, tapes, etc.) that provides at least a portion of the software instructions for the invention system. Computer program product 92 can be installed by any suitable software installation procedure, as is well known in the art. In another embodiment, at least a portion of the software instructions may also be downloaded over a cable, communication and/or wireless connection. In other embodiments, the invention programs are a computer program propagated signal product 107 embodied on a propagated signal on a propagation medium (e.g., a radio wave, an infrared wave, a laser wave, a sound wave, or an electrical wave propagated over a global network such as the Internet, or other network (s)). Such carrier medium or signals provide at least a portion of the software instructions for the present invention routines/program 92.

In alternate embodiments, the propagated signal is an analog carrier wave or digital signal carried on the propagated medium. For example, the propagated signal may be a digitized signal propagated over a global network (e.g., the Internet), a telecommunications network, or other network. In one embodiment, the propagated signal is a signal that is transmitted over the propagation medium over a period of time, such as the instructions for a software application sent in packets over a network over a period of milliseconds, seconds, minutes, or longer. In another embodiment, the computer readable medium of computer program product 92 (e.g., the invention system) is a propagation medium that the computer system 50 may receive and read, such as by receiving the propagation medium and identifying a propagated signal embodied in the propagation medium, as described above for computer program propagated signal product.

The present invention is now illustrated in further detail by way of the following examples, but it should be understood that the present invention is not construed as being limited thereto.

Example 1

Enhanced Accuracy and Efficiency of the Present Invention

Researchers have documented equivalency or enhanced accuracy and efficiency obtained by direct substance user assessment, compared to standard interviewer-based approaches. Substance users, even those who are illiterate or lack computer skills, appear to prefer the engaging computer-based version. It has been shown that substance users tend to be more open and honest with a computer than with human, in-person interviewer/clinician. Interview-based approaches may be compromised by interviewer bias, rapid turnover of interviewers/clinicians at sites, variable training, and increased expense.

It is shown that only 2% of respondents skipped 6 or more questions (N=902 respondents in 3 studies), and in a recent analysis of a database, 1.9% skipped 6 or more questions (N=1,434).

Example 2

The Present Invention is Superior Over the Existing ASI-based Systems

Clients in treatment (N=202) self-administered the present invention to examine the test-retest reliability, criterion validity and convergent-discriminant validity. Therefore, the present invention has excellent validity and reliability, performing as well or better than clinician-administered ASI systems. The present invention was found to be acceptable and required about the same amount of clinician time to administer (mean of 43 minutes compared to about 45 minutes to an hour for the interview) while requiring minimal staff time. The present invention has excellent test-retest reliability (e.g., intraclass correlations between 0.81 and 0.97 for Composite Scores). Convergent/discriminant validity tests of the present invention were superior to the standard ASI systems. Excellent test-retest reliability was observed for all scores. Criterion validity was tested against the interviewer-administered version of the ASI and was good for the Composite Scores. For Severity Ratings, variable agreement was observed between the present invention and each interviewer, suggesting poor interrater reliability among interviewers. This conclusion was bolstered by a finding of superior convergent-discriminant validity. In addition, analysis of the discriminate validity matrix suggested that the present invention demonstrated better convergent and discriminate validity than the standard, interviewer-administered ASI.

Therefore, the present invention has excellent validity and reliability, performing as well or better than clinician-administered ASIs.

Example 3

Other Features of the Present Invention

The present invention can also include the following features:

1. In collaboration with pharmaceutical companies and experts, questions and graphics can be timely (and per respondent or location specifically) added to help identify prescription drug problems and trends. This can include audio, video and pictures to assist clients in accurately identifying prescription drugs used, and their experience with specific illnesses, pain and medical treatment. In addition, questions can be added to attempt to determine the sources of medication and pathways to abuse.

2. State-of-the-art signal detection strategies—The latest in Statistical Process Control (SPC) methods can be implemented, in order to create statistical models that can generate "alarms" when unexpected substance use rates ("out of control" events) occur. In addition, Geographic Information Systems (GIS)-based methods can be implemented to generate geo-spatial analyses of substance abuse trends. A similar system can be developed for worldwide healthcare delivery.

3. Web-site screen and tools for customer access to near real-time data—Using the preferred embodiment can enable clients to access a Web-site interface and tools to view and manipulate their data in near real-time. This embodiment facilitates the clients to "drill down" into data to learn more about prescription medication abuse trends. The site can also provide summary reports on analyses of the data.

While this invention has been particularly shown and described with references to preferred embodiments thereof, it will be understood by those skilled in the art that various changes in form and details may be made therein without departing from the scope of the invention encompassed by the appended claims.

The invention claimed is:

1. An interactive substance use surveillance system comprising:
   a memory;
   a computer processor operatively coupled to the memory;
   a computer readable medium storing instructions that when executed by the computer processor causes the computer processor to provide a self-administered virtual interview, the self-administered virtual interview being formed of multimedia and interactive media, and having a series of different sections and a respective transition scene between each pair of sections in the series, different pairs of sections having different respective transition scenes, and different sections having different respective actors,
   each of the different sections of the virtual interview having a respective introduction scene in which an audio and visual recording of a respective actor announces to a respondent that questions about to be asked during the section are on a particular subject matter, different sections employing audio and visual recordings of the different actors;
   each section of the virtual interview presenting its respective introduction scene followed by: i) visually and audibly presenting questions to the respondent in both text and audio, the questions being audibly presented by an audio recording of the corresponding actor of the section reciting the questions, ii) highlighting selectable responses to the questions while the computer processor audibly presents the responses to the respondent for the respondent to choose, the responses being audibly presented by an audio recording of the corresponding actor of the section reciting the responses;
   in a subject transition scene between a respective pair of sections in the series, providing to the respondent an audio and visual recording of an actor different from the actors of the different sections, the subject transition scene providing to the respondent a transition from one section of the respective pair to a next section of the pair after the respondent completes the one section of the pair in the virtual interview, the virtual interview being configured with consistency checks and using (a) the different transition scenes transitioning through the different pairs of sections and (b) the audio and visual recordings of different actors across the different sections and different transition scenes in a manner enabling self-administration of the virtual interview through to completion of the virtual interview, the virtual interview preventing against input of inconsistent information as responses by the respondent; and
   a computer-based data collector in electronic communication with the computer readable medium and configured to receive responses chosen by the respondent in the self-administered virtual interview, the data collector receiving the respondent chosen responses immediately after the self-administered virtual interview ends and analyzing the respondent chosen responses, the analyzing forming current substance use data, the data collector allowing access to the current substance use data by third parties, and wherein the data collector is coupled to receive the respondent chosen responses in a manner enabling delay-free, continuous feed of the respondent responses.

2. The substance use surveillance system of claim 1 further including an interview publishing system that enables a non-technical/non-software personnel to modify or update the contents of the self-administered virtual interview.

3. The substance use surveillance system of claim 2, wherein the interview publishing system further dynamically formulates and provides questions to the self-administered virtual interview.

4. The substance use surveillance system of claim 1, wherein the self-administered virtual interview is conducted in a non-English language.

5. The substance use surveillance system of claim 1, wherein the non-English language includes Spanish, Cantonese and Mandarin.

6. The substance use surveillance system of claim 1, wherein the analysis is processed at an on-site location of the self-administered virtual interview.

7. The substance use surveillance system of claim 6, wherein the on-site location and the data collector communicates to each other via a global computer network.

8. The substance use surveillance system of claim 6 further including an interview publishing system that enables a non-technical/non-software personnel to modify or update contents of the self-administered virtual interview.

9. The substance use surveillance system of claim 8, wherein the interview publishing system further dynamically formulates questions and provides the dynamically formulated questions to the self-administered virtual interview.

10. The substance use surveillance system of claim 9, wherein the dynamically formulated and provided questions include pharmaceutical product specific questions.

11. The substance use surveillance system of claim 1, wherein the analysis includes summary scores representing problem severity that are generated at the end of the self-administered virtual interview.

12. The substance use surveillance system of claim 1, wherein the current substance use data indicates trends and rates of substance use in a geographical area.

13. The substance use surveillance system of claim 1, wherein the respondent is an adolescent, an illiterate person or an illiterate adolescent.

14. An interactive substance abuse surveillance system comprising:
   a memory;
   a processor operatively coupled to the memory;
   a non-transitory computer readable medium executed by the processor and configured to provide a self-administered virtual interview to a respondent and obtain information on the respondent's experience with one or more substances, the self-administered virtual interview including multimedia and interactive media, and having a series of different sections and a respective transition scene between different pairs of sections in the series, different pairs of sections having different respective transition scenes, and different sections having different actors, each of the different sections of the virtual interview having a respective introduction scene during which an audio and visual recording of a respective actor announces to a respondent that questions about to be asked during the section are on a particular subject matter, different sections employing audio and visual recordings of the different actors;

in each section of the virtual interview, presenting the section's respective introduction scene, followed by: i) presenting the respondent with questions in both text and audio, the questions being presented by an audio recording of the corresponding actor of the section reciting the questions, and ii) highlighting viewable text of selectable responses to the questions while the system audibly presents the response to the respondent for the respondent to choose, the responses being audibly presented by an audio recording of said corresponding actor of the section reciting the responses;

in a subject transition scene between a corresponding pair of sections in the series, providing to the respondent an audio and visual recording of an actor different from the actors of the different sections, said subject transition scene providing to the respondent a transition from one section of the pair of sections to a next section of the pair after the respondent completes the one section of the pair in the virtual interview, the virtual interview being configured with consistency checks and using (a) the different transition scenes transitioning through the different pairs of sections and (b) the audio and visual recordings of different actors across the different sections and different transition scenes in a manner enabling self-administration of the virtual interview through to completion of the virtual interview, and the virtual interview preventing against input of inconsistent information as responses by the respondent; and a data collector in electronic communication with the computer readable medium and configured to receive the information obtained from the respondent immediately after the respondent completes the self-administered virtual interview and to analyze the information obtained from the respondent to generate current substance abuse data, wherein the data collector allows access to the current substance abuse data by third parties, and wherein the data collector is coupled to receive the information obtained from the respondent in a delay-free, continuous feed manner.

15. The substance abuse surveillance system of claim 14, wherein the information obtained from the respondent is analyzed at a site of the self-administered virtual interview.

16. The substance abuse surveillance system of claim 15, wherein the site and the data collector communicate to each other via a global computer network.

17. The substance abuse surveillance system of claim 14 further including an interview publishing system that enables a non technical/software personnel to modify or update the contents of the self-administered virtual interview.

18. The substance abuse surveillance system of claim 17, wherein the interview publishing system further dynamically formulates and provides questions to the self-administered virtual interview.

19. The substance abuse surveillance system of claim 18, wherein the dynamically formulated and provided questions include pharmaceutical product specific questions.

20. The substance abuse surveillance system of claim 14, wherein the interactive medium is configured to provide the self-administered virtual interview according to decision logic that decides which question to ask based on response chosen by the respondent to a previous question.

21. The substance abuse surveillance system of claim 20, wherein one or more questions of the self-administered virtual interview can be skipped depending on responses to other questions.

22. The substance abuse surveillance system of claim 20, wherein the decision-logic can be: i) downloaded from the data collector as computer executable instructions and ii) modified according a predetermined parameter.

23. The substance abuse surveillance system of claim 22, wherein the predetermined parameter is established dependent on one or more of the following: alcohol use, drug use, medical problems, psychiatric history, family and social history, legal problems, employment history, an identity of one or more substance products, and a source of the one or more substance products.

24. The substance abuse surveillance system of claim 14, wherein the analysis includes summary scores representing problem severity that are generated at the end of the self-administered virtual interview.

25. The substance abuse surveillance system of claim 14, wherein the data collector can receive the current substance abuse data from two or more sites that enables the self-administered virtual interview.

26. The substance abuse surveillance system of claim 25, wherein the current substance abuse data indicates trends and rates of substance abuse in a geographical area.

27. The substance abuse surveillance system of claim 14, wherein the respondent is illiterate.

28. The substance abuse surveillance system of claim 14, wherein the self-administered virtual interview is conducted in a non-English language.

29. The substance abuse surveillance system of claim 28, wherein the non-English language includes Spanish, Cantonese and Mandarin.

30. The substance abuse surveillance system of claim 14, wherein the self-administered virtual interview includes questions on one or more following subject matters: alcohol use, drug use, medical problems, psychiatric history, family and social history, legal problems, employment history, an identity of one or more substance products, and a source of the one or more substance products.

31. The substance abuse surveillance system of claim 14, wherein the self-administered virtual interview is directed to adolescents.

32. A computer implemented method for obtaining data on substance abuse, comprising the steps of:

using a computer, providing for respondents to log onto to complete a self-administered virtual interview, the virtual interview having a series of different sections and a respective transition scene between each pair of sections in the series, different pairs of sections having different respective transition scenes, each of the different sections of the virtual interview having a respective introduction scene, and different sections having different actors, the computer providing the self-administered virtual interview to a subject respondent by:

for a given introduction scene of a section, the computer providing to the respondent, an audio and visual recording of the respective actor of the section announcing that questions about to be asked during the section are on a particular subject matter, different sections employing audio and visual recordings of the different actors;

in each section of the virtual interview, after it's respective introduction scene, the computer: i) presenting the respondent with questions in both text and audio, the questions being presented by an audio recording of the corresponding actor of the section reciting the questions, and ii) highlighting selectable responses to the questions while audibly presenting the responses to the respondents for the respondents to choose, the responses being audibly presented by an audio recording of said corresponding actor reciting the responses;

in a subject transition scene between a respective pair of sections in the series, the computer providing to the respondent an audio and visual recording of an actor different from the actors of the different sections, the subject transition scene providing to the respondent a transition from one section of the pair to a next section of the pair after the respondent completes the one section of the pair in the virtual interview, the virtual interview being configured with consistency checks and using (a) the different transition scenes transitioning through the different pairs of sections and (b) the audio and visual recordings of different actors across the different sections and different transition scenes in a manner enabling self-administration of the virtual interview through to completion of the virtual interview, and the virtual interview preventing against input of inconsistent information as responses by the respondent;

immediately after the subject respondent completes the self-administered virtual interview, receiving, by a computer processor, respondent responses to the self-administered virtual interview, the self-administered virtual interview regarding the subject respondent's experience with one or more substances; and analyzing, by a server computer, the received respondent responses in a manner that results in forming current substance abuse data;

wherein the formed current substance abuse data is accessible to third parties.

33. The computer implemented method of claim 32, wherein the step of analyzing the received respondent responses and forming current substance abuse data includes generating a respective summary scores representing problem severity for each self-administered virtual interview at the end of the interview.

34. The computer implemented method of claim 32 further comprising the step of electronically sending the received respondent response to a data collector via a global computer network, the data collector performing the analysis.

35. The computer implemented method of claim 34, wherein the global computer network includes an interview publishing system, the interview publishing system configured to dynamically formulate and provide questions to the self-administered virtual interviews.

36. The computer implemented method of claim 35, wherein the dynamically formulated and provided questions include product specific questions.

37. The computer implemented method of claim 32, wherein each self-administered virtual interview is provided according to decision logic that decides which question to ask based on respondent response to a previous question.

38. The computer implemented method of claim 37, wherein one or more questions of the self-administered virtual interviews can be skipped depending on responses to other questions.

39. The computer implemented method of claim 32 further including the steps of:

downloading from a server, computer executable instructions providing decision-logic for deciding which question to ask based on a respondent response to a previous question, the self-administered virtual interviews being provided to the respondents according to the decision-logic; and modifying the self-administered virtual interviews according a predetermined parameter.

40. The computer implemented method of claim 39, wherein the predetermined parameter is established dependent on one or more of the following: alcohol use, drug use, medical problems, psychiatric history, family and social history, legal problems, employment history, an identity of one or more substance products, and a source of the one or more substance products.

41. The computer implemented method of claim 32, wherein the self-administered virtual interview includes multimedia and interactive media.

42. The computer implemented method of claim 41, wherein a respective respondent is illiterate.

43. The computer implemented method of claim 32, wherein the self-administered virtual interviews are conducted in a non-English language.

44. The computer implemented method of claim 43, wherein the non-English language includes Spanish, Cantonese and Mandarin.

45. The computer implemented method of claim 32, wherein the self-administered virtual interviews include questions on one or more following subject matters: alcohol use, drug use, medical problems, psychiatric history, family and social history, legal problems, employment history, an identity of one or more substance products, and a source of the one or more substance products.

46. The computer implemented method of claim 32, wherein the self-administered virtual interviews are directed to adolescents.

47. A non-transitory computer readable medium comprising:

a set of computer program instructions embodied on the non-transitory computer readable medium for forming current substance abuse data, the instructions when executed by a computer causing the computer to:

configure a self-administered virtual interview, the virtual interview having a series of different sections and a respective transition scene between each pair of sections in the series, each of the different sections having a different introduction scene and different sections having different actors;

provide the self-administered virtual interview to a respondent by:

in a subject introduction scene of a section, providing to the respondent, an audio and visual recording of a respective actor of the section announcing that questions about to be asked during the section are on a particular subject matter, different sections employing audio and visual recordings of the different actors;

in each section of the virtual interview, after its respective introduction scene: i) presenting the respondent with questions in both text and audio, the questions being presented by an audio recording of the respective actor of the section reciting the questions, and ii) highlighting selectable responses to the questions while the computer audibly presents the responses to the respondent for the respondent to choose, the responses being audibly presented by an audio recording of the respective actor reciting the responses;

in a subject transition scene between a corresponding pair of sections in the series, providing to the respondent an audio and visual recording of an actor different from the actors of the different sections, the subject transition scene providing to the respondent a transition from one section of the pair to a next section of the pair after the respondent completes the one section of the pair in the virtual interview, the virtual interview being configured with consistency checks and using (a) the different transition scenes transitioning through the different pairs of sections and (b) the audio and visual recordings of different actors across the different sections and different transition scenes in a manner enabling self administration of the virtual interview through to completion of the virtual interview, and the virtual interview preventing against input of inconsistent information as responses by the respondent;

immediately after the respondent completes the self-administered virtual interview, receive respondent responses to the self-administered virtual interview, the virtual interview regarding the respondent's experience with one or more substances; and analyze the received respondent responses and form current substance abuse data wherein the formed current substance abuse data is accessible to third parties.

48. The computer readable medium of claim 47, wherein the computer program instructions further comprising an interactive media for conducting a self-administered virtual interview on the respondent's experience with one or more substances, the interactive media conducting the self-administered virtual interview via a global computer network.

49. The computer readable medium of claim 47, wherein at least some portion of the computer program instructions include instructions to request data or request instructions over a telecommunications network.

50. The computer readable medium of claim 47, wherein at least some portion of the computer program is transmitted over a global network.

51. The computer readable medium of claim 47, wherein the computer readable medium includes a removable storage medium.

52. The computer readable medium of claim 51, wherein the removable storage medium includes any of a CD-ROM, a DVD-ROM, a diskette, and a tape.

* * * * *